(12) United States Patent
Engstrand et al.

(10) Patent No.: US 10,881,519 B2
(45) Date of Patent: Jan. 5, 2021

(54) BONE IMPLANTS FOR CORRECTING BONE DEFECTS

(71) Applicant: OssDsign AB, Uppsala (SE)

(72) Inventors: Thomas Engstrand, Uppsala (SE); Jan Bohlin, Uppsala (SE); Jonas Åberg, Uppsala (SE); Håkan Engqvist, Uppsala (SE)

(73) Assignee: OSSDSIGN AB, Uppsala (SE)

(*) Notice: Subject to any disclaimer, the term of this patent is extended or adjusted under 35 U.S.C. 154(b) by 0 days.

(21) Appl. No.: 15/503,666

(22) PCT Filed: Aug. 13, 2015

(86) PCT No.: PCT/IB2015/056186
§ 371 (c)(1),
(2) Date: Feb. 13, 2017

(87) PCT Pub. No.: WO2016/024248
PCT Pub. Date: Feb. 18, 2016

(65) Prior Publication Data
US 2017/0239054 A1    Aug. 24, 2017

Related U.S. Application Data

(60) Provisional application No. 62/037,595, filed on Aug. 14, 2014.

(51) Int. Cl.
*A61F 2/28* (2006.01)
*A61F 2/30* (2006.01)
(Continued)

(52) U.S. Cl.
CPC ........ *A61F 2/30965* (2013.01); *A61B 17/688* (2013.01); *A61F 2/2875* (2013.01);
(Continued)

(58) Field of Classification Search
CPC .............................................. A61F 2002/2835
See application file for complete search history.

(56) References Cited

U.S. PATENT DOCUMENTS

| 4,839,215 A | 6/1989 | Starling et al. |
| 4,905,679 A | 3/1990 | Morgan |

(Continued)

FOREIGN PATENT DOCUMENTS

| CN | 2607960 Y | 3/2004 |
| CN | 1919357 A | 2/2007 |

(Continued)

OTHER PUBLICATIONS

Bohner et al, J. Biomaterials, 26(33):6423-6429 (2005).
(Continued)

*Primary Examiner* — Jacqueline Woznicki
(74) *Attorney, Agent, or Firm* — Porter Wright Morris & Arthur LLP

(57) ABSTRACT

A mosaic implant (2010) comprises a mesh support frame comprising a plurality of polygonal support rings (2040 A, B, C) connected by a plurality of struts (2014), and a plurality of mosaic plates (2012). The support rings are positioned within the mosaic plates; the struts extend between adjacent plates. An implant (1510) for filling a bore hole comprises a plate (1512) and a support frame (1520) having a central portion (1522) located at least partially within the plate, a polygonal outer rim (1524) having a plurality of fastening points for attaching the implant to bone surrounding a bore hole, and a plurality of arms (1530) extending between the central portion and the outer rim. The plurality of arms extend inwardly and downwardly away from the outer rim such that the central portion is located (Continued)

below the plane of the outer rim and the upper surface of the plate is flush with or slightly above the upper surface of the outer rim.

21 Claims, 37 Drawing Sheets

(51) Int. Cl.
  *A61B 17/68* (2006.01)
  *A61F 2/00* (2006.01)
(52) U.S. Cl.
  CPC .............. *A61F 2/0059* (2013.01); *A61F 2/28* (2013.01); *A61F 2/2846* (2013.01); *A61F 2002/2835* (2013.01); *A61F 2002/3092* (2013.01); *A61F 2002/3096* (2013.01); *A61F 2002/30143* (2013.01); *A61F 2002/30324* (2013.01); *A61F 2002/30451* (2013.01); *A61F 2002/30462* (2013.01); *A61F 2002/30578* (2013.01); *A61F 2002/30957* (2013.01); *A61F 2002/30985* (2013.01); *A61F 2310/00353* (2013.01)

(56) References Cited

U.S. PATENT DOCUMENTS

| | | |
|---|---|---|
| 5,139,497 A | 8/1992 | Tilghman et al. |
| 5,152,836 A | 10/1992 | Hirano et al. |
| 5,201,737 A | 4/1993 | Leibinger et al. |
| 5,338,356 A | 8/1994 | Hirano et al. |
| 5,368,602 A | 11/1994 | De la Torre |
| 5,372,598 A | 12/1994 | Luhr et al. |
| 5,380,328 A | 1/1995 | Morgan |
| 5,468,242 A | 11/1995 | Reisberg |
| 5,503,164 A * | 4/1996 | Friedman ............ A61B 17/8085 128/897 |
| 5,545,226 A | 8/1996 | Wing et al. |
| 5,605,713 A | 2/1997 | Boltong |
| 5,683,667 A | 11/1997 | Fulmer et al. |
| 5,690,631 A * | 11/1997 | Duncan .............. A61B 17/8085 606/281 |
| 5,702,419 A | 12/1997 | Berry et al. |
| 5,743,913 A * | 4/1998 | Wellisz .............. A61B 17/8061 606/285 |
| 5,752,958 A * | 5/1998 | Wellisz .............. A61B 17/8085 606/280 |
| 5,766,176 A * | 6/1998 | Duncan .............. A61B 17/8085 606/281 |
| 5,782,971 A | 7/1998 | Constantz et al. |
| 5,783,217 A | 7/1998 | Lee et al. |
| 5,785,712 A | 7/1998 | Runciman et al. |
| 5,814,048 A | 9/1998 | Morgan |
| 5,876,447 A | 3/1999 | Arnett |
| 5,980,540 A * | 11/1999 | Bruce ................ A61B 17/8085 606/151 |
| 5,984,925 A | 11/1999 | Apgar |
| 6,068,656 A | 5/2000 | Von Oepen |
| 6,071,291 A | 6/2000 | Forst et al. |
| 6,093,188 A | 7/2000 | Murray |
| 6,117,456 A | 9/2000 | Lee et al. |
| 6,206,957 B1 | 3/2001 | Wenz et al. |
| 6,299,635 B1 | 10/2001 | Frantzen |
| 6,338,810 B1 | 1/2002 | Carpena |
| 6,344,055 B1 | 2/2002 | Shukov |
| 6,364,881 B1 | 4/2002 | Apgar et al. |
| 6,521,246 B2 | 2/2003 | Sapieszko et al. |
| 6,642,285 B1 | 11/2003 | Bohner et al. |
| 6,685,707 B2 | 2/2004 | Roman et al. |
| 6,719,795 B1 | 4/2004 | Cornwall et al. |
| 6,733,582 B1 | 5/2004 | Bohner et al. |
| 6,863,899 B2 | 3/2005 | Koblish et al. |
| 6,905,516 B1 | 6/2005 | Lemaitre et al. |
| 6,991,803 B2 | 1/2006 | Sapieszko et al. |
| 7,118,705 B2 | 10/2006 | Lin |
| 7,175,858 B2 | 2/2007 | Contantz et al. |
| 7,252,841 B2 | 8/2007 | Constantz et al. |
| 7,318,841 B2 | 1/2008 | Tofighi et al. |
| 7,341,601 B2 | 3/2008 | Eisermann et al. |
| 7,351,262 B2 | 4/2008 | Bindseil et al. |
| 7,351,280 B2 | 4/2008 | Khairoun et al. |
| 7,407,542 B2 | 8/2008 | Lemaitre et al. |
| 7,473,312 B2 | 1/2009 | Barralet et al. |
| 7,501,018 B2 | 3/2009 | Engqvist et al. |
| 7,625,399 B2 | 12/2009 | Case et al. |
| 7,655,047 B2 | 2/2010 | Swords |
| 7,682,400 B2 | 3/2010 | Zwirkoski |
| 7,754,246 B2 | 7/2010 | Mosley et al. |
| 7,833,253 B2 | 11/2010 | Ralph et al. |
| 7,927,363 B2 | 4/2011 | Perouse |
| 8,043,382 B2 | 10/2011 | Kumar et al. |
| 8,231,624 B1 | 7/2012 | Strippgen |
| 8,246,663 B2 | 8/2012 | Lovald et al. |
| 8,281,638 B2 | 10/2012 | Metzger |
| 8,287,915 B2 | 10/2012 | Clineff et al. |
| 8,298,292 B2 | 10/2012 | Swords et al. |
| 8,361,126 B2 | 1/2013 | Perrow et al. |
| 8,366,751 B2 | 2/2013 | Pfefferle |
| 8,398,720 B2 | 3/2013 | Swords |
| 8,403,965 B2 | 3/2013 | Henderson et al. |
| 8,435,265 B2 | 5/2013 | Konieczynski et al. |
| 8,556,990 B2 | 10/2013 | Bartee et al. |
| 8,795,377 B2 | 8/2014 | Engqvist et al. |
| 8,834,611 B1 | 9/2014 | Dimicelli |
| 8,906,074 B2 | 12/2014 | Kang et al. |
| 9,023,085 B2 | 5/2015 | Strippgen |
| 9,220,597 B2 | 12/2015 | Engstrand et al. |
| 2001/0011188 A1 | 8/2001 | Berry et al. |
| 2002/0151965 A1 | 10/2002 | Roth |
| 2003/0082232 A1 | 5/2003 | Lee et al. |
| 2003/0199615 A1 | 10/2003 | Chaput et al. |
| 2003/0208262 A1 | 11/2003 | Gaber |
| 2004/0261356 A1 | 12/2004 | Wrass |
| 2005/0149032 A1 | 7/2005 | Vaughen et al. |
| 2005/0216008 A1 | 9/2005 | Zwimmann et al. |
| 2005/0261780 A1 | 11/2005 | Heino et al. |
| 2005/0288790 A1 * | 12/2005 | Swords .............. A61B 17/8085 623/17.19 |
| 2006/0116682 A1 * | 6/2006 | Longo ................ A61B 17/8061 606/280 |
| 2006/0224242 A1 * | 10/2006 | Swords .............. A61B 17/8085 623/17.19 |
| 2006/0235542 A1 | 10/2006 | Hodorek et al. |
| 2006/0239884 A1 | 10/2006 | Chane-Ching et al. |
| 2006/0263443 A1 | 11/2006 | Chow et al. |
| 2006/0271201 A1 * | 11/2006 | Kumar .................... A61L 27/12 623/23.5 |
| 2007/0092856 A1 | 4/2007 | Chow et al. |
| 2007/0112434 A1 | 5/2007 | Hakamatsuka et al. |
| 2007/0156146 A1 | 7/2007 | Metzger et al. |
| 2007/0173844 A1 | 7/2007 | Ralph et al. |
| 2007/0189951 A1 | 8/2007 | Constantz et al. |
| 2007/0233264 A1 | 10/2007 | Nycz et al. |
| 2007/0233272 A1 | 10/2007 | Boyce et al. |
| 2008/0009872 A1 * | 1/2008 | Vaughen ............ A61B 17/8085 606/71 |
| 2008/0027455 A1 | 1/2008 | Bondeville |
| 2008/0028992 A1 | 2/2008 | Lee et al. |
| 2008/0053940 A1 | 3/2008 | Whalen et al. |
| 2008/0187571 A1 | 8/2008 | Clineff et al. |
| 2008/0206300 A1 | 8/2008 | Bohner et al. |
| 2009/0022771 A1 | 1/2009 | Lynn et al. |
| 2009/0076605 A1 * | 3/2009 | Linares ..................... A61F 2/32 623/14.12 |
| 2009/0076617 A1 | 3/2009 | Ralph et al. |
| 2009/0099409 A1 | 4/2009 | Luehrs et al. |
| 2009/0216338 A1 | 8/2009 | Gingras et al. |
| 2009/0220475 A1 | 9/2009 | Bohner et al. |
| 2009/0237880 A1 | 9/2009 | Levesque et al. |
| 2009/0317447 A1 | 9/2009 | Levesque et al. |
| 2010/0095870 A1 | 2/2010 | Insley et al. |
| 2010/0069455 A1 | 3/2010 | Takato et al. |

(56) References Cited

U.S. PATENT DOCUMENTS

| | | |
|---|---|---|
| 2010/0069913 A1 | 3/2010 | Chirico et al. |
| 2010/0094428 A1 | 4/2010 | Ralph et al. |
| 2010/0269736 A1 | 10/2010 | Chow et al. |
| 2010/0303888 A1 | 12/2010 | Barralet et al. |
| 2011/0014244 A1 | 1/2011 | Sapieszko et al. |
| 2011/0054540 A1 | 3/2011 | Ralph et al. |
| 2011/0152195 A1 | 6/2011 | O'Mahony et al. |
| 2011/0158963 A1 | 6/2011 | Font Perez et al. |
| 2011/0218626 A1 | 9/2011 | Krinke et al. |
| 2012/0058152 A1 | 3/2012 | Garcia de Castro Andrews et al. |
| 2012/0165957 A1 | 6/2012 | Everland et al. |
| 2012/0226320 A1 | 9/2012 | Kang et al. |
| 2012/0265312 A1 | 10/2012 | Burke et al. |
| 2012/0271418 A1 | 10/2012 | Hollister et al. |
| 2012/0289964 A1* | 11/2012 | Nakaji ............... A61B 17/1695 606/80 |
| 2012/0310365 A1 | 12/2012 | Chaput et al. |
| 2012/0330435 A1* | 12/2012 | Engqvist ............ A61B 17/8085 623/23.61 |
| 2013/0012942 A1* | 1/2013 | Nelson ............... A61B 17/7208 606/63 |
| 2013/0053900 A1 | 2/2013 | Qwarnstrom et al. |
| 2013/0066325 A1 | 3/2013 | Engqvist et al. |
| 2013/0138114 A1 | 5/2013 | Lin et al. |
| 2013/0158670 A1 | 6/2013 | Tigno, Jr. |
| 2014/0027333 A1 | 1/2014 | Pawlowski et al. |
| 2014/0172116 A1 | 6/2014 | Maxson et al. |
| 2014/0206273 A1 | 7/2014 | Larsen et al. |
| 2014/0228969 A1 | 8/2014 | Engstrand et al. |
| 2014/0243993 A1 | 8/2014 | Barrett et al. |
| 2014/0288650 A1 | 9/2014 | Hunt |
| 2014/0316472 A1* | 10/2014 | Rise ................... A61B 17/8085 606/281 |
| 2015/0105806 A1 | 4/2015 | Dorafshr et al. |
| 2015/0374497 A1 | 12/2015 | Engstrand et al. |
| 2018/0271659 A1* | 9/2018 | Mansmann ......... A61F 2/30756 |
| 2019/0133783 A1* | 5/2019 | Unger ................ A61F 2/30771 |

FOREIGN PATENT DOCUMENTS

| | | |
|---|---|---|
| CN | 101360461 A | 2/2009 |
| CN | 101528158 A | 9/2009 |
| DE | 29913334 U1 | 9/1999 |
| EP | 543765 A1 | 5/1993 |
| EP | 544384 B1 | 1/1996 |
| EP | 433852 B1 | 3/1996 |
| EP | 433852 B2 | 3/1996 |
| EP | 1023032 B1 | 1/2002 |
| EP | 910993 B1 | 7/2002 |
| EP | 936929 B1 | 6/2004 |
| EP | 1380313 B1 | 5/2005 |
| EP | 1178847 B1 | 1/2007 |
| EP | 1905368 A1 | 4/2008 |
| EP | 1420725 B1 | 8/2008 |
| EP | 1958580 A1 | 8/2008 |
| EP | 2014258 A1 | 1/2009 |
| EP | 2030596 A1 | 3/2009 |
| EP | 1298103 B1 | 5/2011 |
| EP | 2474286 A1 | 7/2012 |
| EP | 2529702 A1 | 12/2012 |
| JP | 1-100049 A | 4/1989 |
| JP | 2-143945 U | 12/1990 |
| JP | 2006-218050 A | 8/2006 |
| JP | 2007/501054 A | 1/2007 |
| WO | 95/20368 A1 | 8/1995 |
| WO | 02/11781 A1 | 2/2002 |
| WO | 02/22045 A1 | 3/2002 |
| WO | 03/007831 A1 | 1/2003 |
| WO | 984745 B1 | 10/2003 |
| WO | 2004/093734 A2 | 11/2004 |
| WO | 2004/108019 A2 | 12/2004 |
| WO | 2004/112859 A1 | 12/2004 |
| WO | 2005/016616 A1 | 2/2005 |
| WO | 2005/074453 A2 | 8/2005 |
| WO | 2005/077049 A2 | 8/2005 |
| WO | 2005-122956 A2 | 12/2005 |
| WO | 2007/047921 A2 | 4/2007 |
| WO | 2008/002595 A2 | 1/2008 |
| WO | 2009/077210 A1 | 6/2009 |
| WO | 2010/055483 A2 | 5/2010 |
| WO | 2010/092001 A1 | 8/2010 |
| WO | 2011/009635 A1 | 1/2011 |
| WO | 2011/068451 A2 | 6/2011 |
| WO | 2011112145 A1 | 9/2011 |
| WO | 2012/016200 A1 | 2/2012 |
| WO | 2012/103164 A1 | 8/2012 |
| WO | 2012/118843 A1 | 9/2012 |
| WO | 2012/147114 A1 | 11/2012 |
| WO | 2014091469 A1 | 6/2014 |
| WO | 2014-125381 A2 | 8/2014 |

OTHER PUBLICATIONS

Xu et al. Journal of Materials Science; Materials in Medicine, 18(7); 1345-1353 (2007).

Barralet et al, J. Biomaterials, 25(11);2197-2203 (2004).

Habraken et al, Advance Drug Delivery Reviews, 59(4-5);234-248 (2007).

Han et al. Acta Biomaterialia, 5;3165-3177 (2009).

Desai et al. Advances in Bioceramics and Biocomposites II, Ceramic Engineering and Science Proceedings, vol. 27, Issue 6, Wereszczak et al, Editor, Wiley, pp. 61-69 (Nov. 2006).

Hirayama et al. Journal of Research of the National Institute of Standards and Technology, 113(6);311-320 (2008).

\* cited by examiner

FIG. 5
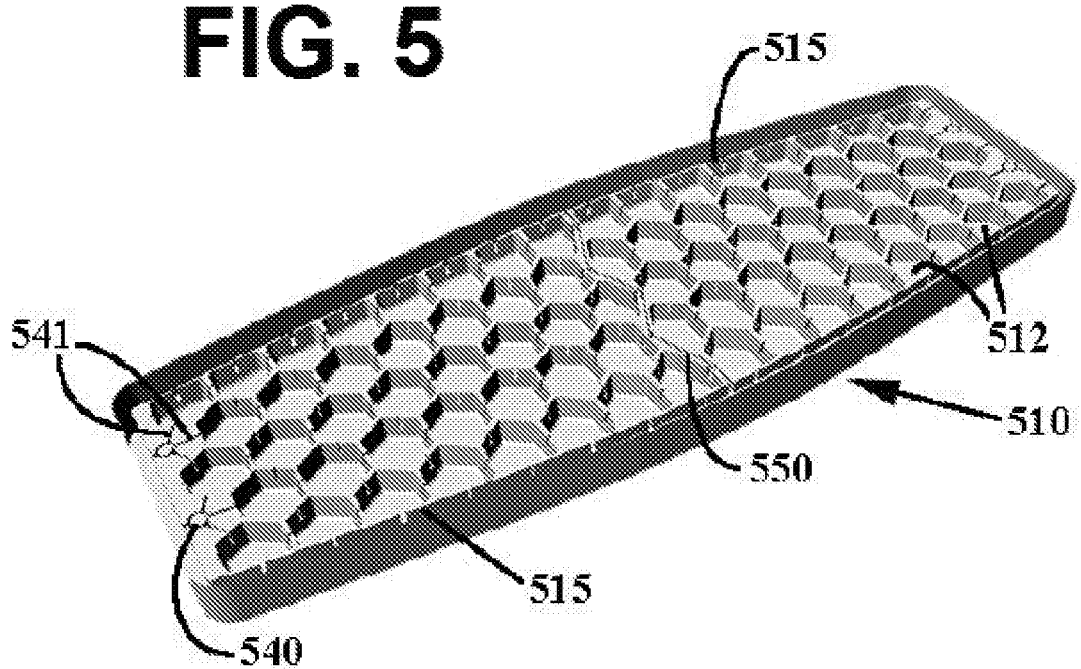
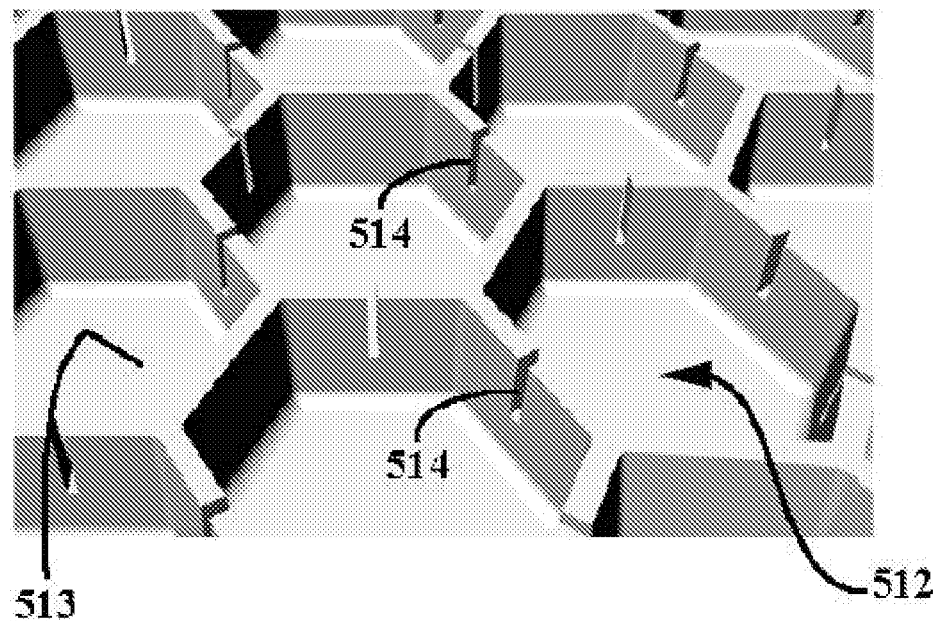
FIG. 6

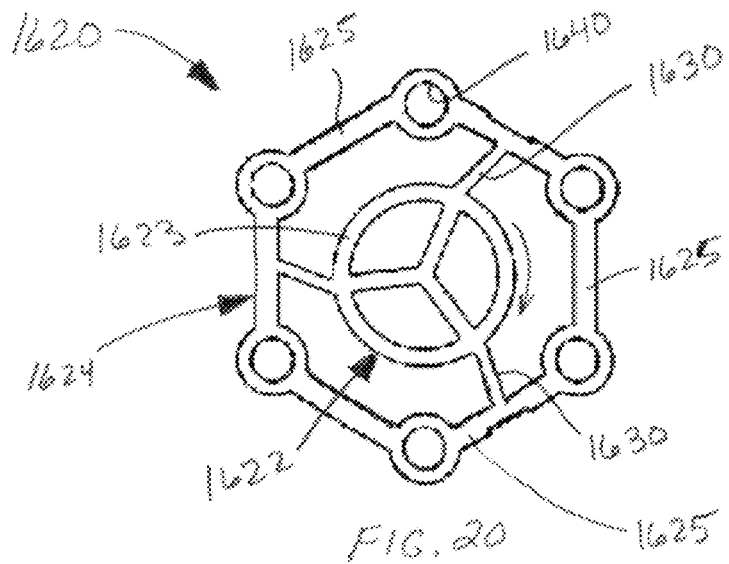
FIG. 20
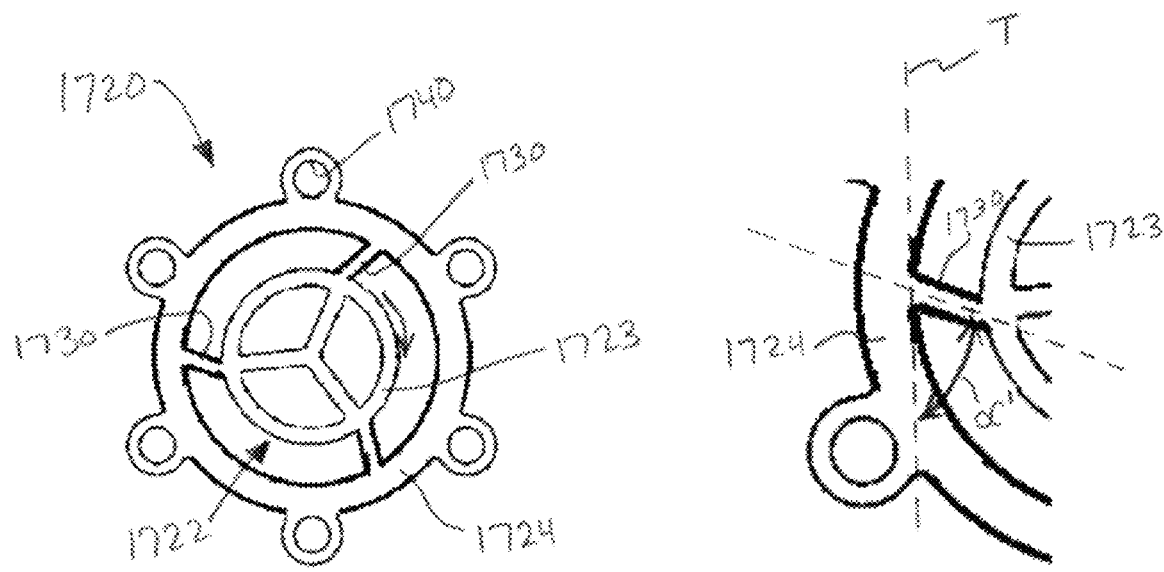
FIG. 21
FIG. 22

BONE IMPLANTS FOR CORRECTING BONE DEFECTS

CROSS REFERENCE TO RELATED APPLICATIONS

This application claims priority to U.S. Provisional Patent Application No. 62/037,595, filed on Aug. 14, 2014, entitled "MOSAIC IMPLANTS, KITS AND METHODS FOR CORRECTING BONE DEFECTS." The entire disclosure of the foregoing provisional patent application is incorporated by reference herein.

BACKGROUND

Bone tissue defects that cannot adequately heal via tissue regeneration often can be filled using autograph, allograph or synthetic scaffold materials. For large defects such as defects in the cranium or long bones, healing can be especially difficult. As a result, various scaffold strategies have been developed which utilize metal meshes or various porous ceramic materials that provide structural support for new tissue (e.g., bone). Many current strategies using metal mesh alone can be problematic due to low new bone formation and/or infections. Many currently used ceramic materials are mechanically weak and fragile, leading to a high risk of scaffold failure.

One advantage of metal meshes is that they often can be shaped to closely fit the defect. Ceramic scaffolds, on the other hand, typically cannot be shaped after manufacturing and therefore have to be custom made in advance. In an attempt to overcome the problem of low bone in-growth with metal meshes, coating the mesh with hydroxylapatite powder has been proposed, particularly for use in revision surgery in joint replacement.

A more recent approach is described in PCT Pub. No. WO 2011/112145 A1, entitled Implants and Methods for Correcting Tissue Defects, published Sep. 15, 2011 (hereinafter, "the '145 App."). Further approaches are described in PCT Pub. No. WO 2014/125381 A2, entitled Mosaic Implants, Kits and Methods for Correcting Bone Defects, published Aug. 21, 2014 (hereinafter, "the '381 App."). The foregoing published applications are incorporated herein by way of reference. The '145 and '381 Apps. describe mosaic implants which comprise a plurality of biocompatible mosaic plates which are connected by a wire (e.g., wire mesh) anchoring arrangement.

While a variety of devices and techniques may exist for correcting bone defects, it is believed that no one prior to the inventors has made or used an invention as described herein.

BRIEF DESCRIPTION OF THE DRAWINGS

While the specification concludes with claims that particularly point out and distinctly claim the invention, it is believed the present invention will be better understood from the following description of certain examples taken in conjunction with the accompanying drawings. In the drawings, like numerals represent like elements throughout the several views.

FIG. 5 depicts a perspective view of a mold suitable for forming the implant section of FIG. 1.

FIG. 6 depicts an enlarged view of a portion of the mold of FIG. 5.

FIG. 20 depicts a top plan view of an alternative embodiment of a support frame for an implant suitable for use, for example, as a bore hole implant in a skull.

FIG. 21 depicts a top plan view of yet another alternative embodiment of a support frame for an implant suitable for use, for example, as a bore hole implant in a skull.

FIG. 22 depicts an enlarged portion of the implant of FIG. 21.

Figure 1:
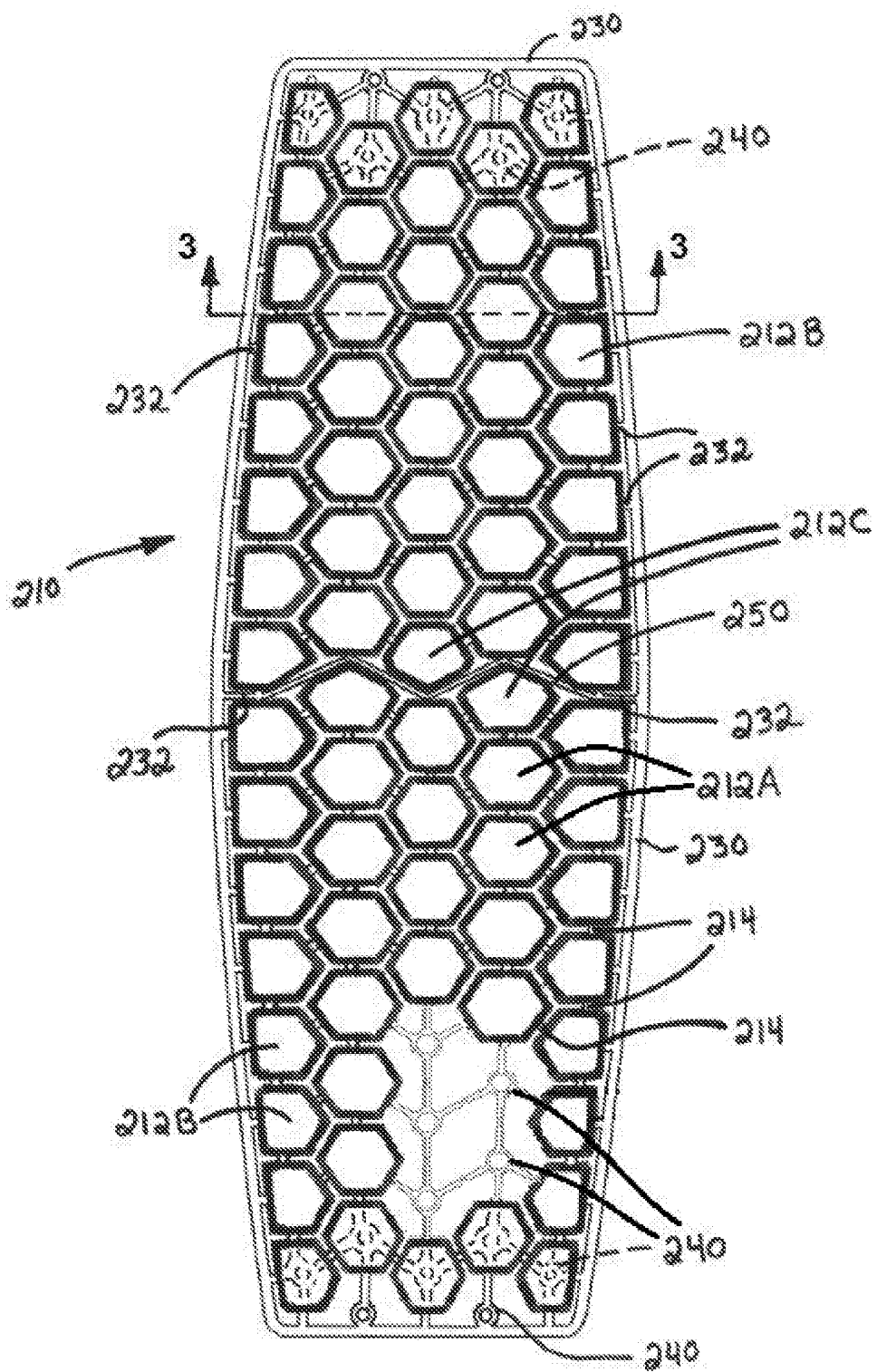
FIG. 1 depicts a top plan view of one embodiment of an implant section, wherein a portion of the mosaic plates have been removed in order to show additional aspects of the wire mesh support frame, and further wherein the implant section of FIG. 1 has tapered sides such that the width of the implant section is widest at its center.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description. As will be realized, the versions described herein are capable of other different and obvious aspects, all without departing from the invention. Accordingly, the drawings and descriptions should be regarded as illustrative in nature and not restrictive.

Examples described herein relate to implants for use in correcting various bone defects, such as implants for use in cranioplasty procedures. In some embodiments, the implants include a plurality of biocompatible mosaic plates that are interconnected with one another by a plurality of wires extending between adjacent plates. Other embodiments comprise implants for use in, for example, as a bore hole implant in a skull, and therefore comprise a single biocompatible plate having a support frame for securing the implant in a bore hole. Embodiments of the implants described herein also include retention features such as a plurality of eyelets located about the periphery of the implant through which fasteners (e.g., bone screws) may be driven into bone surrounding a defect.

In some instances, the implants are configured such that the implant may be cut to various sizes while still providing the retention features about the periphery of the implant. In this manner, an implant comprising a plurality of biocompatible mosaic plates interconnected with one another by a plurality of wires extending between adjacent plates is fabricated in a predetermined configuration that is not specific to a defect in a particular patient. Thereafter, the implant is sized and shaped (e.g., deformed into a curved shape corresponding to the shape of the defect, and/or cut to size) according to the needs of a particular patient. In other embodiments, an implant comprises two or more implant sections that are coupled to one another in order to form an implant.

In alternative embodiments, an implant ready for implantation in a patient comprises a single section of interconnected mosaic plates, wherein the implant has been custom fabricated for the needs of that patient. In these embodiments, little or no modification (e.g., cutting and/or deformation) of the implant is necessary prior to implantation. Such implants are fabricated as rigid structures, wherein, in some embodiments, at least a portion of the implant comprises a curved surface (e.g., a spherical, spheroidal, cylindrical, etc. surface). In this manner, for example, the upper and lower surfaces of the mosaic plates can be fabricated to have a generally curviplanar surface (with small gaps between adjacent plates). The implant is shaped at the time of fabrication, thus avoiding the need to shape the implant immediately prior to implantation in a patient (e.g., in an operating room).

In the case of implants configured for use in bore holes and the like, in some embodiments external portions of the support frame (i.e., portions not located within the biocompatible plate) can be adjusted (e.g., bent or otherwise deformed) in order to match the shape of the patient's bone surrounding the bore hole.

As used herein, the term "wire" refers to a strand, rod, strut, or similar structure having a length that is relatively long compared to its width and thickness, regardless of cross-sectional shape. For example, a "wire," as used herein, can have a circular, oval, rectangular, or other cross-sectional shape. In some of the embodiments described herein, some of the wires of the implants do not have a constant width and/or thickness along their entire length, and may have segments or regions that are irregular in shape. For example, some wires may have a pleated or crimped segment that allows the effective length of the wire to be elongated or shortened, while others have segments of reduced width and/or thickness to provide regions of greater flexibility. In other embodiments, one or more wires have segments of increased width and/or thickness in order provide greater rigidity and/or support to the implant. An individual wire may be in the form of a single, continuous structure, or a plurality of individual filaments or strands may be combined to form a wire (e.g., wrapped or braided).

The wires may be made from any of a variety of biocompatible materials suitable for implantation in a patient, such as various metals, polymers, or even composite materials of two or more metals and/or polymers. Non-limiting examples include biocompatible polymers such as polycaprolactone, shape memory alloys such as nitinol, titanium, titanium alloys (e.g. Ti-6Al-4V) and stainless steel. The wires may also be formed in any of a variety of manners such as forging, casting, molding, extrusion, cutting, etching, stamping, additive manufacturing techniques such as selective laser melting or selective laser sintering), etc. In certain embodiments described further herein, the wires which interconnect the mosaic plates are formed from a metal sheet (e.g., titanium or titanium alloy) which is stamped or cut (e.g., using an automated laser cutting device) in a predetermined pattern to produce a unitary mesh of connected wires having a wire rim extending about at least a portion of its periphery.

FIG. 1 depicts an exemplary mosaic implant sections (210), as further described in the '381 App. Implant section (210) may be used either individually or in combination with one more similarly configured implant sections (10, 110, 220) (see FIG. 2) in the repair of bone and other tissue defects in mammals (including human patients), and is deformable immediately prior to implantation. For example, as described in the '381 App., two or more of mosaic implant sections (10, 110, 210), either identical sections or any combination of different sections, may be coupled together to provide a single implant. Any number of shapes and sizes of mosaic implant sections may be provided, and the three shown are merely exemplary of three possible configurations.

Whether used singly or in a combination of two or more implant sections coupled to one another, the resulting mosaic implant is conformable to various curved shapes in order to match that of a patient's bone defect. In one embodiment, by providing a plurality of differently shaped, sized and/or configured mosaic implant sections (10, 110, 210), such as in the form of a kit, two or more implant sections may be selected and coupled together to provide an implant which is sized and configured for a particular patient. For example, the resulting implant comprising two or more of mosaic implant sections (10, 110, 210) may be configured to match a particular patient's cranial defect in terms of size, shape (e.g., perimetral shape) and, in some instances, curvature. In other instances, a single implant section (10, 110, 210), optionally cut to size and shape as necessary, will be suitable for a relatively small defect in a patient.

Figure 2:
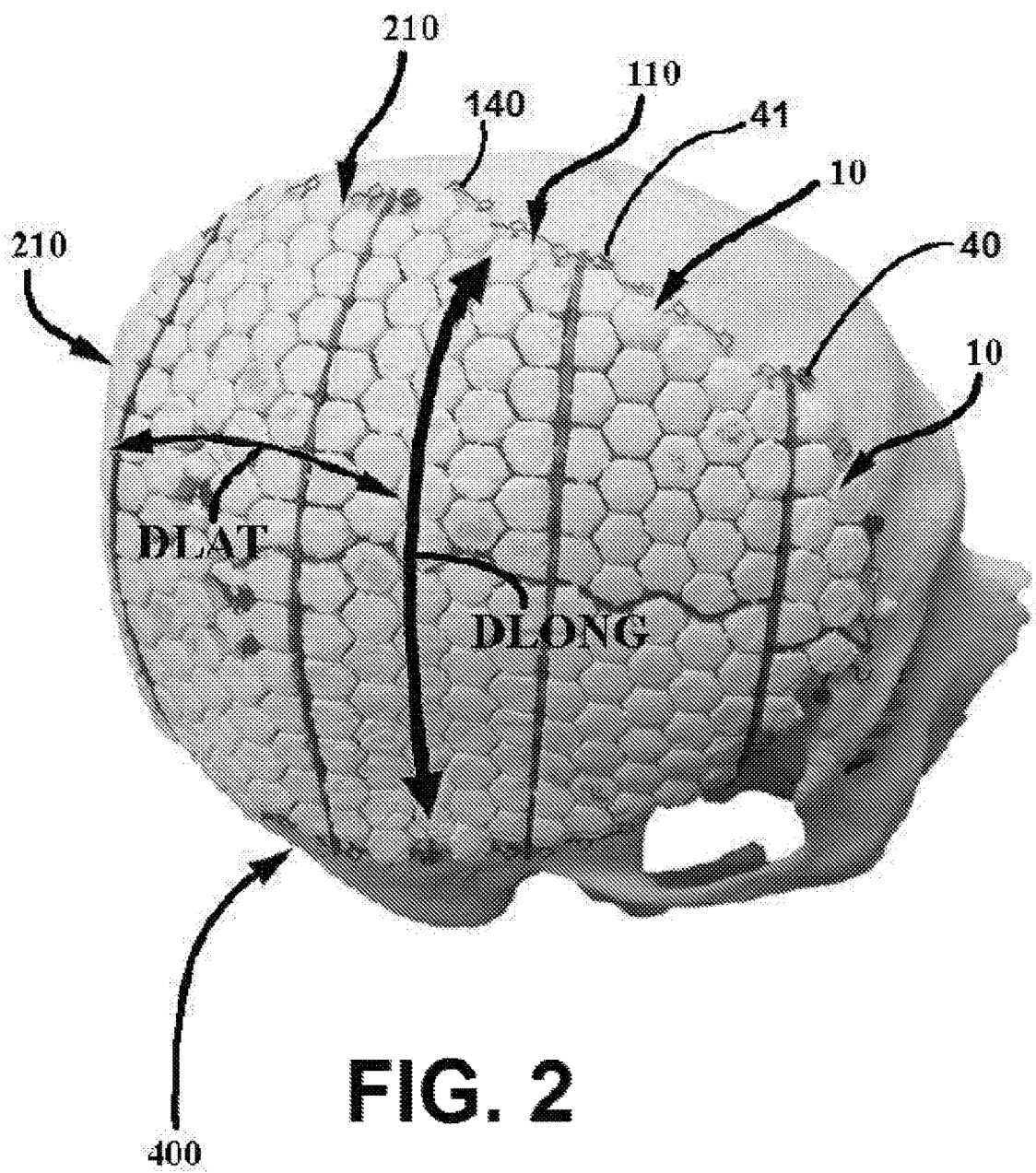
FIG. 2 shows an implant fabricated from the implant section of FIG. 1 as well as modified versions of the implant section of FIG. 1, simulating the implant secured to a patient's cranium over the area of a defect.

By way of one specific example, FIG. 2 depicts an exemplary mosaic implant (400) implanted in a skull having a very large defect. In this illustration, a large portion of the skull is missing as the result of, for example, trauma. Mosaic implant (400) comprises five implant sections (10, 110, 210) that have been coupled together along their adjacent sides. Each of the implant sections also has been trimmed in length. In this manner, implant (400) is sized and shaped to correspond to the patient's bone defect. As also shown in FIG. 2, implant (400) is shaped so that it generally conforms to a curved surface corresponding to the typical shape of the missing portion of patient's cranium. In other words, implant (400) has been shaped (i.e., deformed) to match the patient's cranial shape. Such shaping not only helps to ensure the maintenance of sufficient cranial volume upon bone in-growth and implant resorption, but also provides a cosmetically pleasing appearance.

Implant (400) can be attached to host tissue (e.g., the patient's cranial bone about the perimeter of a defect) via sutures, plates, screws, clamps and/or any of a variety of other fasteners or fixation devices. In FIG. 2, implant (400) is attached to the surrounding cranial bone using a plurality of screws (e.g., titanium bone screws) inserted through retention eyelets (40, 140, 240) located along portions of the periphery of the implant sections (10, 110, 210), as described further herein.

Returning to FIG. 1, implant section (210) comprises a plurality of biocompatible mosaic plates (212) which are interconnected with one another by a plurality of wires (214). Each mosaic plate (212) is connected to a plurality of the immediately adjacent mosaic plates by the wires (214) that extend between and into the adjacent connected plates (212). In general, each plate (212) (or at least a majority of the plates of an implant section) is connected to two or more adjacent plates by the wires (214).

The wires (214) may be configured such that separate, non-intersecting, non-connected wires extend between adjacent plates. In other embodiments, wires (214) comprise an arrangement of crossing wires which may or may not be connected to each other, as described in the '145 App. In yet another embodiment, and as shown in FIG. 1, wires (214) are integrally formed with one another such as by cutting (e.g., laser cutting), etching or stamping a flat sheet in order to provide wires (214) in the form of wire segments connected to one another via retention eyelets (240) so as to provide wire mesh. As used herein, a "mesh" comprises an arrangement of wires wherein at least two crossing wires are joined at one, some, or all of their intersections, or wherein wire segments (e.g., wires (214) are joined to one another (e.g., via eyelets (240) such that open regions are located between and bounded by adjacent wires. In the embodiment shown in FIG. 4, the open regions between and bounded by adjacent wires (214) have the shape of a parallelogram. It will be understood, however, that any of a variety of other mesh arrangements may be employed, as further described herein.

Biocompatible mosaic plates (212) can be composed of any of a variety of resorbable and/or stable (i.e., non-resorbable) biocompatible materials, including various types and/or combinations of polymers, ceramics and metals. In some embodiments, the plates are composed of an osteoconductive and/or osteoinductive material. Osteoconductive materials serve as a scaffold on which bone cells will attach, migrate, and grow and divide so as to form new bone on the surfaces of the plates (212). Osteoinductive materials induce new bone formation around the plates (212). In the embodiments described herein, having the plates (212) arranged such that a gap is provided between adjacent plates, osteoconductive and/or osteoinductive mosaic plates will facilitate bone growth onto and between the plates of the implant, since the gaps allow for the free circulation of blood and tissue fluids between the plates.

In some embodiments, biocompatible mosaic plates (212) are composed of a moldable bioceramic or biopolymer material. While bioceramic materials can be produced by sintering ceramic powders, it can be difficult to produce complex shapes in this manner. Alternatively, bioceramics can be formed by a chemical bonding route whereby the ceramic material is formed by chemical reaction, such as a cement setting and hardening reaction.

In some embodiments of the present, a hydraulic cement composition is used to mold the biocompatible plates. Non-limiting examples include cement precursor compositions comprising one or more Ca-salts such as calcium sulfates, calcium phosphates, calcium silicates, calcium carbonates and combinations thereof. As further described herein, the biocompatible plates are formed by molding the cement composition around portions of the wires (214). For example, a powdered cement precursor composition is combined with either a non-aqueous water-miscible liquid or a mixture of water and a non-aqueous water-miscible liquid. The mixture is then poured or injected into a mold having the wires (214) positioned therein, and allowed to harden (e.g., in a water-containing bath) so as to form the mosaic plates (212) interconnected to one another by the plurality of wires (214).

Various cement compositions that may be used to mold mosaic plates (210) are described, for example, in PCT Pub. No. WO 2014/091469 A1, published Jun. 19, 2014, titled "Cement-Forming Compositions, Monetite Cements, Implants and Methods for Correcting Bone Defects." Alternative cement compositions for use in molding the plates, including storage stable premixed hydraulic cement compositions, are described in PCT Pub. No. WO 2013/035083 A2, published Mar. 14, 2013, titled "Storage Stable Premixed Hydraulic Cement Compositions, Cements, Methods, and Articles." Still further cement compositions which may be used to mold the plates (12, 112, 212) are described, for example, in the '145 App., as well as PCT Pub. No. WO 2013/027175 A2, published Feb. 28, 2013, titled "Implants and Methods for Using the Implants to Fill Holes in Bone Tissue," and PCT Pub. No. WO 2010/055483 A2, published May 20, 2010, titled "Hydraulic Cements, Methods and Products." Each of the foregoing patent applications and publications is incorporated by reference herein.

In one embodiment, the compositions are calcium phosphate cement-forming compositions that comprise a monetite-forming calcium-based precursor powder and a non-aqueous water-miscible liquid. In one specific embodiment, the monetite-forming calcium-based precursor powder comprises monocalcium phosphate (monocalcium phosphate monohydrate (MCPM) and/or anhydrous monocalcium phosphate (MCPA)) and β-tricalcium phosphate in a weight ratio of 40:60 to 60:40, and from 2 to 30 weight percent, based on the weight of the precursor powder, of dicalcium pyrophosphate powder (also referred to herein as calcium pyrophosphate). The powder to liquid (wt/vol) ratio in the composition is from 2 to 6 g/ml.

In another embodiment, the compositions are calcium phosphate cement-forming compositions that comprise a monetite-forming calcium-based precursor powder and are adapted to be mixed with an aqueous liquid or exposed to an aqueous liquid to achieve hardening. In one specific embodiment, the monetite-forming calcium-based precursor powder comprises monocalcium phosphate (monocalcium phosphate monohydrate (MCPM) and/or anhydrous monocalcium phosphate (MCPA)) and β-tricalcium phosphate in a weight ratio of 40:60 to 60:40, and from 2 to 30 weight percent, based on the weight of the precursor powder, of dicalcium pyrophosphate powder (also referred to herein as calcium pyrophosphate).

The porosity of the molded plates (212) may also be controlled, as the porosity affects bone in-growth and the resorption time in vivo. For example, porosity may be controlled by controlling monocalcium phosphate particle size in the precursor composition, and/or adding one or more porogens to the precursor composition. In some embodiments, the molded plates have a porosity of from 40 to 50%, and in other embodiments the porosity is about 46%.

In one specific embodiment, the monetite-forming calcium-based precursor powder mixture is mixed with a non-aqueous water-miscible liquid such as glycerol, optionally including up to 20% water (based on the total liquid volume). After mixing, the precursor mixture is injected into a mold having the wires (214) positioned therein, with portions of each wire extending into and between the mold cavities which are shaped to form the mosaic plates (212). The filled mold is then exposed to water, such as by placing the mold in a water bath, and the cement is allowed to harden (e.g., 24 hours in a room temperature water bath). The implant section (210) is then removed from the mold. Further processing such as soaking the implant section in water to remove glycerol residues may be performed, as necessary.

The thus-formed mosaic plates (212) in the example described above will comprise monetite ($CaHPO_4$) and 2-30 wt. % dicalcium pyrophosphate, along with varying amounts of other materials such as β-tricalcium phosphate and minor amounts of brushite ($CaHPO_4.2H_2O$) (e.g., less than 2 wt. % or less than 1 wt. %). The mosaic plates (212) in some embodiments comprise at least 65 wt %, at least 70%, at least 75%, at least 80%, at least 85%, or at least 90% monetite. The presence of dicalcium pyrophosphate not only delays resorption of the mosaic plates but also provides osteoinductivity (i.e., promotes new bone growth around and between the mosaic plates as compared to similar monetite formulations which do not include dicalcium pyrophosphate).

Each mosaic plate (212) may have any of a variety of shapes, such as triangles, circles, squares, rectangles, pentagons, hexagons, or other polygons. The shape of each plate may be regular (e.g., a pentagon or hexagon having sides of equal length) or irregular. In addition, the plates (212) of an implant section (210) may have the same or different shapes, regular and/or irregular. In some embodiments, the plates (212) have identical shapes (e.g., regular hexagons, squares or rectangles) and are arranged in a pattern such that each side edge of a plate is spaced apart from an edge of an immediately adjacent plate by the same (or nearly the same) amount so that a consistent gap is provided between adjacent plates. In other instances, there may be regions of the implant section (210) whereat the gap between adjacent plates is larger, for any of a variety of reasons (e.g., to accommodate a support structure). In the event that the mosaic plates of an implant section do not all have identical shapes, adjacent plates may nevertheless have complementary shapes such that the plates are arranged in a pattern with no overlap of plates and substantially equal gaps between adjacent plate edges. In the specific embodiment shown in FIG. 1, the implant section (210) includes both hexagonal (212A) and pentagonal plates (212B).

A wire rim (230) extends about the entire periphery of the implant section (210), and is connected to plates (212B) as well as a support girder (250) via wire struts (232) which extend between the rim (230) and outer plates (212B) (as well as between the rim and the ends of the support girders).

Mosaic plates (212) may be provided in any of a variety of sizes. As seen in the cross-sectional view of FIG. 3, the sidewalls of the mosaic plates may be sloped or tapered such that the plates are wider at their top surface than at their bottom surface. Alternatively, this sloping or tapering may be configured in a variety of other manners, such as tapering the sidewalls of the mosaic plates from both the top and bottom surfaces so that the plates are widest in cross-section across the center of the plate, or at some other location between the top and bottom surfaces. The sloping or tapering of the sidewalls allows the implant section to be shaped into various curvatures—either at the time of fabrication or by later deformation such as by a surgeon—with a deeper concavity in the bottom surface of the implant without the edges of adjacent mosaic plates coming into contact with each other than would be possible with vertical, non-tapered sidewalls. In order to obtain good aesthetical results, the thickness $T_T$ is as small as possible while maintaining sufficient strength of the plates. In adjusting an implant to a specific defect the thickness $T_T$ can be reduced by polishing or other material removal process, particularly along the periphery of the implant in order to improve implant fit and improve aesthetics (e.g., to provide a smooth, reduced height transition between the surface of surrounding bone and the upper surface of the implant).

In some embodiments, the gap between adjacent edges of plates at the bottom surface of the plates is less than 3 mm, less than 2 mm, or less than 1.2 mm. At the top surface of the plates the gap between adjacent edges of plates is less than 2 mm, or less than 1.4 mm or less than 0.8 mm. A smaller gap facilitates the filling of the gap by new bone growth. It is of course possible to have different sized gaps between cavities if the implant is intended to have regions which will be substantially flat and other regions which will be deformed into various curvatures and shapes.

Figure 3:
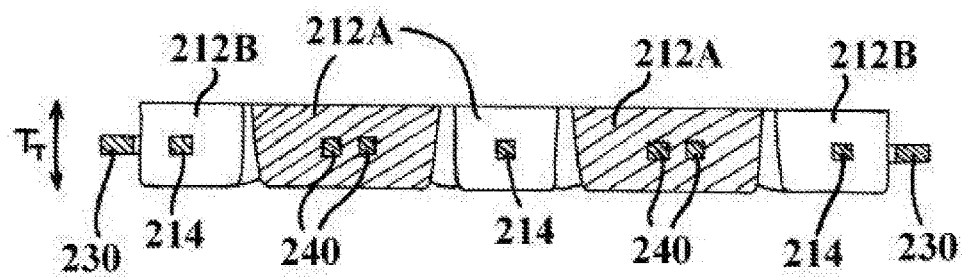
FIG. 3 depicts a cross-sectional view of the implant section of FIG. 1, taken along the line 3-3 thereof.
Figure 4:
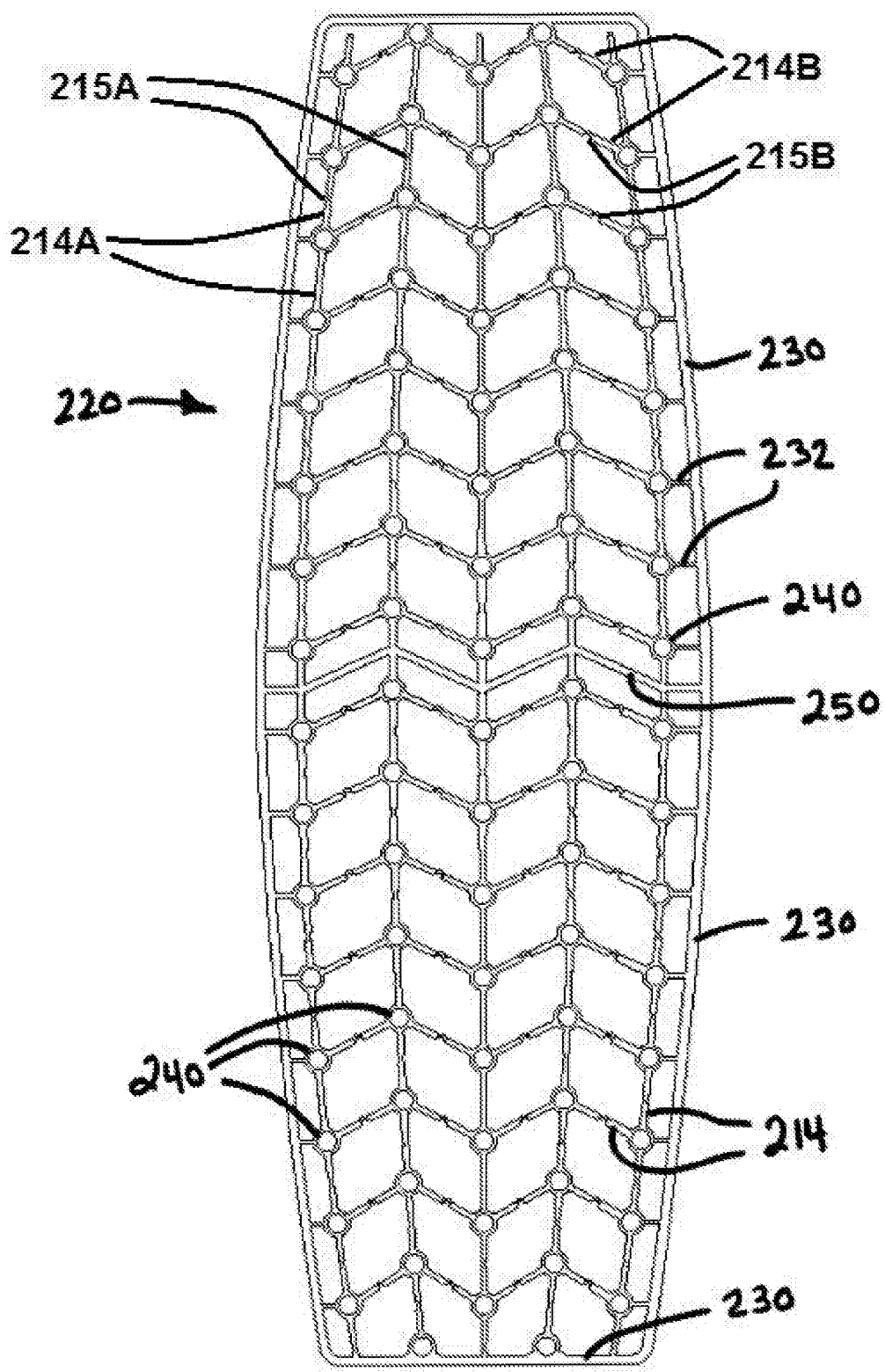
FIG. 4 is a top plan view of the wire mesh support frame of the implant section shown in FIG. 1.

In the embodiment shown in FIGS. 1-4, and as described in the '381 App., the wires (214) are interconnected with one another via retention eyelets (240), some of which are also connected to rim (230) by wire struts (232). The resulting structure is a wire mesh support frame (220) which is bounded about at least a portion of its periphery by rim (230), as shown in FIG. 4. Support frame (220) may be formed in a variety of ways such as by welding wire segments and eyelets to one another in the arrangement shown, or by a molding process. In the embodiments shown in FIG. 4, the components of support frame (220) are integrally formed with one another by cutting (e.g., laser cutting), etching or stamping a flat sheet to form wires (214), eyelets (240), wire struts (232), support girder (250) and rim (230) from a single sheet of material. Any of a variety of materials may be used for support frame (220), such as biocompatible metals, including alloys. In the embodiments shown, support frame (220) is laser cut, using an automated, programmable laser cutting device, from a sheet of titanium or titanium alloy. The titanium or titanium alloy sheet comprises grade 2, 4, 5 or 23 titanium, 0.3-0.6 mm thick. In the embodiment shown, grade 2 titanium, 0.4 mm thick is used. Alternatively, support frame (220) may be cut, etched, stamped, molded or otherwise formed from a biodegradable polymer such as polycaprolactone.

It should be noted that, as used herein, the term "eyelet" means an opening having a substantially closed perimeter, but it is not limited to a particular shape. Thus, eyelets (240) can be round, square, rectangular, trapezoidal, hexagonal, tear-drop, oval, elliptical or any other suitable shape. Of course, other types of attachment apertures or other fastening points may be used in place of, or in addition to the eyelets (240). Each eyelet (240) is positioned so as to be located entirely within the interior of a plate (212), such as approximately in the middle of the plate. In order to provide sufficient strength while also allowing the implant sections to be deformed (i.e., bent, particularly into various curvatures), wires (214) extend away from eyelets (240) so as to span between the adjacent, parallel sides of adjacent plates. Thus, wires (214) intersect the sides of the plates at an angle of approximately 90°.

When the support frame (220) is fabricated from a single sheet of metal, the wires (214), struts (232), eyelets (240), and rim (230) will generally have the same thickness. In the examples shown, the support frame members have a thickness of about 0.4 mm. The rim (230) has a width of 0.4 to 1.6 mm, or from 0.6 to 1.2 mm, or 1.0 to 1.2 mm. Wires (214) have a width of 0.4 to 0.6 mm, wire struts (232) have a width of about 0.45 mm, the interior diameter of eyelets (240) is approximately 2.1 mm, and the width of the metal forming the eyelets is about 0.4 mm.

In order to provide additional shapability to implant sections (210) and an assembled implant (400), the wires (214) include deformation zones. The deformation zones are generally located in the middle of the length of a wire (214) such that they will generally be positioned between adjacent plates so that deformation will occur between the plates so as to prevent cracking of the plates upon deformation of the implant section. The deformation zones can comprise, for example, reduced-width regions (215A) which are located between adjacent plates following molding. When the implant section is longitudinally deformed (i.e., curved about an axis which extends transverse to length L, as indicated by $D_{LONG}$ in FIG. 4), wires (214A) will deform (i.e., bend) at reduced-width regions (215A) so that such deformation is less likely to cause the plates to crack. By way of one example, when wires (214A) have a width of 0.5 to 0.7 mm, reduced-width regions (215A) have a width of 0.3 to 0.5 mm. It should be understood that "transverse" is not intended to mean at an angle of 90 degrees.

Also in the embodiments shown in FIGS. 1-4, wires (214B) have pleated regions (215B) which are also located between adjacent plates following molding. Pleated regions (215B) not only have a reduced width, they also include one or more pleats which allow additional deformation of the implant while avoiding cracking the plates. In particular, pleated regions (215B) facilitate lateral deformation of the implant section (i.e., curving the implant section about an axis that extends transverse to width W, as indicated by $D_{LAT}$ in FIG. 2). Wires (214B) will deform (i.e., bend) at pleated regions (215B) rather than within the plates in order to avoid plate cracking. In addition, pleated regions (215B) also allow the implant section to be locally stretched or compressed in order to further facilitate shaping of the implant to match a patient's defect. It should also be pointed out that although rim (230) generally can only be deformed along its length, struts (232) are deformable along their length. Support girder (250) is deformable in a similar fashion.

When two or implant sections (10, 110, 210) are needed in order to provide an implant (400) corresponding to the shape of a patient's defect, implant sections may be coupled to one another along portions of their rims (230). Such coupling may be accomplished in any or variety of ways, such as using mechanical fasteners, biocompatible adhesives, welding, binding, etc. In the embodiments shown in FIG. 2, the implant sections are coupled to one another by spot welding their overlapping rims. Thus, the rims extending along the sides of adjacent implant sections (10, 110, 210) are positioned in overlapping arrangement and then welded to one another at spot welds (431) along the length of the overlapping rims (see FIG. 2A).

While the deformation of an implant section in either the $D_{LONG}$ or $D_{LAT}$ directions is limited only by the spacing between adjacent plates and the amount of sidewall tapering of the plates, deformation in both the $D_{LONG}$ and $D_{LAT}$ directions is much more limited unless plates are removed. This is a result of the fact that spheres, spheroids and other similarly curved surfaces are not developable. (A "developable surface" is one that that can be flattened onto a plane without the need for any stretching or compression.) One advantage of implant section (210) which has curved rims (230) along its sides is that two implant sections may be attached to one another along their adjacent sides to provide a shape which more closely matches a non-developable curved surface, much in the way that various map projections are used to approximate the curvature of the earth in a flat plane. In addition, when rims (230) of implant sections (210) are coupled to one another, particular when done in an overlapping fashion, the rims of adjacent implant sections provide a beam portion extends across the length of the implant. This beam portion provides additional structural support to the curved implant (400) which resists deformation (e.g., flattening of the curved shape) following implantation in a patient. Similarly, support girder (250) also provides additional structural support across the central region of implant (400), often the most vulnerable area in terms of inward deformation (i.e., flattening or caving-in).

It will be understood that additional structural supports may be provided such as additional support girders extending across the width of an implant section. Similarly, the beam portion extending across a length of the implant may be provided in various alternative ways besides adjoining rims extending along the sides of coupled implant sections. For example, rim (230) itself provides structural support that resists inward deformation of a single implant section (210) which is implanted in a patient. Alternatively, one or more support girders similar to support girder (250) may be provided in the lengthwise direction, particularly in an arrangement wherein the support girder(s) is positioned in a zigzag arrangement between adjacent plates.

Figure 7:
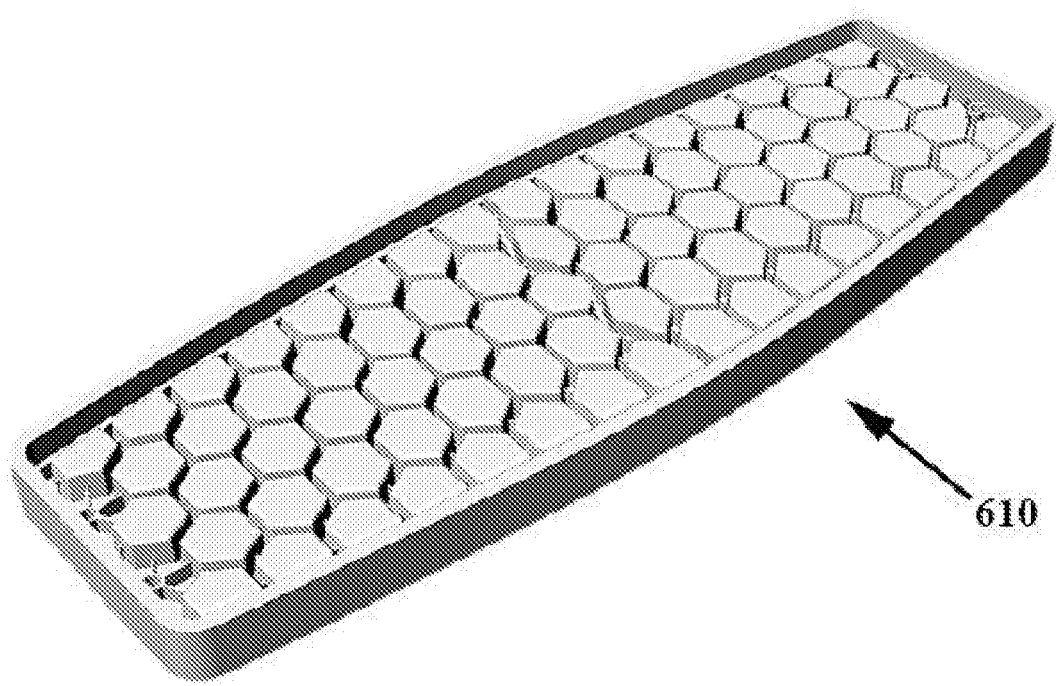
FIG. 7 depicts a perspective view of a negative mold suitable for forming the mold of FIG. 5.

As mentioned previously, implant section (210) may be formed by a variety of processes, such as molding. In the specific embodiments shown, implant section (210) is formed by molding plates (212) about the wires (214) of a support frame (220). One such mold (510) is shown in FIGS. 5 and 6, wherein the mold (510) is configured for use in forming implant section (210). Mold (510) may be formed of any of a variety of materials such as silicone, Teflon, other polymers or metals. Mold (510) includes a plurality of cavities (512) shaped and arranged for forming mosaic plates (212). Thus, cavities (512) have tapered sidewalls corresponding to the tapered sidewalls of the plates, as shown in FIG. 3. The bottom (513) of each cavity (512) corresponds to the bottom surface of a plate (212). FIG. 7 depicts a negative mold (610) which may be used to form mold (510) by a molding process.

Channels (514) are provided in the sidewalls of selected cavities (512). Channels (514) correspond to the locations of wires (214) of support frame (220) and have depth corresponding to the desired depth of the wires (214) in the implant section (210). Thus, channels (514) receive wires (214) therein. Circular cutouts (540) are also provided at the top and bottom ends of the mold to accommodate the eyelets (240) of support frame (220) which are not to be enclosed by plates (212), along with elongate grooves (541) which extend from cutouts (540) to the adjacent cavities (512). Elongate grooves (541) accommodate the wires (214) which extend away from eyelets (240). Similar, groove (550) extends across the width of the mold (510) for accommodating support girder (250) therein.

Prior to molding, a support frame (220) is positioned within mold (510) such that rim (230) extends about outer wall (515) of the mold cavities (512), with wires (214) positioned at the bottom of channels (514) and eyelets positioned within cutouts (540). The positioning of the wires (214) of support frame (220) is controlled by the depth of cutouts (540). Next, the precursor cement composition described previously (or other moldable composition) is inserted into the mold cavities (512) such as by pouring or injecting. While mold (510) does not require a top plate, other embodiments of mold (510) may include a top plate for enclosing the mold either before or after addition of the precursor composition. If the mold is sealed prior to the addition of the cement composition, the mold will include one or more sprues through which the cement may be injected into the mold cavities.

After setting and hardening of the mosaic plate material, the implant section (210) is removed from mold (510). Thereafter, the implant section (210) is cut to the desired length and width, as necessary. For example, as best seen in FIG. 2, the portion of the rim (230) extending across the top and bottom ends of the implant section is cut off along with portions of the rim extending along the sides of the implant section as necessary. In addition, wires (214), particularly longitudinally extending wires (214A), may be cut as necessary, to trim the implant section to the desired length. Similarly, selected ones of laterally extending wires (214B) may be cut as necessary, particularly to trim in implant section to the desired width. Since eyelets (40, 140, 240) are used to secure the implant to bone surrounding a defect, the mosaic plate material along the periphery of the implant is also removed such as by breaking the plates off of the support frame using pliers or other suitable implement in order to expose one or more of the eyelets about the periphery of the implant (400), as also seen in FIG. 2.

Figure 2A:
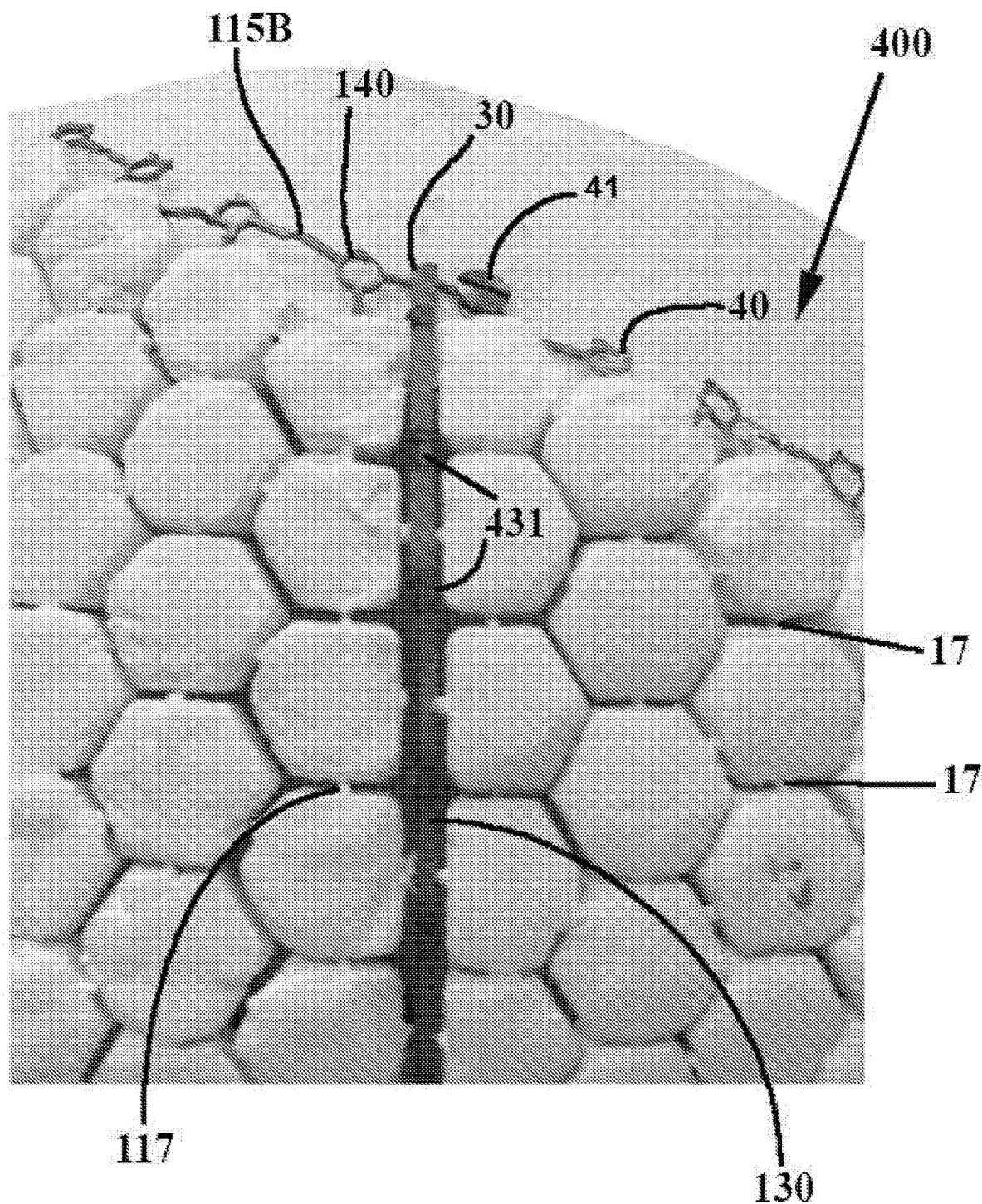
FIG. 2A depicts an enlarged view of a portion of the view shown in FIG. 2.

As also seen in FIGS. 2 and 2A, during molding some cement (17) (FIG. 2A) will set and harden within channels (514), directly above the portions of wires (214) and struts (232) not located within plates (12, 112, 212). The portions of cement (17) covering the wires (214) act as osteoconductive and/or osteoinductive bridges between the cement plates, facilitating the formation and/or growth of new bone between adjacent plates along the wires (214).

As mentioned previously, in adjusting an implant to a specific defect the thickness $T_T$ of the mosaic plates (see FIG. 3) can be reduced by polishing or other material removal process, particularly along the periphery of the implant in order to improve implant fit and/or improve aesthetics. This may also be accomplished by forming the mosaic plates of an implant section to have varying thickness across the mosaic plates and/or across the implant section itself, such as by configuring a mold for the mosaic plates of the implant section accordingly.

Figure 8A:
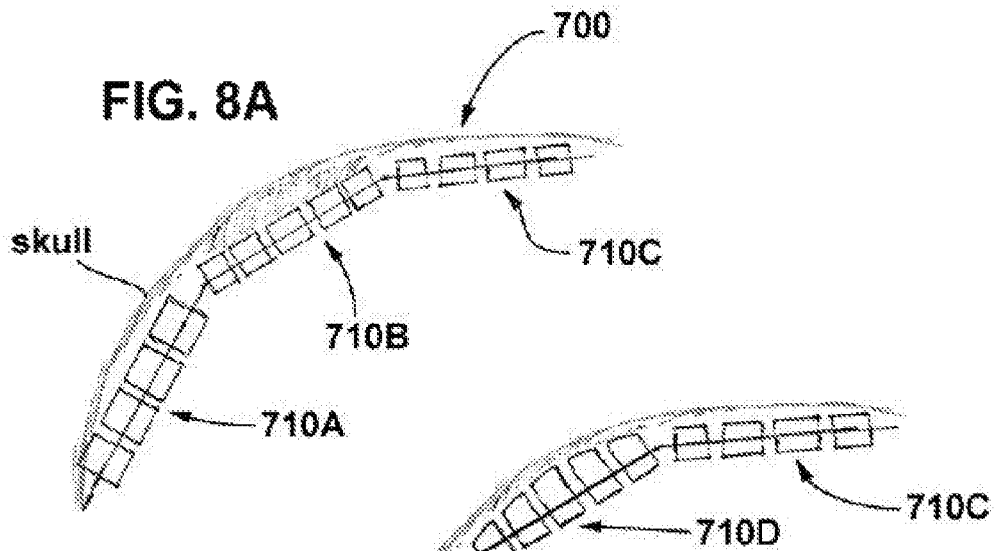
FIG. 8A is a schematic cross-sectional view depicting an implant implanted in a patient's skull.

By way of one specific example, FIG. 8A depicts a schematic cross-sectional view of an exemplary mosaic implant (700) secured to a patient's skull over the area of a very large defect. In this illustration, mosaic implant (700) comprises three implant sections (710A, 710B, 710C) which have been coupled together along their adjacent sides. Implant sections (710A, 710B, 710C) may be configured similarly to any of the implant sections previously described herein. As seen in FIG. 8A, when the surrounding skull or other bone adjacent the implant region has significant curvature, mosaic plates of uniform thickness will often result in implant (700) significantly deviating from the curvature of the skull (i.e., resulting in a flattened appearance in the area of the implant compared to the surrounding bone.

Figure 8B:
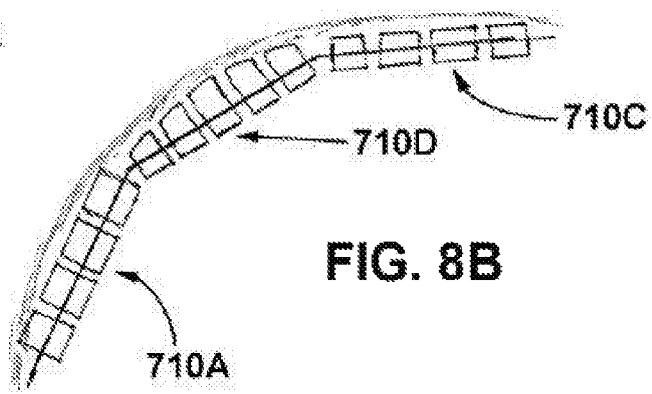
FIG. 8B is a schematic cross-sectional view similar to FIG. 8A, wherein an alternative embodiment of an implant section (710D) has replaced middle implant section (710B) of FIG. 8A.

In order to reduce or eliminate such a flattened region, the thickness of the mosaic plates may vary across the width and/or length of the implant section. In the embodiment shown in FIG. 8B, center implant section (710B) of FIG. 8A has been replaced by an implant section (710D) having mosaic plates which taper in thickness across the width of the implant. Thus, the mosaic plates at the center of the implant section are crowned, as shown, and the mosaic plates on either side thereof taper in thickness as shown. Thus, the mosaic plates of implant section (710D) are thickest at the middle of the implant section and narrowest at the outer sides of the implant section. Of course, it will be understood that the mosaic plates may taper in the lengthwise direction and or in one more other directions so as to better match the shape of the bone surrounding a patient's defect.

Figure 9:
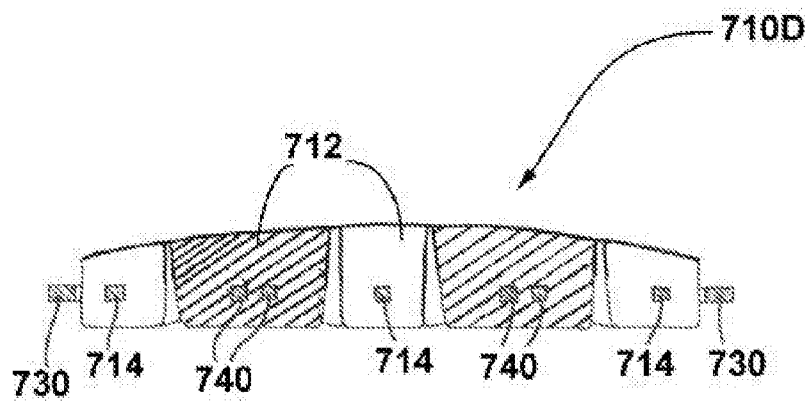
FIG. 9 is a cross-sectional view of the implant section (710D) of FIG. 8B, wherein the cross-sectional view is taken similarly to the cross-sectional view of FIG. 3 (i.e., across the width of the implant section).

FIG. 9 depicts a cross-sectional view of implant (710D), taken along the same line as that shown in FIG. 3. The additional reference numerals in FIG. 9 refer to the same components of like numerals in the preceding implant section embodiments (e.g., eyelet (740) and wires (714)). Thus, apart from the tapered thickness of the mosaic plates (712), the construction of implant section (710D) is the same as implant sections (10, 110, 210).

Figure 10:
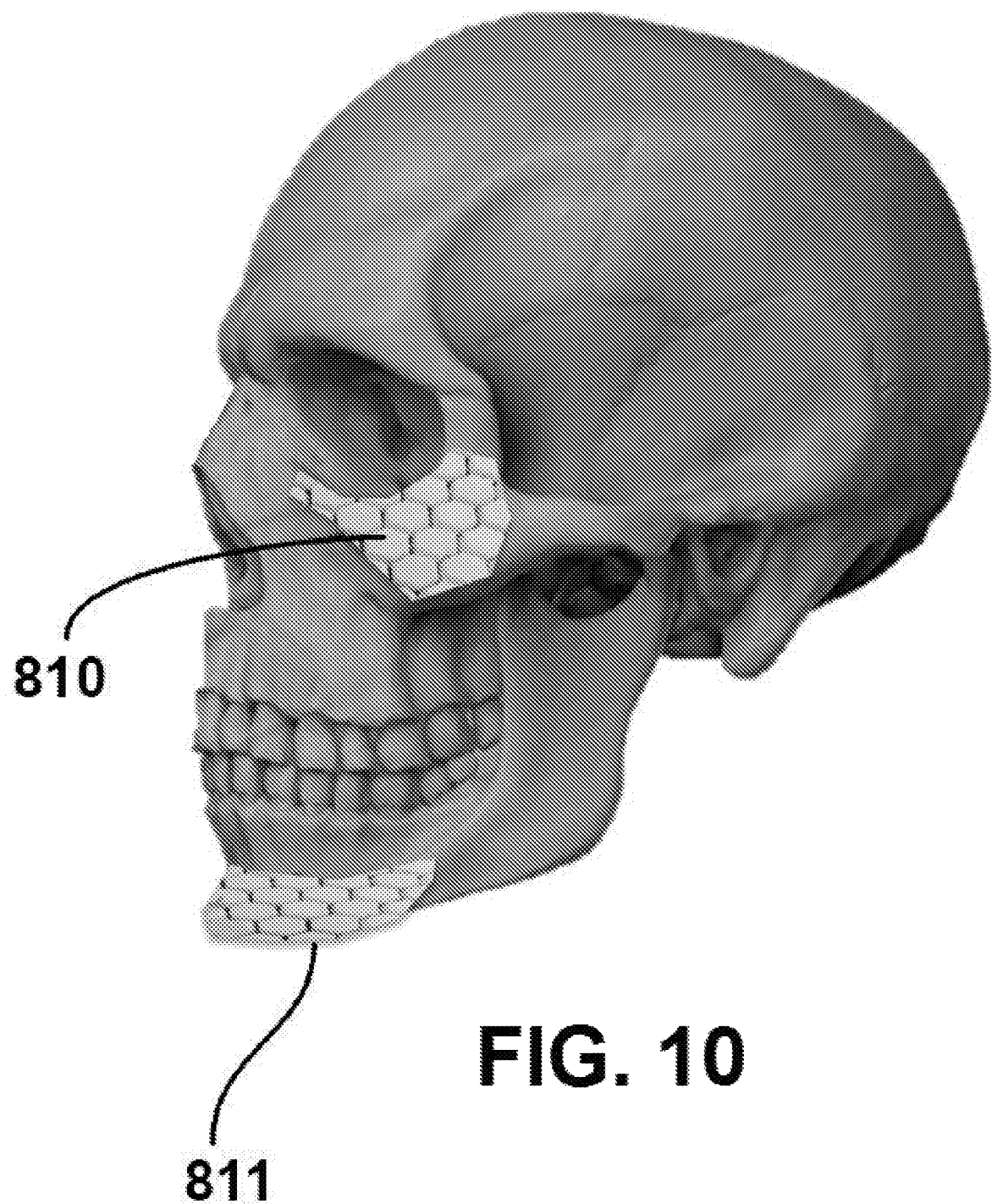
FIG. 10 depicts a mosaic implant (810) positioned over a defect in a patient's zygomatic (cheek) bone, and a second mosaic implant (811) positioned over a defect in a patient's mandible (chin).
Figure 11:
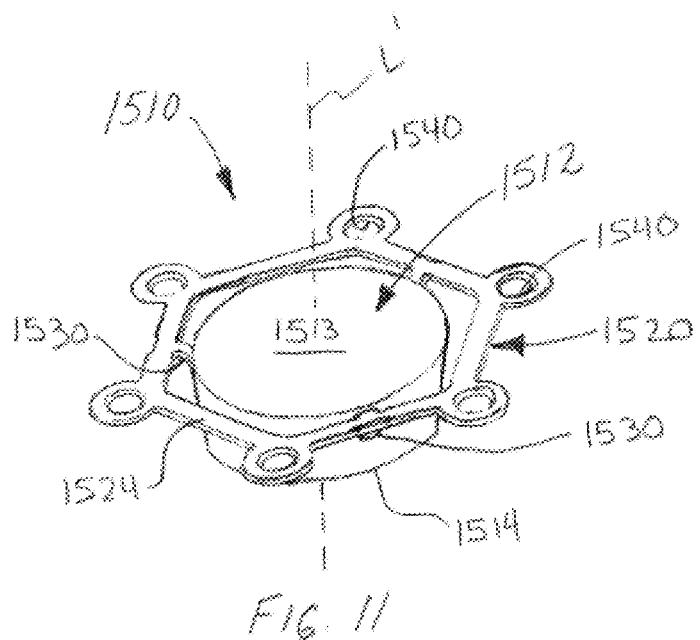
FIG. 11 depicts a perspective view of an alternative embodiment of an implant suitable for use, for example, as a bore hole implant in a skull.
Figure 16:
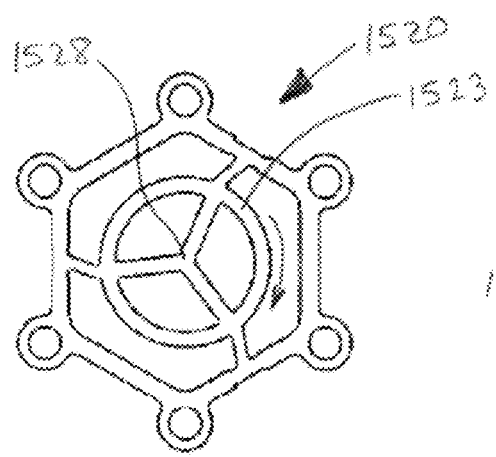
FIG. 16 depicts a top plan view of the support frame of FIG. 14.
Figure 17:
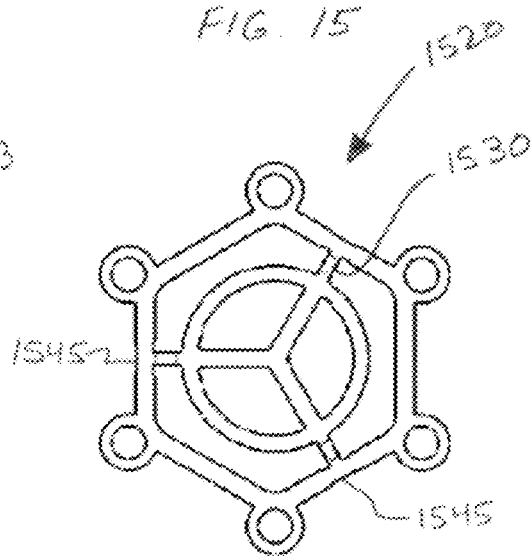
FIG. 17 depicts a top plan view of the support frame of FIG. 15.
Figure 18:
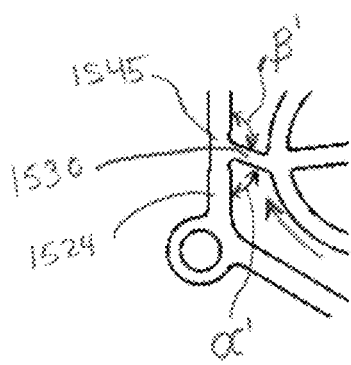
FIG. 18 depicts an enlarged portion of the support frame of FIG. 16.

The implants described herein, whether formed of a single or multiple implant sections may be used in treating a wide variety of bone defects or even for cosmetic purposes. By way of example, FIG. 10 depicts an implant (810) configured for use in repairing, restoring or augmenting a patient's zygomatic bone (cheek bone). Implant (810) is configured similar to implant section (10) described previously, but cut and shaped to the appropriate size (e.g., by cutting off unneeded portions of support frame (20) and removing or not molding unneeded mosaic plates (12)). Similarly, implant (811) in FIG. 16 is configured for use in repairing, restoring or augmenting a patient's mandible (chin). Once again, implant (811) may be formed from an implant section (10) which is shaped and configured in the desired size and shape. Of course, implants constructed in the manner described herein may be shaped and configured for any of a variety of other bones of a patient.

FIGS. 11-24 depict alternative embodiments of an implant (1510) suitable for use in, for example, filling a bore hole (also referred to as a burr hole) in a bone, particularly a patient's skull. These implants are similar to those described in Applicant's U.S. Pub. No. 2013/0053900A1, published on Feb. 28, 2013, entitled "Implants and Methods for Using Such Implants to Fill Holes in Bone Tissue," PCT Pub. No. WO 2013/027175, also published on Feb. 28, 2013, entitled "Implants and Methods for Using Such Implants to Fill Holes in Bone Tissue," and the '381 App. The foregoing U.S. and PCT publications are incorporated by reference herein.

As described in the publications referenced in the preceding paragraph, when it is necessary to remove a portion of a patient's skull, two (or more, typically three) bore holes are created. The bore holes are then joined by saw cuts that together with the bore holes form a continuous cut line through the skull, thereby releasing a bone flap from the rest of the skull. The bone flap can be lifted to allow access to the underlying tissue. When the bone flap is replaced, it is desirable not only to anchor it into place but also to at least partly fill the bore holes. Implant (1510) is adapted for such purpose.

Similarly, one or more bore holes may also be made in a patient's skull in order to, for example, allow for the insertion of drainage tubes for draining a subdural hematoma. When the drainage tubes are removed, it is desirable to at least partially fill the bore hole(s). Implant (1510) is also adapted for such purpose.

Implant (1510) generally comprises a biocompatible plate (1512) and a wire support frame (1520). While plate (1512) is depicted as having a circular cross-section and being in the shape of a cylinder, particularly a tapered cylinder with a rotational axis (L'), other implant plate shapes are also possible. For example, plate (1512) can have an oval, triangular, square, rectangular, pentagonal, hexagonal, etc. cross-section. However, a cylindrical shape, particularly a tapered cylinder, will most closely match a circular bore hole and allow plate (1512) to be snugly urged into a bore hole, with the taper facilitating insertion of the plate into the bore hole. Thus, upper surface (1513) of plate (1512) has a larger surface area than lower surface (1514) (see FIG. 13). In some embodiments, the diameter of upper surface (1513) of plate (1512) is between about 0.7 and about 1.6 cm, while the diameter of bottom surface (1514) is between about 1.4 and about 0.5 cm. In some embodiments, plate (1512) has a thickness of between about 0.3 and about 0.5 cm.

The biocompatible plate (1512) and support frame (1520) are made from any of the variety of materials, using the various methods previously described with respect to the wire mesh support frames and biocompatible mosaic plates of the previously described mosaic implant sections. Thus, while plate (1512) may be made from any of a variety of biocompatible materials suitable for implantation in a patient, in one embodiment plate (1512) comprises hydraulic cement, particularly the cement compositions previously described herein (i.e., predominantly monetite). Likewise, the support frame (1520) can be made from any of a variety of biocompatible materials suitable for implantation in a patient, such as various metals, polymers, or even composite materials of two or more metals and/or polymers. Non-limiting examples include biocompatible polymers such as polycaprolactone, shape memory alloys (e.g., nitinol), titanium, titanium alloys (e.g., Ti-6Al-4V) and stainless steel. In the embodiment shown, support frame (1520) is a unitary structure cut from a metal sheet (e.g., titanium alloy) and therefore is not only initially generally planar (i.e., flat) (see FIG. 14) but also of uniform thickness.

As with the mosaic implants described previously herein, the wire support frame (1520) includes various wire segments that are joined to one another. In this particular embodiment, support frame (1520) comprises a central portion (1522) located at least partially or, in the embodiment shown, entirely within plate (1512) (see FIG. 12). Support frame (1520) further includes an outer rim (1524) extending about at least a portion of the outer periphery of the plate (1512), evenly spaced from and about central portion (1522). In other words, central portion (1522) of support frame (1520) and plate (1512) are positioned within, and evenly spaced from, outer rim (1524). Biocompatible plate (1512) is molded (or otherwise formed) about central portion (1522) such that central portion (1522) is located intermediate upper surface (1513) and lower surface (514) of plate (1512) (see FIGS. 11 and 13). However, since, prior to molding the plate (1512), central portion (1522) is located below the plane of outer rim (1524) (see FIG. 15), the upper surface (1513) of the biocompatible plate (1512) is flush (or nearly flush) with the upper surface (1521) of the outer rim and eyelets (see FIG. 13). In some embodiments, the implant is configured such that the upper surface (1513) of the plate, when viewed from the side, extends above the upper surface (1521) of the outer rim (1524) and eyelets (1540) by about about 1.0 mm or less, or between about 0.25 and about 0.75 mm, or about 0.5 mm. By locating the plate (1512) such that its upper surface (1513) extends slightly above the upper surface of the outer rim and eyelets, contact and resulting friction between the metal support frame and soft tissue is reduced, and the implant will better follow the natural, convex curvature of the skull. In addition, eyelets (1540) can be countersunk such that the head of a screw inserted therethrough will not extend above the upper surface (1521) of the retention eyelet.

Figure 12:
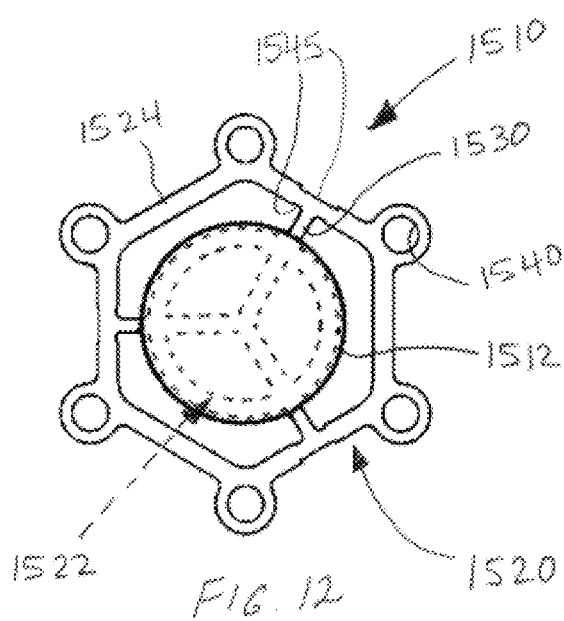
FIG. 12 depicts a top plan view of the embodiment of FIG. 11, wherein the central portion of the support frame is shown in dashed line.
Figure 13:
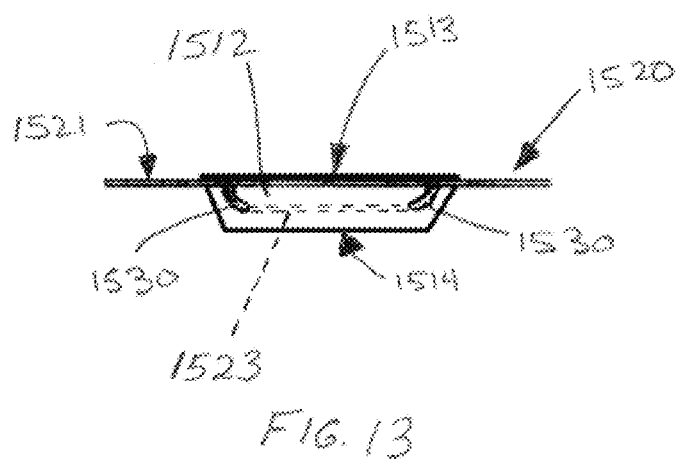
FIG. 13 depicts a side view of the embodiment of FIG. 11.

In the embodiment shown, central portion (1522) of support frame (1520) comprises an inner ring (or annulus) (1523), and outer rim (1524) is also an annulus—in the depicted embodiment of FIG. 12, a hexagonal ring. The inner ring (1523) of central portion (1522) has a longitudinal axis (L") (see FIG. 14) which, after molding of the plate (1512), coincides with the longitudinal axis (L') of the plate. In addition, in embodiments wherein the outer rim comprises an annulus or ring (e.g., a circular, oval or polygonal ring), the longitudinal axis of such ring-shaped outer rim will also coincide with the longitudinal axis (L") of the inner ring (1523) of central portion (1522) such that the central portion (1522) is centrally located within the outer rim (1524). It will be understood, however, that each of the inner ring (1523) and outer rim (1524) can be any of a variety of shapes other than those depicted. For example, inner ring (1523) and outer rim (1524) can comprise circular, oval or polygonal (e.g., hexagonal, pentagonal, etc.) ring-shapes.

Central portion (1522) of support frame (1520) further includes an inner support structure comprising a plurality of inner support members (1526). Inner support members (1526) in the form of wire segments extend radially inward from inner ring (1523) of central portion (1522), and are joined to one another at central juncture (1528) located on the axis (L") of support frame (1520) (which coincides with the rotational axis (L') of plate (512)). The inner support members provide additional strength and rigidity to support frame (1520), while still allowing the biocompatible plate to be molded about and between the wire segments forming central portion (1522) (e.g., within the spaces between inner ring (1523) and inner support wires (1526)).

The outer rim (1524) further includes a plurality of fastening points adapted for securing the implant to bone surrounding a bore hole. In the embodiments shown, the fastening points comprise a plurality of retention eyelets (1540). The retention eyelets (1540) are adapted to receive a fastener therethrough, such as a bone screw or other fastener known to those skilled in the art. Retention eyelets (1540) are arrayed around the periphery of the outer rim (1524), and, in the depicted embodiment, are located at the apexes of the hexagonal outer rim (1524). It will be understood, however, that any number of eyelets (1540) or other fastening points can be provided at a variety of alternative locations, such as intermediate the apexes of the hexagonal outer rim (1524) or at only some of the apexes of the polygonal outer rim (e.g., every other apex). As also seen in the embodiment of FIGS. 11-19, the retention eyelets (1540) are integral with the hexagonal outer rim (1524) such that the external periphery of the outer rim is not a perfect hexagon.

In the alternative embodiment shown in FIG. 20, the outer rim (1624) is, like the previous embodiment, a hexagonal ring. However, in this embodiment the outer rim (1624) of the support frame (1620) comprises a plurality of wire segments (1625) that extend between and connect adjacent eyelets (1640) arrayed at hexagonal apexes.

FIGS. 21 and 22 depict yet another alternative embodiment of a support frame (1720). In this embodiment, the outer rim (1724) is annular (i.e., circular), with a plurality of retention eyelets (1740) arrayed about the circumference of outer rim (1724). Central portion (1722) comprises an inner ring (1723), as in the previous embodiments.

As mentioned previously, central portion (1522, 1622, 1722) is positioned within the interior of the outer rim (1524, 1624, 1724), and evenly spaced therefrom in the depicted embodiments. A plurality of wire arms (1530, 1630, 1730) extend between and connect the outer rim (1524, 1624, 1724) to inner ring (1523, 1623, 1723) of central portion (1522, 1622, 1722). In the embodiments shown, since central portion (1522, 1622, 1722) is located entirely within the biocompatible plate (1512, 1612, 1712), wire arms (1530, 1630, 1730) extend outward of the plate (1512). While any number of wire arms (1530, 1630, 1730) extending between and connecting the outer rim to the central portion (1522, 1622, 1722) may be provided, in the depicted embodiments three such arms (1530, 1630, 1730) are used. By employing at least three wire arms (1530, 1630, 1730), the central portion of the support frame is better supported within the outer rim while, as further described below, allowing the outer rim to be readily deformed such that the retention eyelets can be better positioned to match the surrounding bone in a patient (e.g., see FIGS. 23 and 24). However, in alternative embodiments, only two such wires rims are employed, and in still further embodiments more than three wire arms (1530, 1630, 1730) are provided.

Also in the depicted embodiments, wire arms (1530, 1630, 1730) extend outward of the plate (1512) and are connected to the outer rim (1524, 1624, 1724) intermediate of adjacent eyelets (1540, 1640, 1740). As further described below and depicted in FIGS. 23 and 24, this arrangement facilitates the bending of the outer rim such that one or more of the retention eyelets can be oriented at an angle with respect to the plane of the unbended outer rim and upper surface of the plate. By arranging the wire arms (1530, 1630, 1730) so as to connect to the outer rim (1524, 1624, 1724) intermediate of adjacent eyelets, portions of the rim can be deformed (e.g., bent) in order to orient any one or more of the eyelets such that the bottom surface of the eyelet is flat (or nearly flat) against surrounding bone. In other words, this arrangement maximizes the extent of deformable rim between each eyelet and one of the wire arms (1530, 1630, 1730), thus maximizing the amount of deformation that is possible without also deforming a wire arm and potentially causing the plate to crack.

Figure 19:
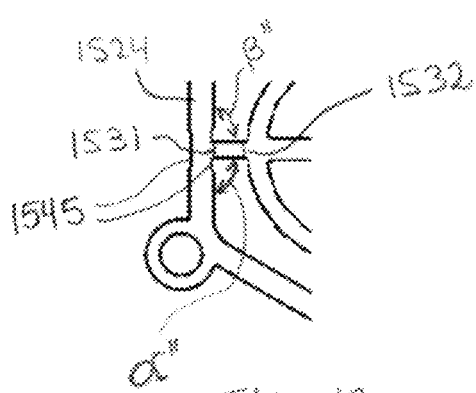
FIG. 19 depicts an enlarged portion of the support frame of FIG. 23.

In order to further facilitate deformation of the outer rim and/or external portions of the wire arms so that the retention eyelets can be oriented to better match the curvature of surrounding bone without cracking the biocompatible plate, deformation zones are provided on the portions of the wire arms external to the plate and/or on the outer rim adjacent the intersection of the arms therewith. In the embodiment shown in FIGS. 11-19, reduced width regions (1545) are provided on outer rim (1524) where the support arms (1530) intersect the rim. As best seen in FIGS. 12 and 19, reduced width regions (1545) are provided not only along the interior edge of the outer rim adjacent either side of the support arm (1530), but also along the exterior edge of the rim opposite from where the support arm (1530) extends inwardly from the rim. While not shown in FIGS. 21 and 22, similar deformation zones are provided on the alternative embodiments of FIGS. 20-22.

In alternative embodiments, the wire arms extending outward of the biocompatible plate intersect and are connected to the outer rim at or adjacent the retention eyelets.

As before, the support frame (1520, 1620, 1720) can be formed in any of a variety of manners such as forging, casting, molding, extrusion, cutting, etching, stamping, welding, etc. In the depicted embodiments, support frame (1520, 1620, 1720) is formed from a metal sheet (e.g., titanium) which is stamped or cut (e.g., using an automated laser cutting device) in a predetermined pattern to produce a unitary support frame of constant thickness. Alternatively, support frame (1520, 1620, 1720) may be cut, etched, stamped, molded or otherwise formed from a biodegradable polymer such as polycaprolactone. As yet another alternative, support frame (1520, 1620, 1720), as well as a mold negative for use in fabricating the mold for forming the mosaic plate (1512, 1612, 1712), are manufactured using additive manufacturing techniques (aka, 3D-printing). Any of a variety of additive manufacturing methods can be employed, including stereolithography, fused deposition modeling (also known as fused filament fabrication), selective laser sintering, selective laser melting, electron beam melting, and others known to those skilled in the art or hereafter developed.

Figure 14:
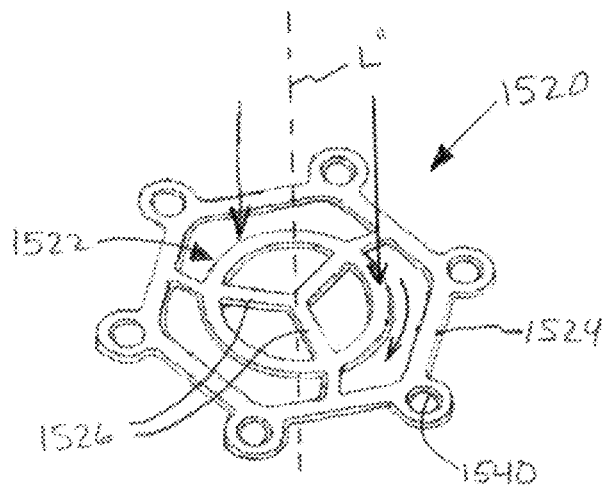
FIG. 14 depicts a perspective view of the support frame used in the implant of FIG. 11, prior to deformation of the wire arms connecting the outer rim and inner ring of the support frame, such that the support frame is substantially planar.
Figure 15:
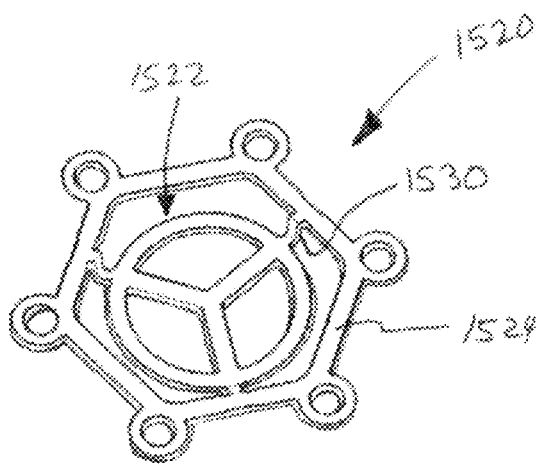
FIG. 15 depicts a perspective view similar to FIG. 14, wherein the central portion of the support frame has been urged downwardly such that the wire arms connecting the outer rim have been deformed and the inner ring has rotated and moved downward as compared to FIG. 14.

In the depicted embodiments, support frame (1520, 1620, 1720) comprises titanium, and is cut from a flat sheet of titanium or titanium alloy using an automated, programmable laser cutting device. The titanium or titanium alloy sheet comprises grade 2, 4 or 5 titanium, 0.3 to 0.6 mm thick. In the embodiment shown, grade 2 titanium, 0.4 mm thick is used. While cutting support frame (1520, 1620, 1720) from a flat sheet of titanium or other material facilitates fabrication, support frame (1520, 1620, 1720) will initially comprise a flat, generally planar structure, as best seen in FIG. 14. While the biocompatible plate can be molded about the central portion (1522, 1622, 1722) with the support frame in this planar configuration, the central portion will not be centrally located in the plate and/or the upper surface of the plate will not be flush (or nearly flush) with the upper surface of the outer rim and retention eyelets. In order to position central portion (1522, 1622, 1722) below the plane of the outer rim (1524, 1624, 1724) (see FIG. 15), thus allowing the upper surface of the plate to be flush (or nearly flush) with the upper surface of the outer rim and eyelets (see FIG. 13), the central portion of the support frame is urged downwardly into the position shown in FIG. 15 prior to molding the biocompatible plate about the (1522, 1622, 1722).

The ability to urge the central portion (1522, 1622, 1722) of the support frame below the plane of the outer rim is facilitated by wire arms (1530, 1630, 1730) that are not only deformable but also obliquely extend between outer rim (1524, 1624, 1724) and inner ring (1523, 1623, 1723) of central portion (1522, 1622, 1722). Prior to molding of the biocompatible plate, deformable arms (1530, 1630, 1730) extend inwardly away from outer rim (1524, 1624, 1724) at an oblique included angle ($\alpha'$). In the case of a circular or otherwise curved outer rim such as outer rim (1724) depicted in FIGS. 21 and 22, the oblique angle ($\alpha'$) is the included angle between the deformable arm (1730) and the tangent (T) to the outer rim (1724) whereat the arm (1730) intersects the outer rim (1724). Because deformable arms (1530, 1630, 1730) extend inwardly away from outer rim (1524, 1624, 1724) at an oblique included angle ($\alpha'$), the deformable arms (1530, 1630, 1730) are longer than they would be if they extended perpendicularly from the outer rim to the inner ring (1523, 1623, 1723).

Each of the deformable arms (1530, 1630, 1730) of an implant is also obliquely angled in the same direction with respect to the outer rim (1524, 1624, 1724). Thus, in the exemplary embodiments depicted in FIGS. 11-24, the included angle ($\alpha'$) between each arm (1530, 1630, 1730) and the associated outer rim (1524, 1624, 1724) is less than 90 degrees on the counter-clockwise side of the intersection, while the supplementary angle ($\beta'$) on the clockwise side of the intersection is greater than 90 degrees. In the implant embodiments shown, the included angle ($\alpha'$) between each arm (1530, 1630, 1730) and the associated outer rim (1524, 1624, 1724) of the support frame is the same, and the length of each arm (1530, 1630, 1730) of the support frame is the same. Accordingly, the inner ring (1523, 1623, 1723) is centrally located in the interior of outer rim (1524, 1624, 1724).

By connecting the inner ring (1523, 1623, 1723) to the outer rim (1524, 1624, 1724) by obliquely angled, deformable arms (1530, 1630, 1730), central portion (1522, 1622, 1722) of the support frame can be urged downwardly with respect to the outer rim. As depicted in FIGS. 14-19, as the central portion (1522, 1622, 1722) is urged downwardly with respect to outer rim (1524, 1624, 1724), the angle ($\alpha'$) between arms (1530, 1630, 1730) and the outer rim will increase towards 90 degrees and the inner ring (1523, 1623, 1723) will rotate clockwise about the longitudinal axis (L) while the inner ring remains centered within the outer rim. In addition, arms (1530, 1630, 1730) will bend downwardly adjacent the outer rim (e.g., at 1531 in FIG. 19) and inwardly adjacent the outer surface of the plate (e.g., at 1532 in FIG. 19). Bending of the deformable arms (1530, 1630, 1730) is also facilitated by the fact that, in the depicted embodiments, the wire arms are not as wide as the outer rim (1524, 1624, 1724). As the central portion is pressed further inwardly, the inner ring (1523, 1623, 1723) will continue to rotate clockwise and move downwardly with respect to the outer rim until the angle ($\alpha''$) between arms (1530, 1630, 1730) and the outer rim is approximately 90 degrees (thus limiting the degree to which the inner ring can be depressed with respect to the outer rim). In order to facilitate downward movement and rotation of the inner ring with respect to the outer rim, the support frame (1520, 1620, 1720) can be positioned in a suitably designed fixture which allows downward movement and rotation of the central portion (1522, 1622, 1722) and bending of deformable arms (1530, 1630, 1730), while maintaining the planar configuration of the outer rim (1524, 1624, 1724). The fixture can comprise, for example, a clamping device which not only holds the outer rim flat but also presses the central portion of the support frame downwardly with respect to the outer rim.

Once the support frame (1520, 1620, 1720) has been converted from a flat, planar arrangement (FIG. 14) to that wherein the central portion (1522, 1622, 1722) is located below the plane of the outer rim (FIG. 15), the support frame is positioned in a suitably shaped mold for the biocompatible plate and the plate is then molded about the central portion of the support frame. The upper surface of the plate can be made flush (or nearly flush) with the upper surface of the outer rim of the support frame and/or the bone surrounding a bore hole or other defect, while the central portion of the support frame is located intermediate the upper and lower surfaces (1513, 1514) of the plate. In addition, this feature can be provided while still allowing the support frame (1520) not only to be fabricated as a flat, unitary structure, such as by cutting a flat sheet of material (e.g., titanium), rather than more complicated fabrication techniques.

In order to secure the implant (1510) in a bore hole or other bone defect, the plate (1512) is alignably positioned within the bore hole. The implant is then secured to bone surrounding the bone defect, such as by bone screws urged into the bone through the retention eyelets (1540). As a result, the implant is secured in place, with the plate firmly located in, and filling, the bore hole.

Since the bone surrounding a bore hole is usually curved, to varying degrees and often in more than one direction, it will usually be desirable to bend portions of the support frame in order to orient the retention eyelets and rim such that their bottom surfaces will lie as flat as possible against the bone. This not only minimizes any gaps between the support frame and surrounding bone, but also helps to ensure that a screw or other fastener driven through the eyelets into the surrounding bone will have sufficient purchase. For example, since the retention eyelets in the embodiments shown in FIGS. 11 and 21 extend away from the outer circumference of the outer rim (1524, 1724), the eyelets can be deformed (i.e., bent) where the eyelets intersect the outer rim in order to facilitate a more secure attachment to the surrounding bone as the eyelet can be manipulated so as to lay flush against the outer surface of the bone.

Figure 23:
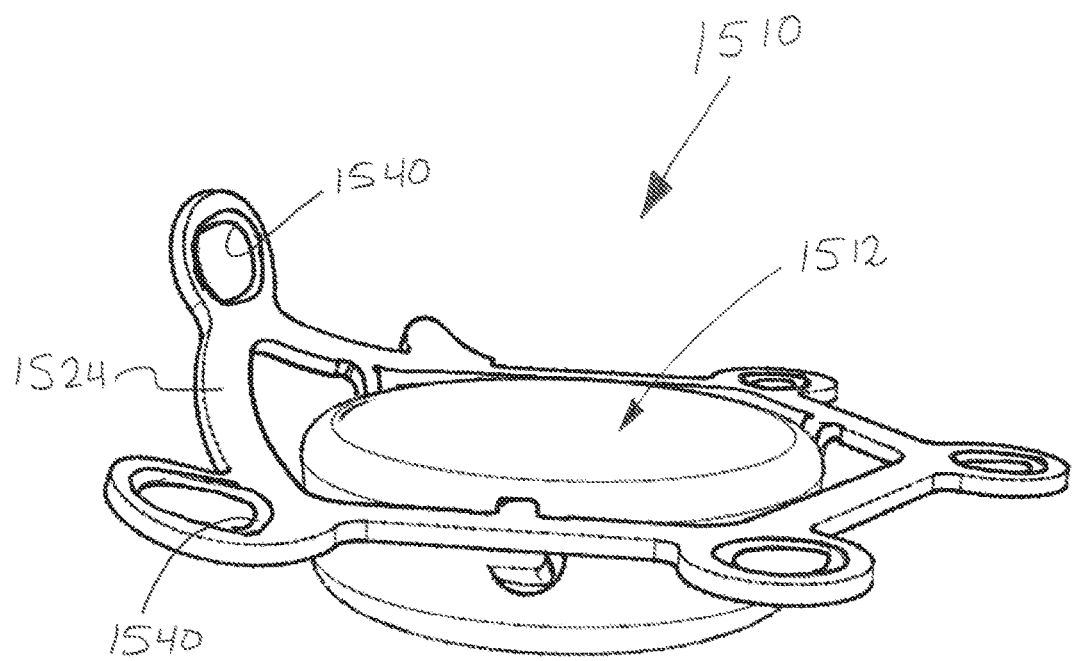
FIG. 23 depicts a side view of the implant of FIG. 11, wherein a portion of the outer rim has been bent.
Figure 24:
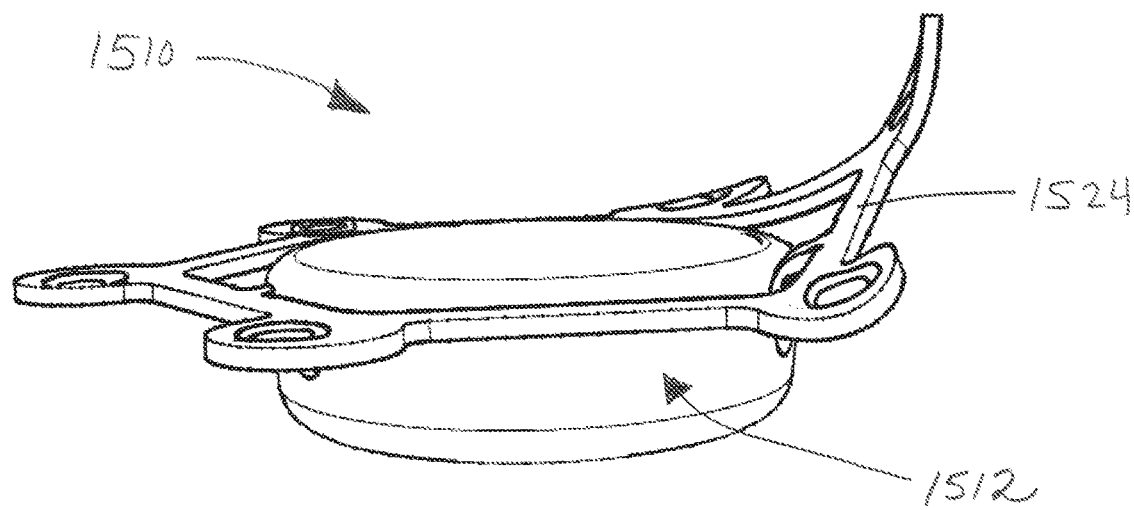
FIG. 24 depicts a top view of the implant of FIG. 23.

In addition, particular when a greater repositioning of one or more eyelets is required so as to better match surrounding bone, portions of the outer rim can be bent so that one or more of the retention eyelets can be better oriented with respect to the bone surrounding a bore hole. By way of example, FIGS. 23 and 24 depict an implant (1510) wherein, prior to implantation in patient, portions of the rim (1524) have been bent upwardly so as to orient two of the retention eyelets (1540) at an angle with respect to the plane of the upper surface of the plate (1512). Such bending may be necessary, for example, when the implant is to be inserted into a bore hole located in or immediately adjacent to a concavely curved surface of a patient's skull (e.g., a bore hole in the sphenoid bone immediately adjacent the zygomatic bone). As a result, a bone screw or other fastening device can be driven through two of the retention eyelets in a direction nearly parallel to the upper surface of the plate (1512). Of course the outer rim and, to some extent, portions of the wire arms (1530) external the plate, can be bent in any of a variety of directions (e.g., upwardly or downwardly) and degrees, as necessary to better match the surface of the bone surrounding a bore hole, and without cracking the plate (1512). In order to further facilitate deformation of the outer rim and/or external portions of the wire arms so that the retention eyelets can be oriented to better match the curvature of surrounding bone without cracking the biocompatible plate, deformation zones are provided on the portions of the wire arms external to the plate and/or on the outer rim adjacent the intersection of the arms therewith. In the embodiment shown in FIGS. 11-19, reduced width regions (1545) are provided on outer rim (1524) where the support arms (1530) intersect the rim. As best seen in FIGS. 12 and 19, reduced width regions (1545) are provided not only along the interior edge of the outer rim adjacent either side of the support arm (1530), but also along the exterior edge of the rim opposite from where the support arm (1530) extends inwardly from the rim. While not shown in FIGS. 21 and 22, similar deformation zones are provided on the alternative embodiments of FIGS. 20-22.

Figure 25:
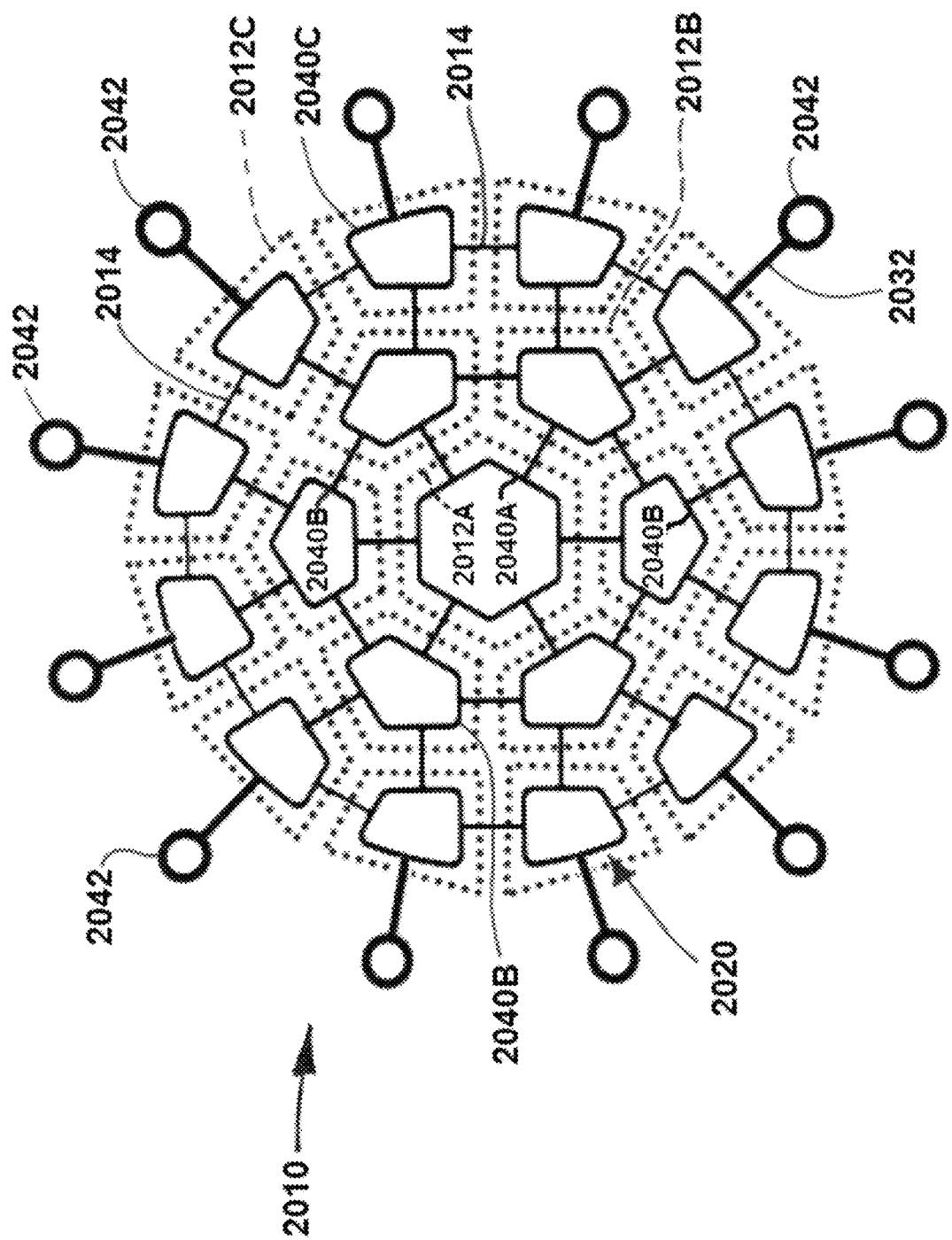
FIG. 25 depicts a top schematic plan view of yet another embodiment of a support frame for an implant for correcting bone defects, wherein the location of the mosaic plates of the final implant are shown in dashed line.
Figure 26:
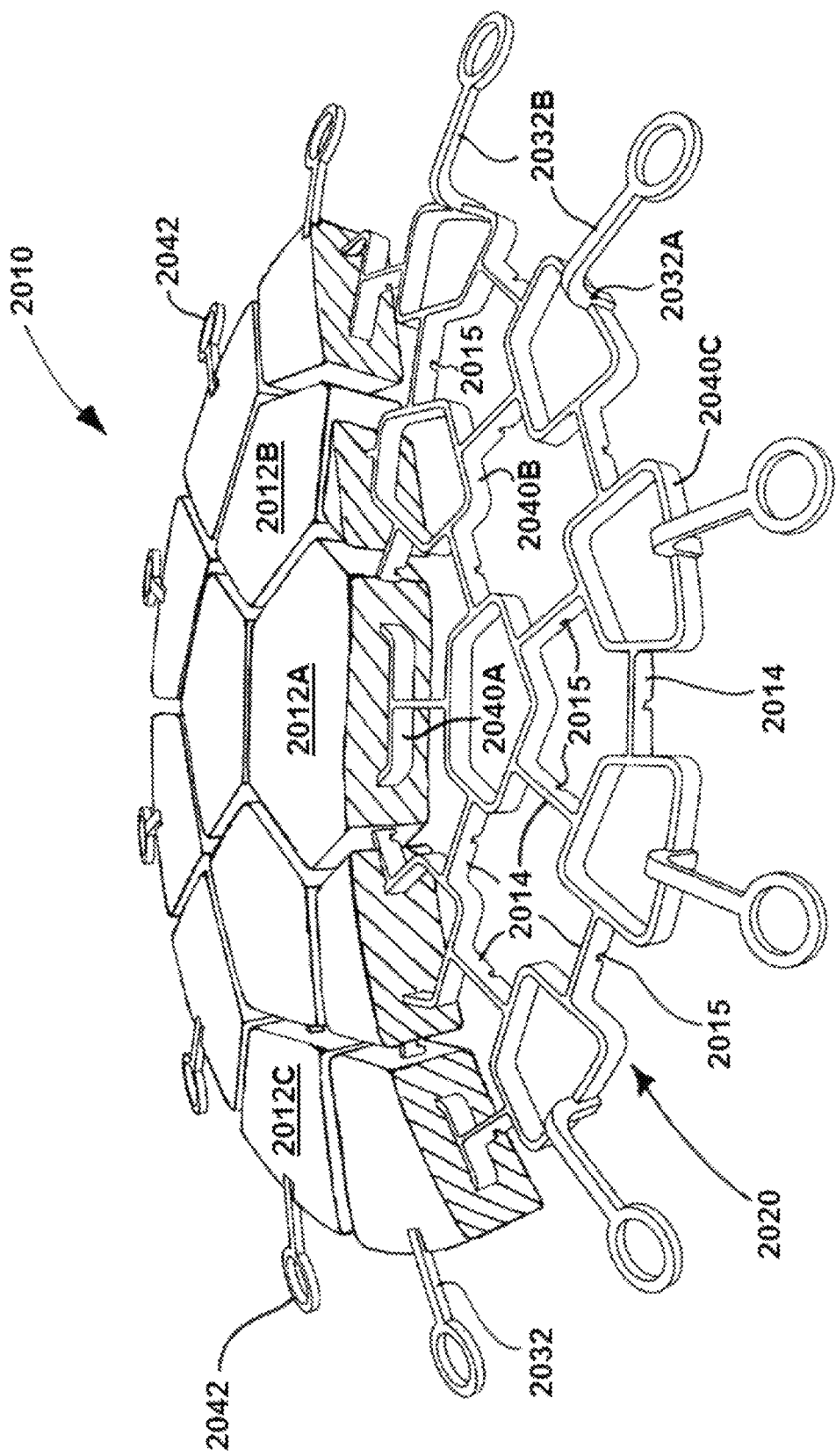
FIG. 26 depicts a partial cross-sectional view of a mosaic implant utilizing the support frame of FIG. 25.

FIGS. 25 and 26 depict yet another alternative embodiment of a mosaic implant (2010). Unlike the mosaic implant section (210) of FIGS. 1-4, however, implant (2010) is specifically designed to match a particular cranial defect of a patient, and without having to be coupled to one or more additional implant sections. In addition, as further described below, implant (2010) can be fabricated as a rigid structure which is generally not deformable (other than, perhaps, the retention arms (2032) in order to facilitate proper securement of the implant in a patient). It will be understood that this embodiment is not limited to use in cranial defects, and does not preclude the coupling of two or more implants (2010) in the manner previously described. Implant (2010) is also depicted as having an overall circular shape when viewed from the top (FIG. 25), however, this implant embodiment may be fabricated in various other shapes so as to precisely match a particular patient's bone defect.

As best seen in the top plan view of FIG. 25, wherein the biocompatible mosaic plates are shown in dashed lines, implant (2010) comprises a plurality of biocompatible mosaic plates (2012A, 2012B, 2012C) which are interconnected with one another by a plurality of wires (2014) provided as part of a mesh support frame (2020). Each mosaic plate (2012) is connected to a plurality of the immediately adjacent mosaic plates by the wires (2014) which extend between and into adjacent mosaic plates (2012). Wires (2014) are in the form of struts having a thickness (i.e., height) greater than their width, as best seen in FIG. 26, thus providing greater rigidity to the support frame (2020). As further discussed below, each plate (2012A, 2012B, 2012C) is connected to three, five or six adjacent plates by the wires (2014). Of course this is merely exemplary of one possible embodiment, and other configurations are contemplated.

In the embodiment shown in FIGS. 25 and 26, support rings (2040A, 2040B, 2040C) have replaced the eyelets (40, 140, 240) of the previously described mosaic implant embodiments (i.e., FIGS. 1-4). Accordingly, support rings (2040A, 2040B, 2040C) are, in essence, enlarged "eyelets" which, in the particular embodiment shown, have a shape which corresponds to that of the mosaic plate in which the support ring (2040A, 2040B, 2040C) will be located following molding of the mosaic plates. The internal support rings (2040A, 2040B, 2040C), however, due to their increased size (including their thickness) as well as their being shaped to match the shape of the mosaic plates, provide greater support and resistance to cracking of the plates (2012) as compared to the eyelets (40, 140, 240), not only during fabrication, adjustment and placement of the implant but also after implantation. At the same time, since support rings (2040A, 2040B, 2040C) have an open interior region, they do not add nearly as much weight or cost as a solid support plate would.

While support rings (2040A, 2040B, 2040C) could be circular, oval or round in shape in alternative embodiments, in the exemplary embodiment shown in FIGS. 25 and 26 the support rings are in the form of polygons having rounded corners, particularly irregular quadrilaterals (2012C), irregular pentagons (2012B), and a central hexagon (2012A). Once again these polygonal shapes are merely exemplary of one particular embodiment. Such polygonal support rings provide a more robust structure, as noted above.

Each support ring (2040A, 2040B, 2040C) is positioned on the support frame (2020) so as to be located within the interior of a plate (2012A, 2012B, 2012C). In the embodiment shown, each support ring (2040A, 2040B, 2040C) is centrally located within a mosaic plate, approximately equidistant from the top and bottom surfaces of the plate, and approximately equidistant from each of the sidewalls of the plate. Wire struts (2014) intersect the sides of the plates at an angle of approximately 90°, as best seen in FIG. 25. As for the mosaic plates, the facing side edges of adjacent plates (2012) are also generally parallel to one another, particularly when viewed from the top or bottom. The sidewalls of the mosaic plates (2012), however, are tapered in some embodiments, as described previously, in order to, for example, allow for greater implant curvature without increasing the distance between adjacent plates.

In the embodiment shown in FIGS. 25 and 26, a single wire strut (2014) extends between each connected pair of adjacent plates. The wire struts (2014) are connected to one another via the support rings (2040A, 2040B, 2040C) so as to once again provide the support frame with a mesh structure. Alternatively, the support frame (2020) can be configured such that two or more struts will extend between one or more (or even all) of the connected pairs of adjacent plates.

As with the previously described embodiments, the support frame (2020) can be made from any of a variety of biocompatible materials suitable for implantation in a patient, such as various metals, polymers, or even composite materials of two or more metals and/or polymers. Non-limiting examples include biocompatible and/or biodegradable polymers such as polycaprolactone, shape memory alloys such as nitinol, titanium, titanium alloys (e.g. Ti-6Al-4V) and stainless steel. In the particular embodiment shown, support frame (2020) comprises titanium or a titanium alloy.

While support frame (2020) can be fabricated in a variety of ways (e.g., via a molding process), in this patient-specific embodiment of a mosaic implant (as well as the alternative embodiments depicted in FIGS. 27 to 52) support frame (2020) is fabricated by additive manufacturing techniques (also known as 3D-printing). Additive manufacturing of the support frame facilitates fabrication of a support frame (2020) and resulting implant (2010) that is specifically designed to match a bone defect of a specific patient, thus negating the need for a surgeon to extensively modify and adjust the implant at the time of surgery (although some adjustment may still be necessary or desired to achieve a better fit).

The struts (2014), in combination with the internal support rings (2040A, 2040B, 2040C) between which they extend, serve to interconnect the mosaic plates (2012), as best seen in the partially cut-away view of FIG. 26. Once again in order to provide additional shapability to implant (2010) the struts (2014) include deformation zones. The deformation zones are generally located in the middle of the length of the strut (2014) such that they will be located between adjacent plates. These deformation zones facilitate the shaping of the implant (2010) while reducing the risk that one or more plates will crack when the implant is deformed. Such deformation zones may also be used to shape the support frame (2020) prior to molding of the biocompatible plates (2012) in order to ensure the proper placement and positioning of the support frame (2020) within the mold. In the particular embodiment shown, each strut (2014) includes a deformation zone comprising a reduced-thickness region (2015). Reduced-thickness region (2015) comprises a notch extending upwardly from the bottom surface of the support strut (2014), positioned so as to be located between adjacent mosaic plates in the final implant assembly (2010) (see FIG. 26). In other words, the reduced-thickness regions (2015) are not enclosed by the plates.

It will be understood that the implant (2010) shown in FIGS. 25 and 26 may be modified such that deformation zones are not provided on all of the struts (2014). As yet another alternative, reduced-thickness regions (2015) may be configured to comprise a notch or other recess which extends downwardly from the upper surface of the support strut (2014). In still further embodiments, one or more of the struts (2014) may be configured to have a notch or other recessed area extend downwardly from the upper surface of the strut (2014) as well as a notch or other recessed area extend upwardly from the bottom surface of the strut (2014) (e.g., similar to the embodiment shown in FIG. 34). Furthermore, any of the various other types of deformation zones described previously may be provided on struts (2014) in place of reduced thickness regions (2015), such as reduced-width regions and/or pleated regions. Similar deformation zones may also be provided on retention arms (2032) (described below).

While the eyelets located in the interior of the mosaic plates have been replaced by the internal support rings (2040A, 2040B, 2040C) in the embodiment of FIGS. 25 and 26, a plurality of retention eyelets (2042) are arrayed around the periphery of the implant Like retention eyelets (40, 140, 240) described previously, retention eyelets (2042) are used to secure the implant (2010) in a patient such as by using bone screws or other types of fasteners.

In the particular embodiment shown, a retention arm (2032) extends away from the outermost sidewall of each outer support ring (2040C), with a retention eyelet (2042) located at the outer end of each retention arm. As best seen in FIG. 26, rather than extending away from outer support ring (2040C) in the same plane as the support ring, each retention arm (2032) includes an upwardly extending segment (2032A) which extends upwardly from the support ring, and a laterally extending segment (2032B) which extends laterally away from the upper end of upwardly extending segment (2032A), with the retention eyelet (2042) located at the distal end of laterally extending segment (2032B). In other words, each retention arm (2032) is bent such that the retention eyelet is elevated with respect to the support ring (2040C) to which it is attached. In this manner, the laterally extending segment (2032B) of the retention arm (2032) extends outwardly away from mosaic plate (2012C) at the upper surface of the plate (2012C). The upper surface of the laterally extending segment (2032B) of the retention arm (2032) may be flush with the upper surface of the mosaic plate (2012C) from which it extends, or, as seen in FIG. 26, slightly elevated with respect to the upper surface of the mosaic plate (2012C). By elevating the retention arm (2032) and retention eyelet (2042) with respect to the outermost mosaic plates, the implant (2010) can be inserted into a bone defect (e.g., a cranial defect) such that the upper surface of the mosaic plates (2012C) adjacent the periphery of the defect are generally level with the surrounding bone. This provides a smooth transition between the implant and surrounding bone, as well as a more precise fit. The retention arms and eyelets will extend over the bone so that bone screws or other fasteners may be driven into the surrounding bone through the retention eyelets (2042).

The biocompatible mosaic plates (2012A, 2012B, 2012C) of implant (2010) can be composed of any of a variety of the resorbable and/or stable (i.e., non-resorbable) biocompatible materials described previously herein. In one particular embodiment, mosaic plates (2012A, 2012B, 2012C) comprise any of the previously described hydraulic cement compositions (e.g., predominantly monetite), and a molding process is used to mold the mosaic plates onto the mesh support frame (2020).

As will be apparent from FIGS. 25 and 26, the mosaic plates (2012) of the implant are not arranged in ordered columns or a grid pattern. Instead, the mosaic plates are arranged similar to a turtle shell pattern, with one central hexagonal plate (2012A), a middle ring of pentagonal plates (2012B) arranged about the perimeter of the central plate (2012A), and an outermost ring of quadrilateral plates (2012C) arranged about the outer perimeter of the middle ring of pentagonal plates (2012B). This arrangement provides for considerable customization of the implant, including the ability to conform the implant to a variety of curved surfaces. For example, FIG. 26 depicts implant (2010) curved so as to conform to a generally spherical or spheroidal surface. The implant (2010) can be custom fabricated in the curved shape, such as by forming support frame (2020) in curved form via additive manufacturing, and then using a corresponding custom fabricated mold to form the plates in the manner previously described herein. Since implant (2010) is custom fabricated for a particularly patient, it can be made in a rigid form, since later deformation (e.g., by a surgeon) to match, for example, the curvature of a patient's skull will not be necessary.

In the particular embodiment shown in FIGS. 25 and 26, central plate (2012A) is connected to the six surrounding pentagonal plates (2012B), and each pentagonal plate (2012B) is also connected to the two adjacent quadrilateral plates (2012C) and the two adjacent pentagonal plates (2012B). Finally, the outermost quadrilateral plates (2012C) are each connected to the two adjacent quadrilateral plates (2012C). Thus, apart from the outermost quadrilateral plates which are only connected to three adjacent plates by struts (2014), all of the other plates are connected to an adjacent plate across each of its sides. Of course this is merely exemplary of one possible embodiment, and other configurations are contemplated, including additional rings of polygonal plates arrayed about one or more central hexagonal plates (or other shapes of plates).

Figure 27:
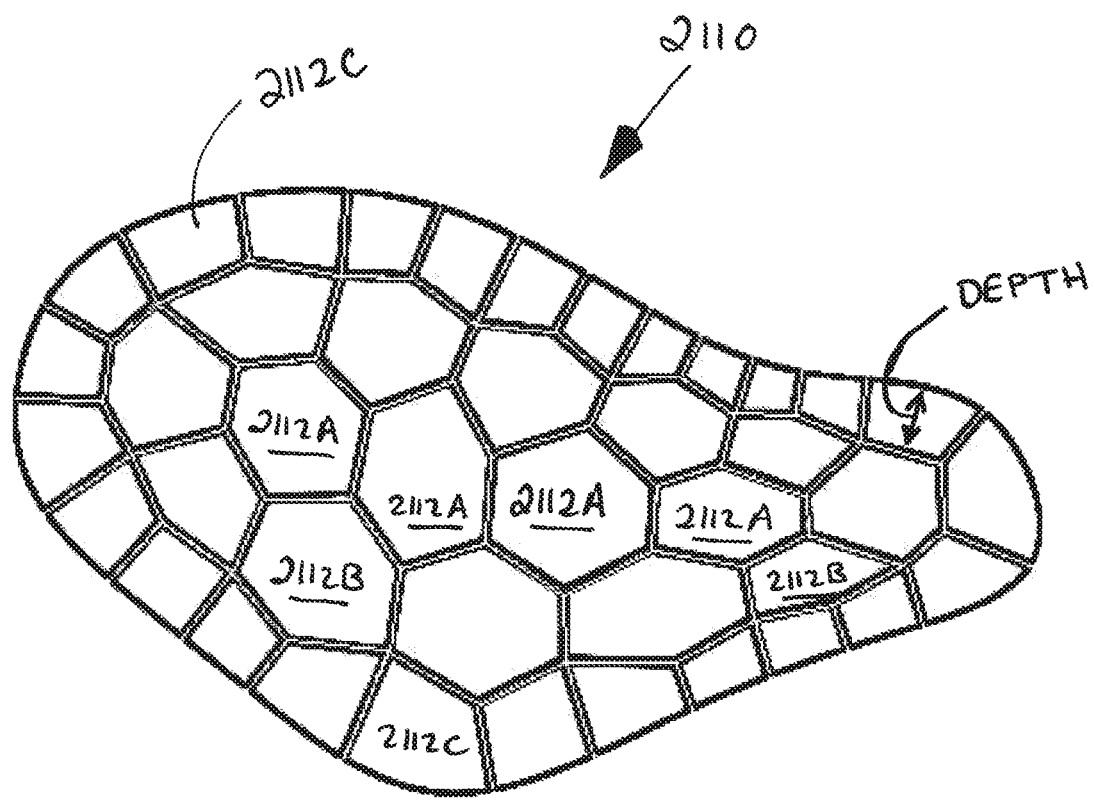
FIG. 27 depicts a top plan schematic view of a mosaic implant having an alternative arrangement of mosaic plates.

FIG. 27 depicts a schematic illustration of an implant (2110) having an alternative arrangement of mosaic plates (2112A, 2112B, 2112C). Implant (2110) includes four central hexagonal plates (2112A) in side-side relationship, a middle ring of hexagonal and pentagonal plates (2112B) arranged about the outer perimeter of the four central plates (2112A), and an outermost ring of quadrilateral plates (2112C) arranged about the outer perimeter of the middle ring of plates (2112B). Since the periphery of a bone defect (e.g., a cranial defect) is usually not a perfect circle, oval or other geometric shape, it is often necessary to provide an irregular outer perimeter shape for the implant. In the turtle shell arrangement depicted in FIG. 27, the shape and size of the outer perimeter can be readily customized during fabrication by, for example, controlling the depth of each quadrilateral plate (2112C) of the outermost ring of plates (see FIG. 27). The support frame used in the implant (2110) assembly of FIG. 27 can be configured in the same manner as support frame (2020) in the embodiment of FIGS. 25 and 26.

Figure 28:
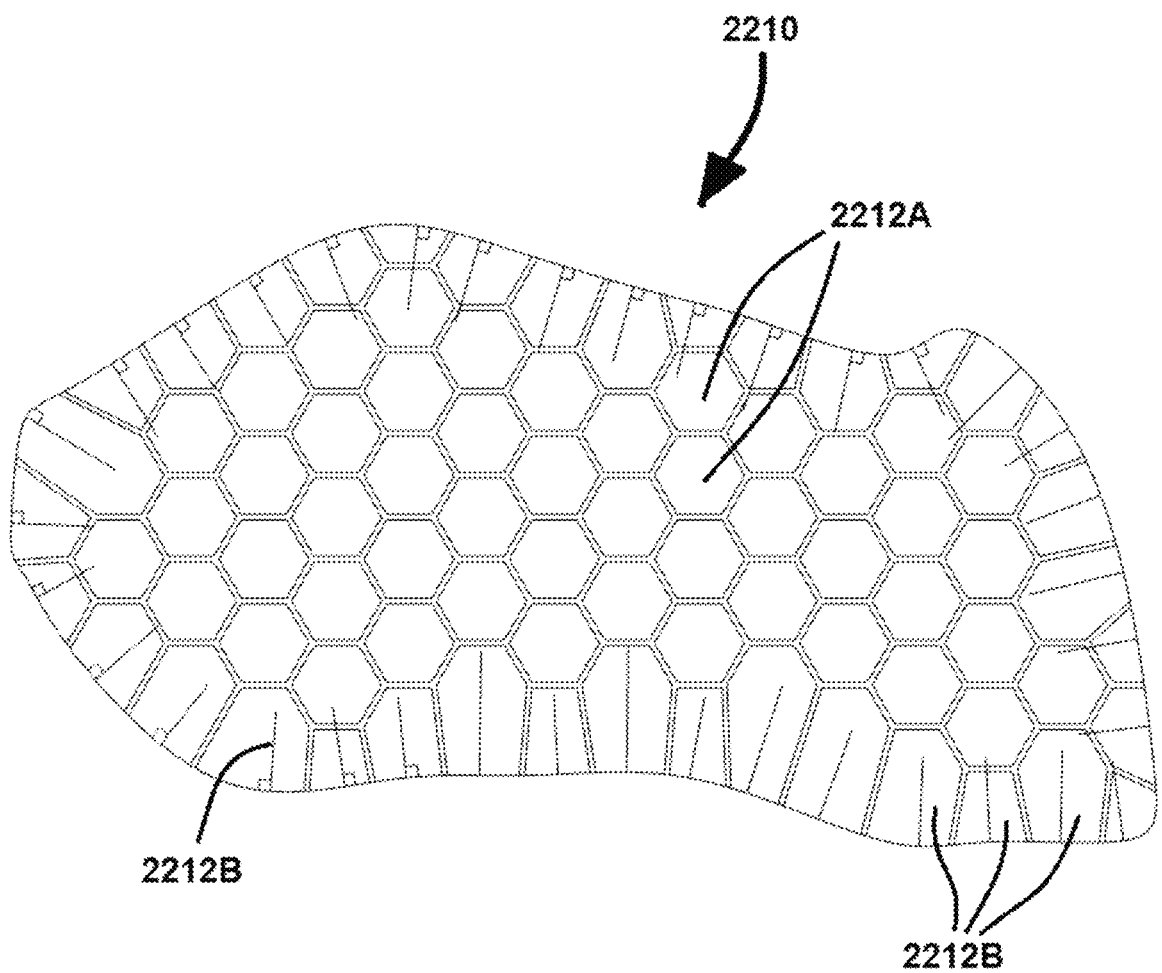
FIG. 28 depicts a top plan schematic view of another embodiment of a mosaic implant having an alternative arrangement of mosaic plates.

FIG. 28 depicts a schematic illustration of an implant (2210) having yet another alternative arrangement of mosaic plates (2212A, 2212B). Implant (2210) includes a central array of hexagonal plates (2212A) arranged similarly to the hexagonal plates of the embodiments shown in FIGS. 1-4. While the internal support frame within implant (2210) may be configured similarly to that shown in FIGS. 1-4, a support frame structure like that shown in FIGS. 25 and 26 is used in the implant (2210) of FIG. 28. Thus, the support frame includes internal hexagonal support rings in each of the hexagonal plates (2212A), with struts extending between adjacent plates. Also in FIG. 28, an outer ring of pentagonal, quadrilateral and/or triangular plates (2212B) is arranged about the outer perimeter of the central hexagonal plates (2212A). As before, the shape and size of the outer perimeter of implant (2210) can be customized by, for example, controlling the depth of each plate (2212C) of the outermost ring of plates, and/or controlling the shape and arrangement of each of those plates (2212C).

The implants shown in FIGS. 24-28, as well as the other implant embodiments described herein, can also be fabricated so as to have different properties on different portions of the implant. For example, the support frame can be made more flexible at the outer ring of mosaic plates in order to facilitate, for example, modifications of the implant during the implantation procedure so that the implant will more precisely match the outer perimeter of the bone defect. In contrast, the interior regions of the implant can be made stiffer in order to, for example, support more load.

Localized modifications to implant properties such as flexibility and/or stiffness can be accomplished in a variety of ways. For example, struts (2014) connecting adjacent support rings (2040) can be made thicker or thinner to alter implant properties, or multiple struts may even be provided in certain regions of the support frame. Similarly, and as depicted in the alternative embodiment of an implant (2310) in FIG. 29, certain struts may be omitted entirely to provide increased flexibility. In this embodiment, there are no struts connecting the outermost ring of quadrilateral mosaic plates (2312C) to one another. As a result, implant (2310) is more flexible about its periphery, specifically at the outermost plates (2312C). This allows, for example, one or more of the outermost plates (2312C) to be flexed upwardly or downwardly in order to better match a particular bone defect.

Figure 30:
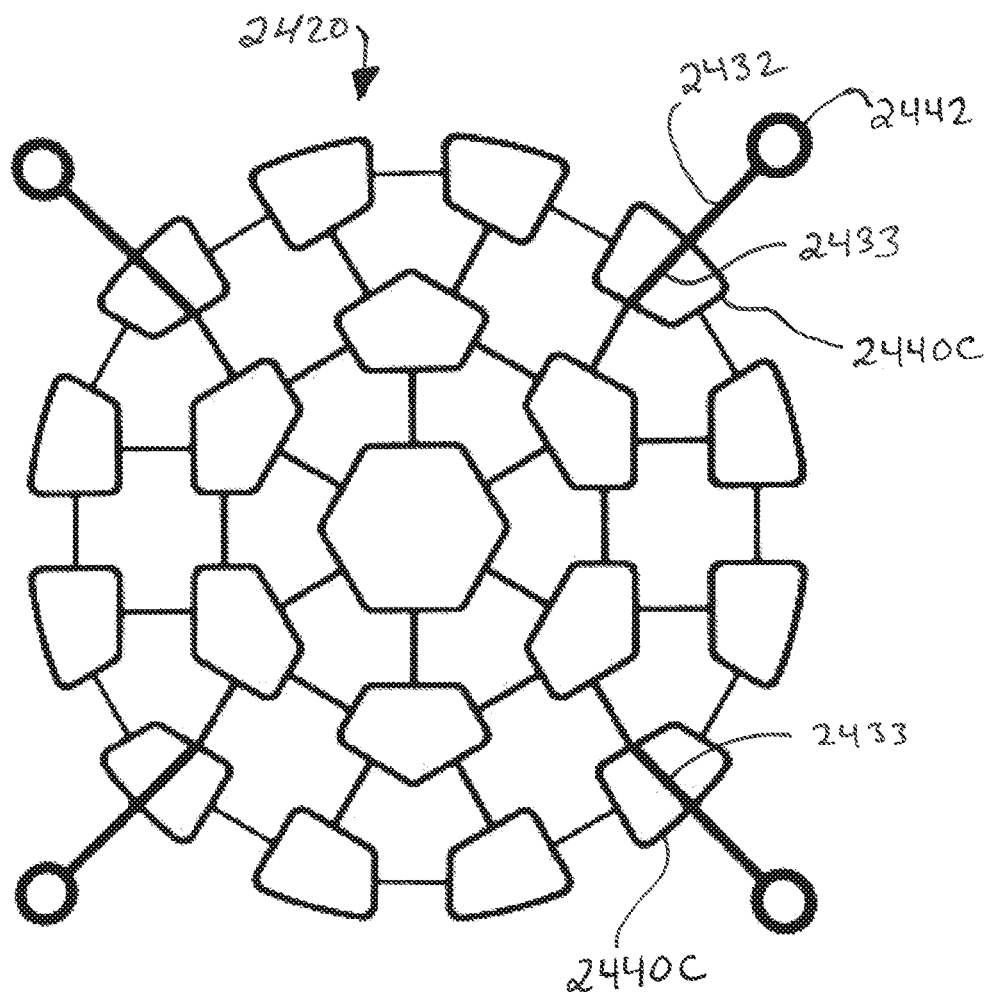
FIG. 30 depicts a top schematic plan view of another embodiment of a support frame for an implant for correcting bone defects, wherein the support frame has been modified as compared to that shown in FIG. 25.

FIG. 30 depicts another alternative embodiment of a support frame (2420). Support frame (2420) is similar to support frame (2020) in FIGS. 25 and 26 and can be used, for example, in the fabrication of an implant shaped similarly to the implant (2010). However, in addition to only having four retention eyelets (2442) arranged about its periphery, implant (2420) includes four additional internal struts (2433) which extend across the center of the support rings (2440C) from which the retention arms (2432) for eyelets (2442) extend. These additional struts (2433) provide additional strength in the region where the implant is attached to surrounding bone/tissue.

Figure 31:
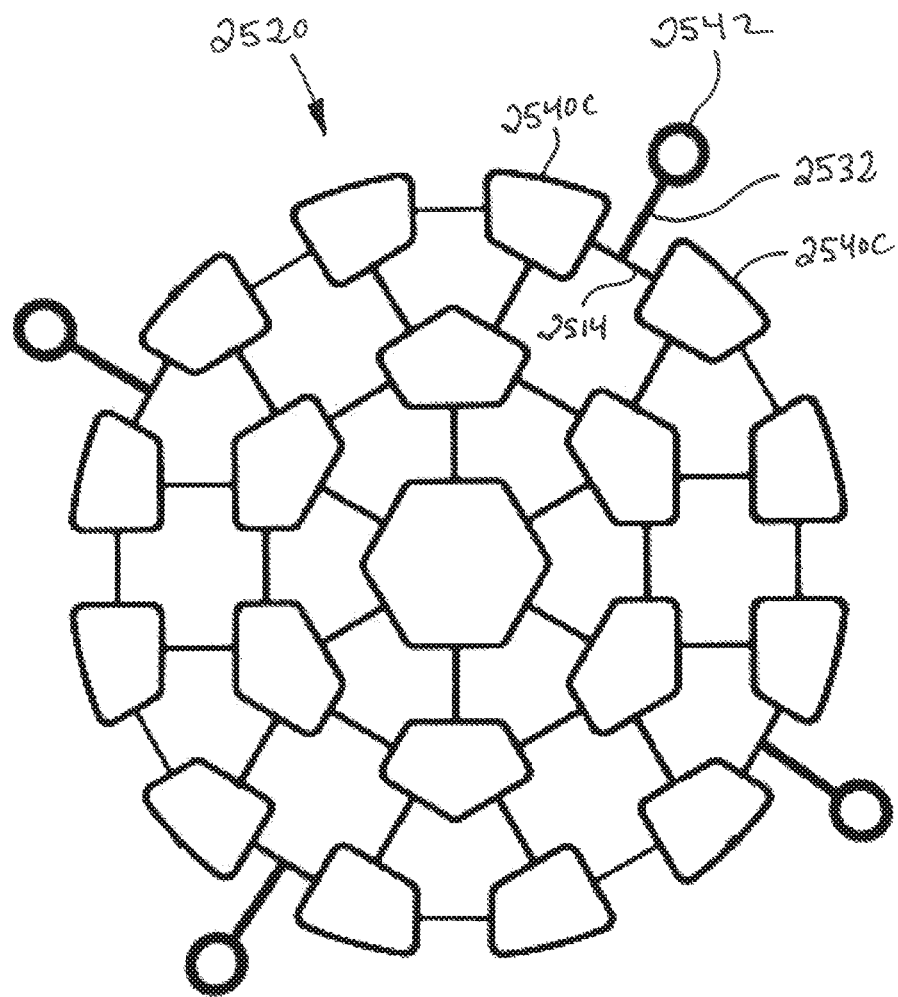
FIG. 31 depicts a top schematic plan view of an additional embodiment of a support frame for an implant for correcting bone defects, wherein the support frame has been modified as compared to that shown in FIGS. 25 and 29.

FIG. 31 depicts yet another alternative embodiment of a support frame (2520). Support frame (2520) is once again similar to support frame (2020) in FIGS. 25 and 26, and can be used, for example, in the fabrication of an implant shaped similarly to implant (2010). However, in addition to only having four retention eyelets (2542) arranged about its periphery, the retention arms (2532) of support frame (2520) in FIG. 31 extend outwardly (and upwardly) away from one of the struts (2514) extending between adjacent outermost support rings (2540C) rather than extending outwardly (and upwardly) away from one of the support rings itself. Thus, in the final implant the retention arms (2532) will extend from between two adjacent mosaic plates rather than extend out of one of the plates (as in FIG. 26). This modification provides greater flexibility in retention arm (2532), as well as a greater range of deformation as compared to support frame (2020) in FIG. 26.

Figure 29:
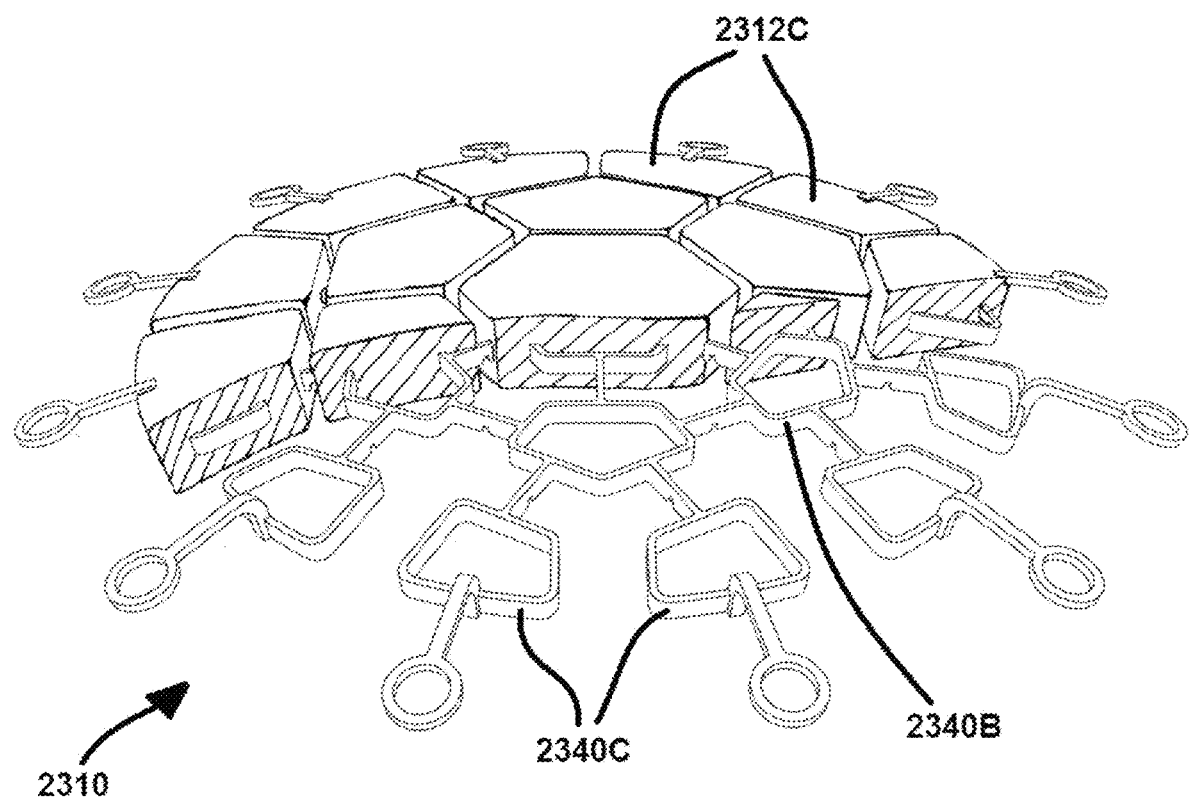
FIG. 29 depicts a partial cross-sectional view of a still further embodiment of a mosaic implant utilizing a support frame which is more flexible about its periphery than that depicted in FIG. 25.
Figure 32:
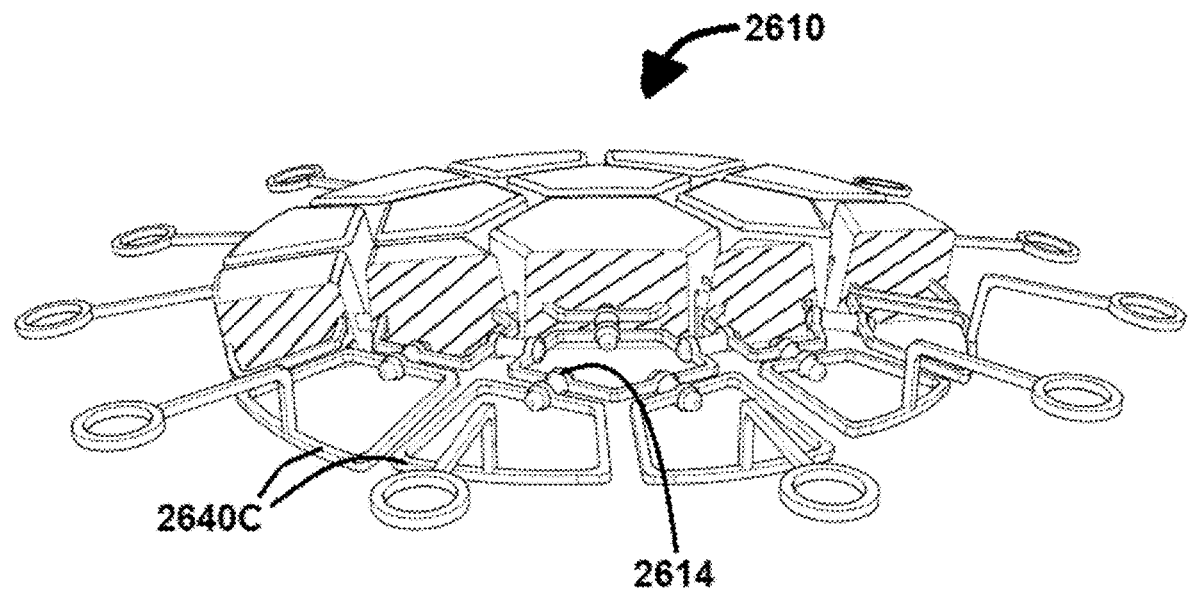
FIG. 32 depicts a partial cross-sectional view of a still further embodiment of a mosaic implant utilizing a support frame which is more flexible about its periphery than that depicted in FIG. 25.

FIG. 32 depicts an additional alternative embodiment of an implant (2610) which is similar to implant (2310) in FIG. 29. In this implant, the struts have been replaced by connecting pins (2614). Connecting pins (2614) in this embodiment are rod-shaped; however, any of a variety of other shapes may be employed. Connecting pins (2614) not only connect adjacent support rings, as shown, they also extend a distance into the interior of each support ring to which they are attached. Also, the wall of the support rings are enlarged adjacent the connecting pins (2614), as shown. Because of this, and due to the size and shape of the connecting pins as well as the fact that they span the distance between adjacent plates in the implant, the connecting pins (2614) can be bent in order to adjust the shape of implant (2610). Thus, connecting pins (2614) act as deformation zones for the implant (2610). By extending at least partially into the interior of the support rings, the connecting pins (2614) also help to stabilize the mosaic plates (i.e., to further prevent cracking of the plates). If desired, connecting pins (2614) may also be provided between adjacent outermost support rings, similar to the embodiment of FIGS. 25 and 26 in order to add additional strength and rigidity in the outer portion of implant (2610).

While the support frames described herein can be manufactured by any of the variety of techniques mentioned previously, in some embodiments the support frame, as well as the mold negative for use in fabricating the mold for forming the mosaic plates, are manufactured using additive manufacturing techniques (sometimes referred to as 3D-printing). In particular, the support frames and mold negatives for the implants shown in FIGS. 25-52 are manufactured in this manner so as to provide implants which are customized for each patient and the bone defect to be corrected. Any of a variety of additive manufacturing methods can be employed, including stereolithography, fused deposition modeling (also known as fused filament fabrication), selective laser sintering, selective laser melting, electron beam melting, and others known to those skilled in the art or hereafter developed. Selective laser melting is particularly useful in fabricating the support frame, particularly when the support frame is titanium, titanium alloy or other metals. Selective laser sintering is useful for fabricating the mold negative in polyamide and fused deposition modeling, on the other hand, is particularly useful for fabricating the mold negative from, for example, PLA or ABS.

The additive manufacturing of implants to precisely match a patient's bone defect (e.g., a cranial defect) comprises the steps of:
1. Obtaining computed tomography (CT-scan) or magnetic resonance (MRI) data from the patient.
2. Digitally creating an anatomical model of the bone defect to be treated.
3. Digitally generating the mesh support frame design to fit the bone defect, including, for example, locating retention eyelets for optimal placement of fasteners (e.g., bone screws) into adequate bone or other tissue surrounding the defect, as well as locating the support rings so that the mosaic plates molded over those rings will optimally fill the bone defect with proper spacing and sizes of plates.
4. Digitally generating the mosaic plate arrangement so that the plates will be properly located with respect to the support rings.
5. Digitally generating the mold design based on the mesh support frame design and mosaic plate arrangement.
6. "Printing" the mesh support frame using the digital mesh support frame design (e.g., by selective laser sintering of titanium or titanium alloy).
7. "Printing" the mold negative using the digital mold design (e.g., using a fused filament fabrication "printer").
8. Fabricating a silicon mold from the mold negative.
9. Positioning the mesh support frame in the mold (e.g., in the manner described previously).
10. Molding the mosaic plates onto the support frame (e.g., using a hydraulic cement composition, such as those described previously) so that the support rings are encased within the mosaic plates.

The above additive manufacturing process provides a number of advantages, including rapid fabrication of customized implants for each patient, including various implant properties such as localized stiffness and/or localized flexibility, as well as the ability to fabricate implants with complex and/or irregular geometries (including complex curved surfaces). The implants are more structurally sound (resist deformation), and aesthetically pleasing following implantation. In addition, the implants will require minimal adjustment by the surgeon in order to achieve a proper fit.

Additive manufacturing techniques also allow for the fabrication of even more complex implant designs, including support frames with more robust internal support structures (i.e., the support structures which are located within the interior of the mosaic plates in the final implant). At the same time, these more robust support structures which further minimize the risk of plate fracture can be designed so as to actually use less metal (or other support frame material) compared to support frames fabricated in other ways.

Figure 33:
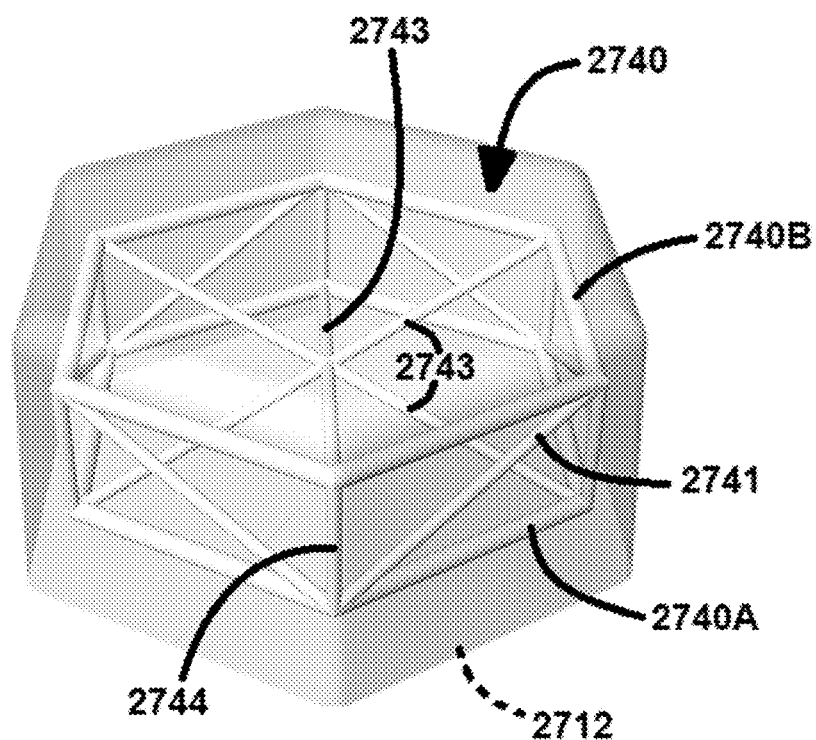
FIG. 33 depicts a schematic illustration of an alternative design of an internal support structure for a mesh support frame.

FIG. 33 schematically illustrates one such alternative design for the internal support structure for a mesh support frame, wherein a dual support ring comprising an hexagonal support cage (2740) is located within the mosaic plate (2712). Support cage (2740) can be used in place of any of the support rings (2040, 2340, 2440, 2540, 2640) described previously. The other portions of the support frame such as the connecting struts or pins and retention eyelets are omitted in FIG. 33.

Support cage (2740) can be provided in any of a variety of configurations and geometric shapes, and that shown is merely one possible embodiment contemplated by the inventors. Support cage (2740) comprises a pair of hexagonal support rings (2740A, 2740B) in a spaced-apart relationship. The support rings (2740A, 2740B) are similar to the previously described support rings (e.g., 2040), and are maintained in a vertical spaced-apart relationship by vertical supports (2744) extending between aligned vertices of the support rings (2740A, 2740B). Diagonal truss members (2741) are provided along the sides of the support cage (2740), as well as diagonally extending internal cross-members (2743), as shown. Thus, support cage (2740) is in the form of a hexagonal prism. Of course pentagonal and quadrilateral prism structures may be formed in the same way in order to replace the support rings in the previously described embodiments, and the support cages may be connected to one another by any of the connecting struts and/or connecting pins described above.

Figure 34:
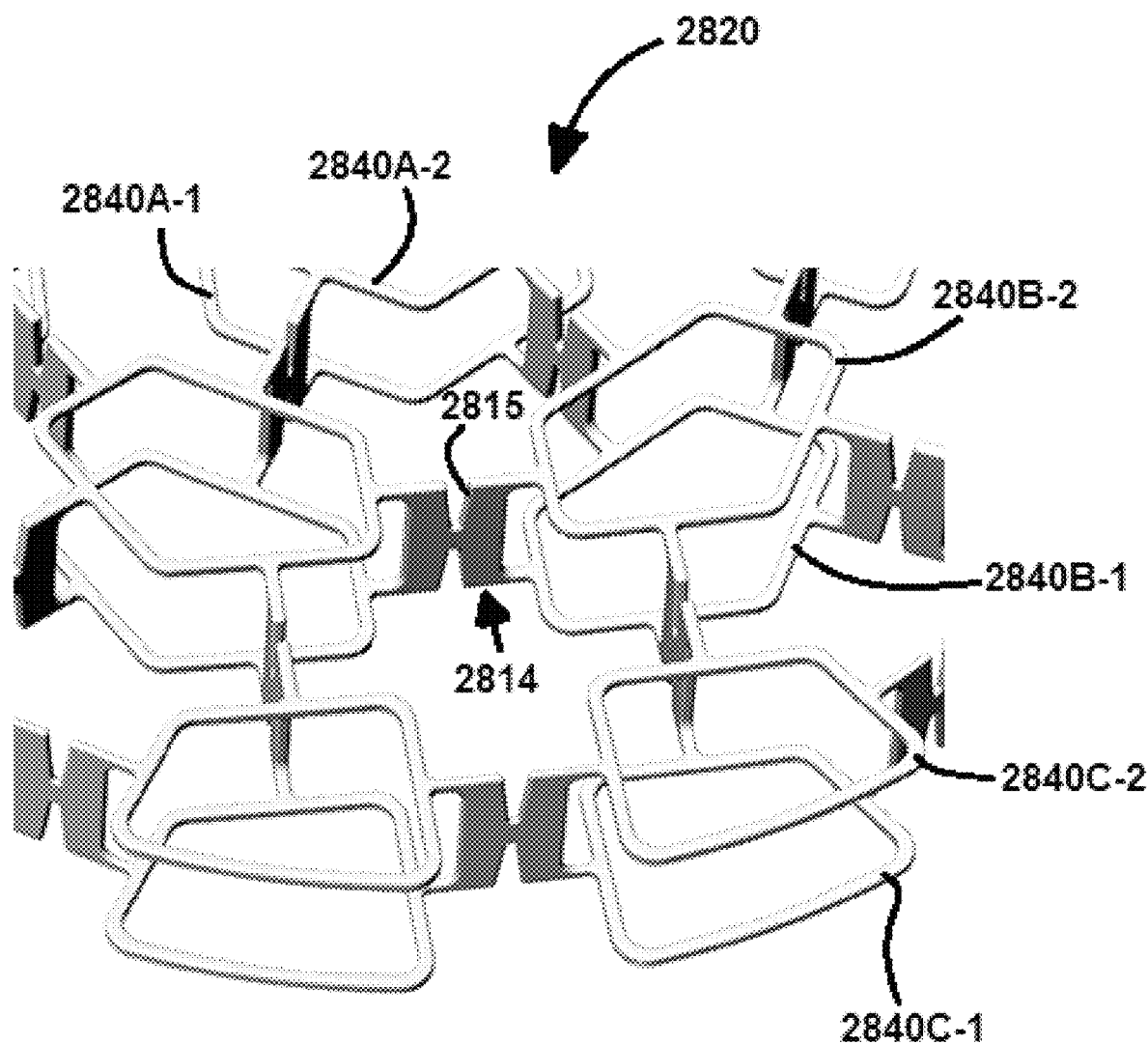
FIG. 34 depicts a perspective view of a portion of another embodiment of a support frame for a mosaic implant.

FIG. 34 illustrates a portion of yet another support frame (2820) which may be used in place of any of the previously described embodiments. Once again other portions of the support frame such as the connecting struts or pins and retention eyelets are omitted in FIG. 34.

Support frame (2820) is similar to support frame (2020) in FIG. 25. However, in place of individual support rings (2040), support frame (2820) has vertically spaced pairs of support rings (2840). Thus, the outer section of support rings includes vertically spaced and aligned pairs of support rings (2840C-1, 2840C-2). Similarly the middle section of support rings includes vertically spaced and aligned pairs of support rings (2840B-1, 2840B-2), and innermost support ring has vertically spaced and aligned pairs of support rings (2840A-1, 2840A-2). As also seen in FIG. 34, the individual support rings (2840) are thinner and not as wide as support rings (2040) in FIG. 25. In fact, the support frame (2820) provides the same strength and plate crack resistance as support frame (2020) of FIG. 25, but uses less material. This provides cost savings and reduced metal in the patient. Less metal implanted is desirable for a number of reasons, including the fact that metal will distort MRI scans, and implant weight is reduced.

The support rings (2840) are maintained in their vertical spaced-apart relationship by connecting struts (2814). Connecting struts (2814) not only connect and maintain the vertical spaced apart relationship of the support rings (2840) of each pair, but also serve to connect support ring pairs to adjacent support rings pairs, as shown. Connecting struts (2814) can be arranged to connect adjacent pairs of support rings (2840) in any of the variety of patterns previously described. Connecting struts (2814) are also H-shaped, and include a reduced-thickness deformation zone 2815 which remains between adjacent mosaic plates after the plates have been molded about support frame (2820).

Figure 36:
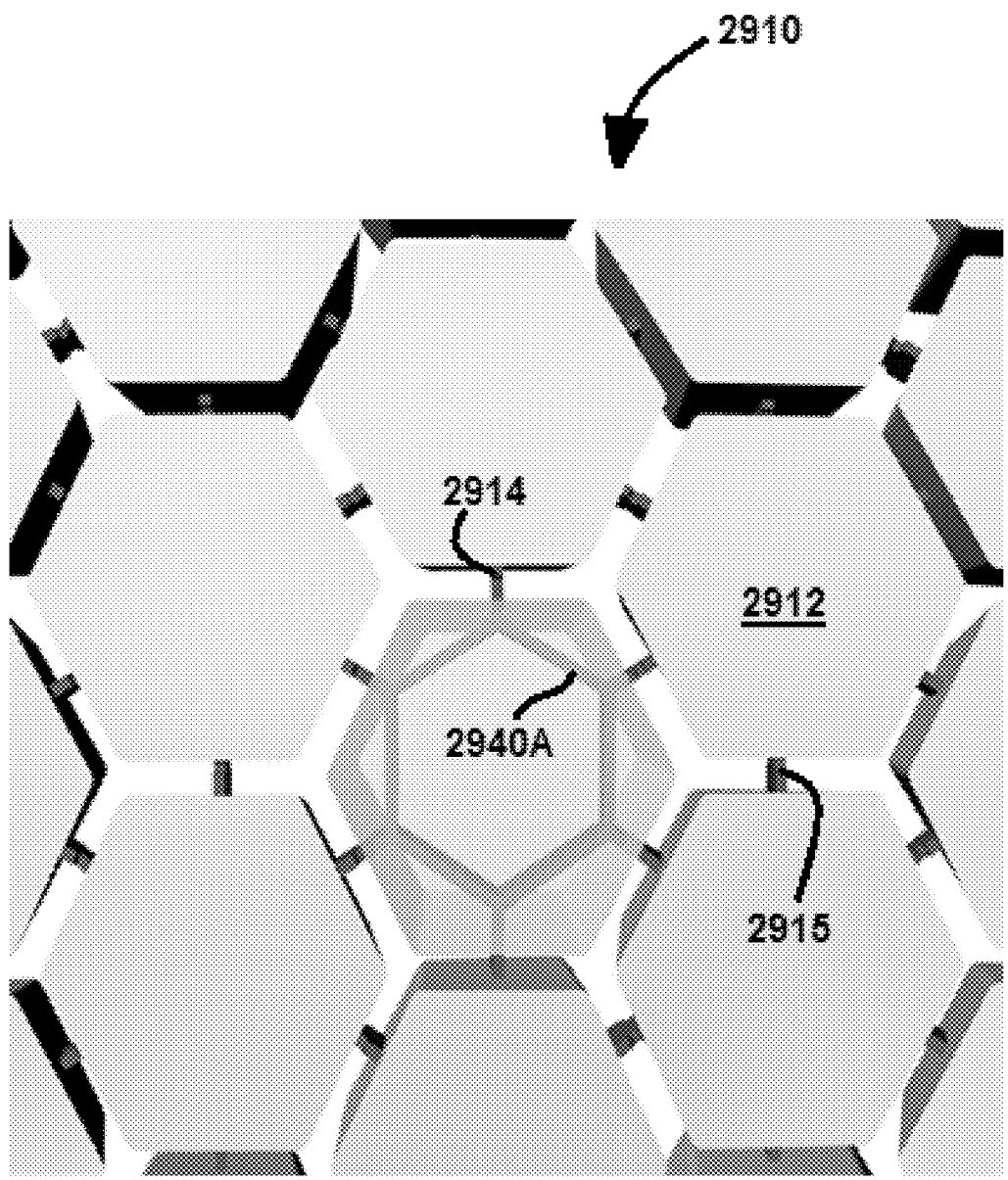
FIG. 36 depicts a top plan schematic view of a portion of an implant incorporating the support frame of FIG. 35, showing the orientation of the mosaic plates with respect to the internal support rings of the support frame.
Figure 37:
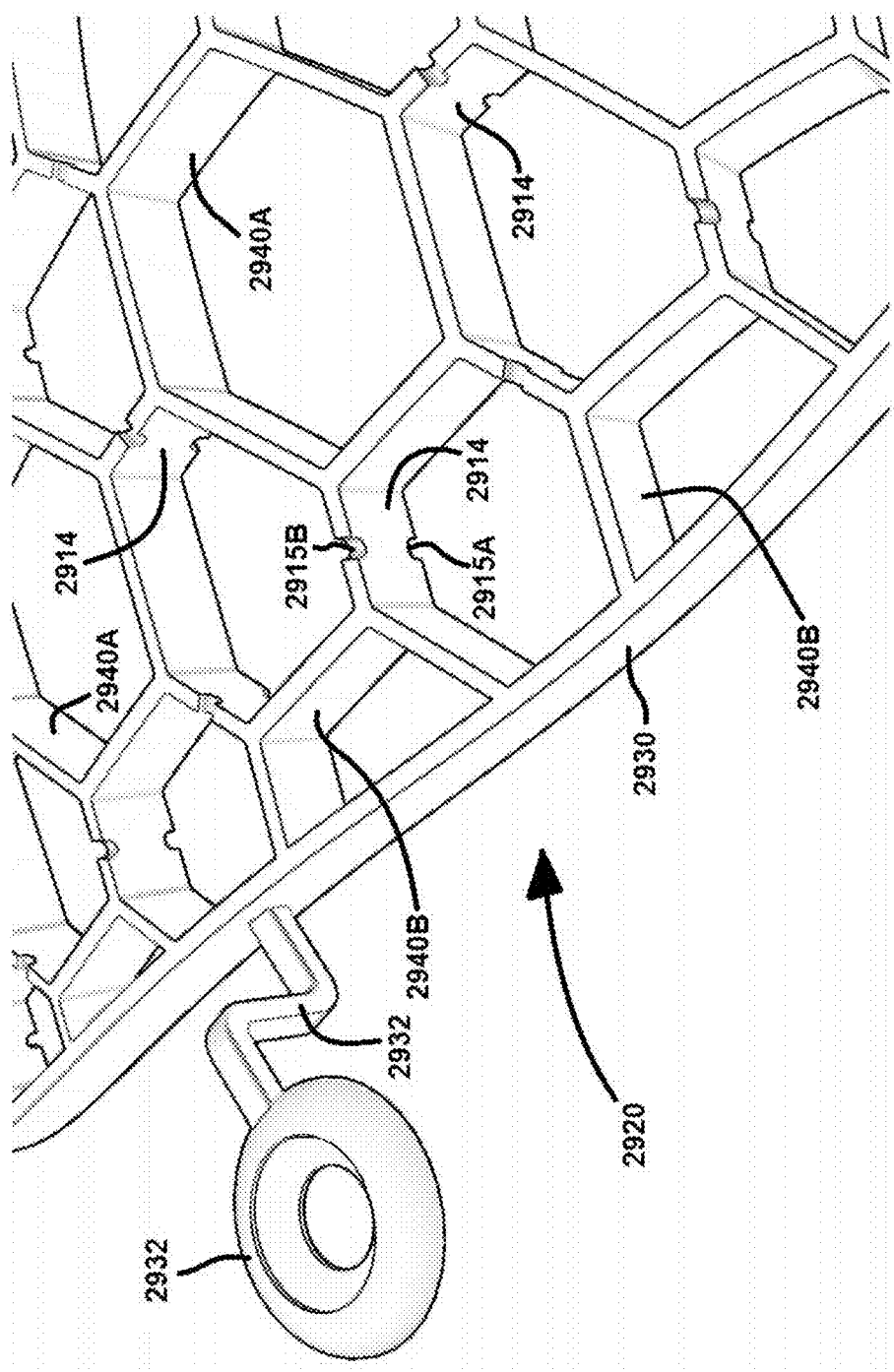
FIG. 37 depicts a perspective view of a portion of the support frame of FIG. 35.
Figure 38:
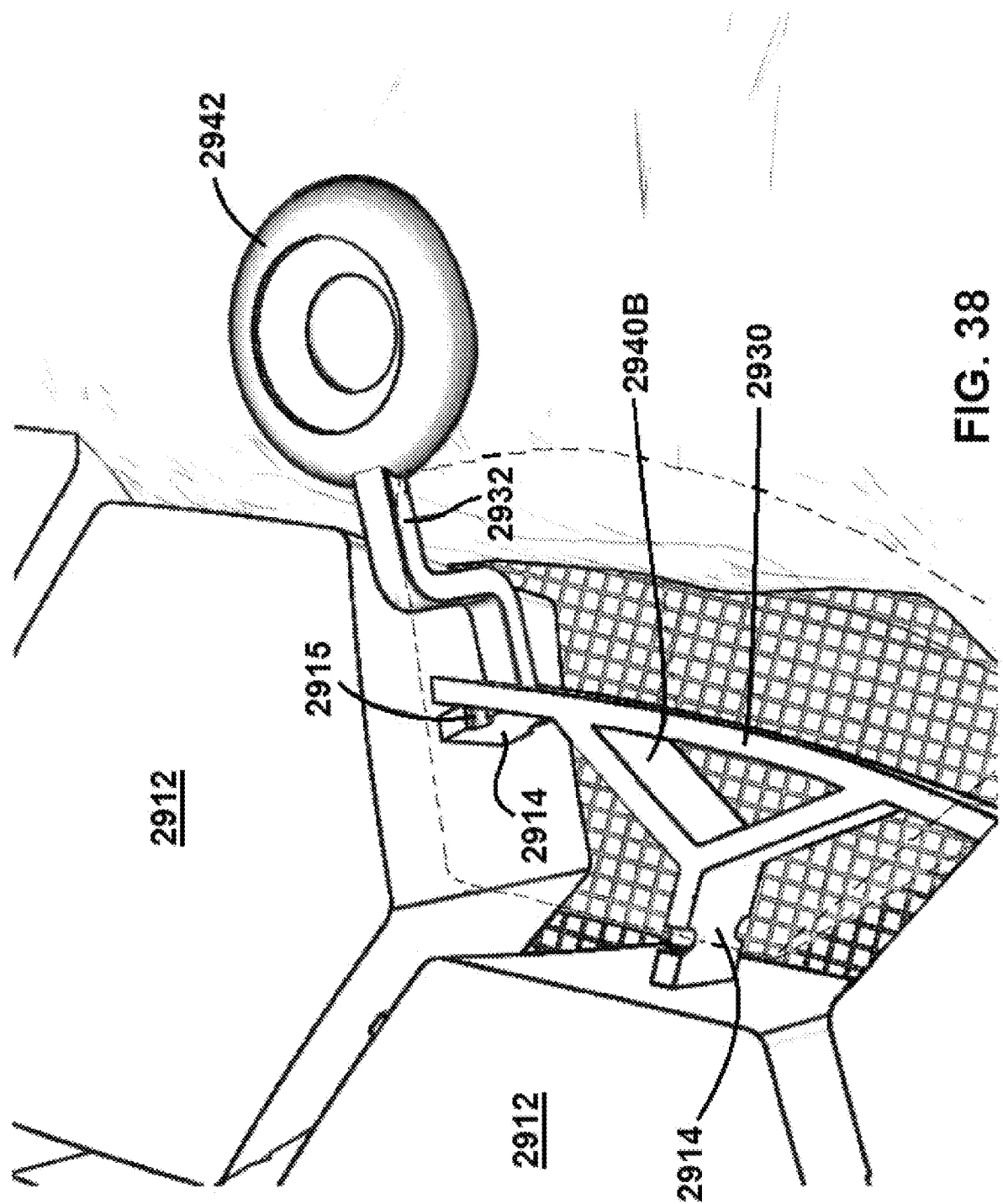
FIG. 38 depicts a perspective view of a mosaic implant fabricated using the support frame of FIG. 35, positioned within a bone defect in a patient, wherein one of the outermost mosaic plates has been removed in order to show the underlying structure.

FIGS. 35-38 depict a mesh support frame (2920) and implant (2910) according to another embodiment of the present invention. Support frame (2920) comprises a honeycomb-like arrangement of hexagonal support rings (2940), which are once again connected to one another by struts (2914). A rim (2930) also extends around the entire periphery of the support frame (2920). Since implant (2910) is customized to precisely match a particular bone defect in a patient, particularly when fabricated using additive manufacturing techniques, rim (2930) will be configured to match the size and shape of the bone defect such that the rim is spaced an appropriate distance from the edge of the defect following implantation. Thus, rim (2930) will often have an irregular shape, such as that shown in FIG. 35. Rim (2930) not only provides structural support to the implant, it also provides attachment points for retention arms (2932) (see FIG. 38). Rim (2930) also serves as the outermost wall of the support rings (2940) located about the periphery of the support frame, and the outermost mosaic plates are molded over portions of rim (2930), as seen in FIG. 38.

Retention arms (2932) extend from the outer periphery of the rim (2930), and are bent similar to the retention arms (2032) in the embodiment of FIG. 26. Retention eyelets (2942) are also provided at the distal ends of the retention arms, as shown, and are used to secure the implant (2910) in a patient. As best seen in FIGS. 37 and 38, the retention eyelets (2942) are also countersunk such that the head of a screw inserted therethrough will not extend above the upper surface of the retention eyelet (2942).

It should also be pointed out that the retention arms (2932) in the embodiment of FIGS. 35-38 are located so as to extend from the rim (2930) between adjacent mosaic plates (see FIG. 38). Thus, retention arms (2932) are attached to the rim (2930) at a portion of the rim which spans the gap between two adjacent support rings (2940B) (see FIG. 37). It will be understood, however, that the retention arms (2932) can be located on the rim (2930) so as to extend out of a mosaic plate, similar to the embodiment shown in FIG. 26.

Figure 35:
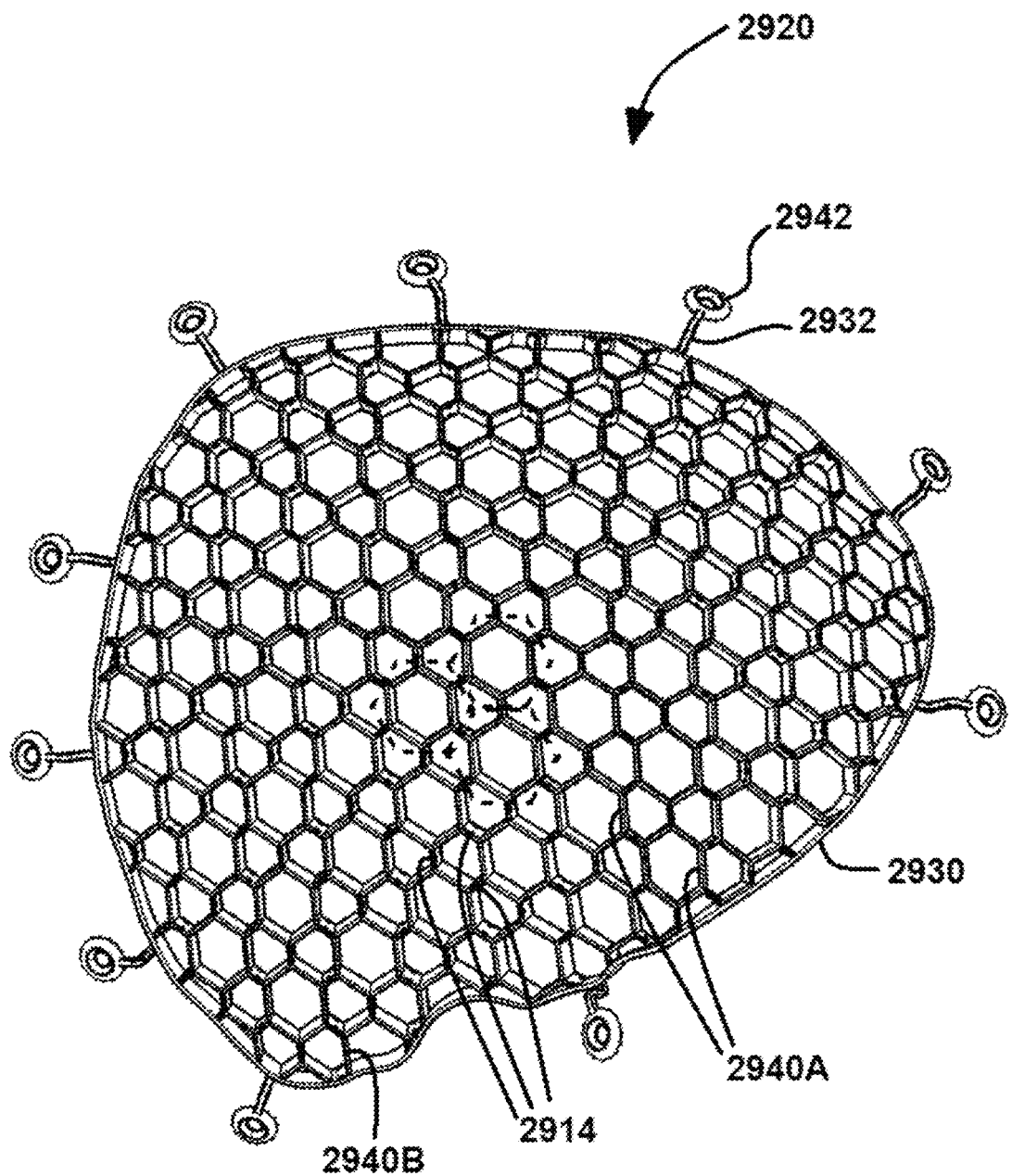
FIG. 35 depicts a perspective view of yet another embodiment of a support frame for a mosaic implant, wherein the support frame has been fabricated by additive manufacturing and is fabricated in a curved configuration as shown in order to produce a customized mosaic implant having a curvature designed for a particular patient's bone defect (in this instance, a cranial defect).

As will be noted in FIG. 35, the honeycomb structure comprises an array of regular hexagonal support rings (2940A), arranged in a series of staggered columns of spaced-apart support rings. Unlike the support mesh configuration shown in FIG. 25 where the struts extend between the centers of the sidewalls of adjacent polygonal support rings, however, the struts (2914) of the honeycomb support frame of FIG. 35 extend between the vertices of adjacent hexagonal support rings (2940A). Other than the support rings about the periphery of the support frame (2920), each hexagonal support ring (2940A) is connected to six adjacent support rings (2940A) in this manner. As a result, the each support ring (2940A) is surrounded by six hexagonally shaped open regions. As best seen in FIG. 37, deformation zones are also provided on struts (2914), here in the form of a reduced-thickness region (2915) provided by a notch (2915A) extending upwardly from the bottom surface of the support strut (2914), and a notch (2915B) extending downwardly from the upper surface of the support strut (2914). As before, the deformation zones are positioned so as to be located between adjacent mosaic plates in the final implant assembly (2910) (see FIG. 36).

About the periphery of honeycomb mesh support frame (2920), the outermost support rings (2940B) are truncated as necessary to provide the outer peripheral shape to match a patient's bone defect. In many instances this means that the outermost support rings (2940B) are not hexagonal, but rather are pentagonal, quadrilateral or triangular, depending on the amount of truncation. As mentioned previously, the rim (2930) thus provides the outer wall of the support rings (2940B), and also spans the gap between adjacent support rings (2940B), as best seen in FIG. 37. As with the embodiments shown in FIGS. 25-34, the support frame (2920) is also fabricated to have the desired curvature of the final implant (2910), since it is manufactured by an additive manufacturing technique such as selective laser sintering.

As described previously, the mosaic plates in, for example, the implant (2010) of FIG. 30 are molded about the support rings (2040) in alignment with the support rings—i.e., the sides of the plates are generally (or nearly) parallel to the sidewalls of the support rings. In contrast, the mosaic plates (2912) in the implant (2910) of FIGS. 35-38 are rotated approximately 30° with respect to the support rings (2940). This is best seen in FIG. 36. This arrangement also means that, even though the support struts (2914) extend between the vertices of adjacent hexagonal support rings (2940), in the final implant structure the struts (2914) extend out of the sidewalls of the mosaic plates, approximately orthogonal to the sidewall (see FIG. 38).

About the outer periphery of the fabricated implant (2910), the size and shape of the outermost mosaic plates are tailored as necessary to not only encase the outermost support rings (2940B), but also to ensure that the outermost plates provide the outer peripheral size and shape for the implant so as to precisely fit the patient's bone defect. The outermost mosaic plates are tailored by the appropriate design of the mold used in molding the plates onto the support frame. Like the embodiment shown in FIG. 28, the outermost mosaic plates on implant (2910) may be, for example, hexagonal, pentagonal or quadrilateral, depending on the particular shape of the desired implant. In some instances, the mosaic plates are simply truncated to the appropriate size and shape, similar to the truncation of certain outer plates (2212B) in FIG. 28.

However, in some instances the necessary truncation of an outer plate (2912B) would result in a plate which would not be sufficiently supported by the rim (2930) and support ring (2940B) about which the plate is molded (too little plate material positioned interiorly of the rim, or too much material outside of the rim). In these instances, rather than truncating the plate (2912B) too much, the inwardly adjacent plate is extended outwardly past the rim (2930) so as to provide an elongated plate. Once again this is similar to the extension of certain outer plates (2212B) in FIG. 28. As also seen on some of the outer plates (2212B) in FIG. 28, the sides of the extended plate, as well as those of the two adjacent outer plates may also be aligned with one another, as desired. In some embodiments, an inwardly adjacent plate will be extended to the outer perimeter of the implant (2910) when truncation of a corresponding outer plate (2912B) would result in more than 50% of that plate being located outside of the rim (2930) of the support frame.

In some embodiments it is also desirable to minimize the amount of exposed support frame, particular when the support frame is fabricated from a metal such as titanium or titanium alloy. Exposed metal, for example, can cause discomfort and interfere with imaging of the patient (e.g., MRI scanning). In order to reduce exposed metal surfaces, portions of the various implants described herein may be modified in order to facilitate the formation of a suitable covering material over the otherwise exposed metal surface. In one embodiment, the covering material comprises the same material used for the mosaic plates, particularly the hydraulic cement composition used for the plates. In fact, the covering can be applied as part of the molding process, with the molds configured such that the covering will be formed during the molding process.

The use of a covering material comprising the same material as the plates not only simplifies implant fabrication, but also can promote the formation and/or growth of new bone over exposed surfaces of the support frame when that material is osteoinductive and/or osteoconductive. As described previously, for example, the molds used to form the biocompatible plates over portions of the support frame can be configured such that a layer of the same material (e.g., a monetite cement) is formed over exposed portions of the support frame such as the exposed portion of the wire struts extending between adjacent plates. The cement covering the wire struts act as osteoconductive and/or osteoinductive bridges between the cement plates, facilitating the formation and/or growth of new bone between adjacent plates along the wire struts.

Figure 39:
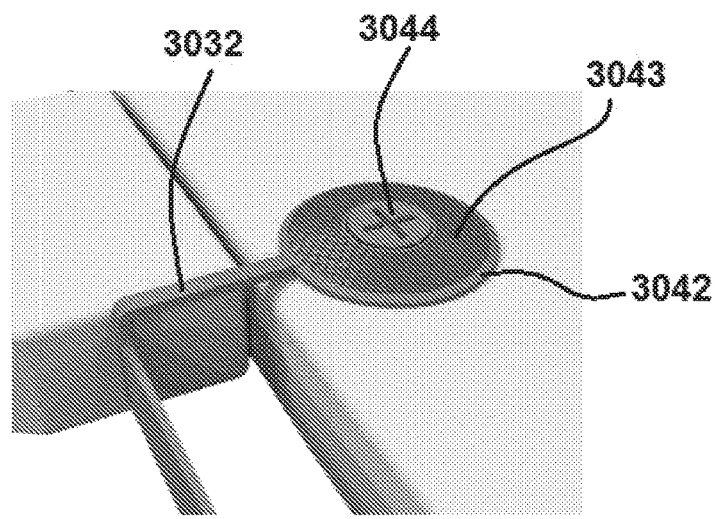
FIGS. 39-43 depict various embodiments of portions of support frames having, or configured to be covered with, a cement coating.

FIGS. 39-43 depict an additional technique for applying the biocompatible material of the plates over otherwise exposed metal surfaces of the support frame, in these instances the metal surfaces of the retention eyelets and retention arms connecting the eyelets to the support frame. In FIG. 39, retention eyelet (3042) includes a porous metal coating (e.g., porous titanium) (3043) applied to the upper surface of the eyelet surrounding the aperture which receives bone screw (3044). Such porous titanium coatings are commonly used, for example, in orthopedic implants (e.g., hip implants) and can be applied, for example, by plasma spray deposition. The porous titanium coating readily receives the cement, such that the area having the porous metal coating (3043) will be covered by the cement in the final implant. The configuration shown in FIG. 39 may be used with any of the implant structures described herein.

Figure 40:
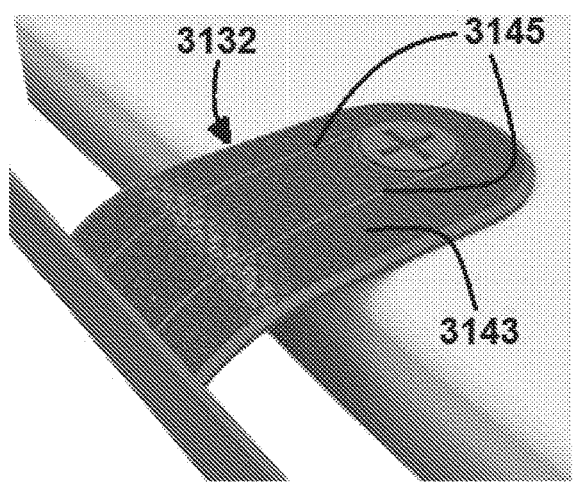
Figure 41:
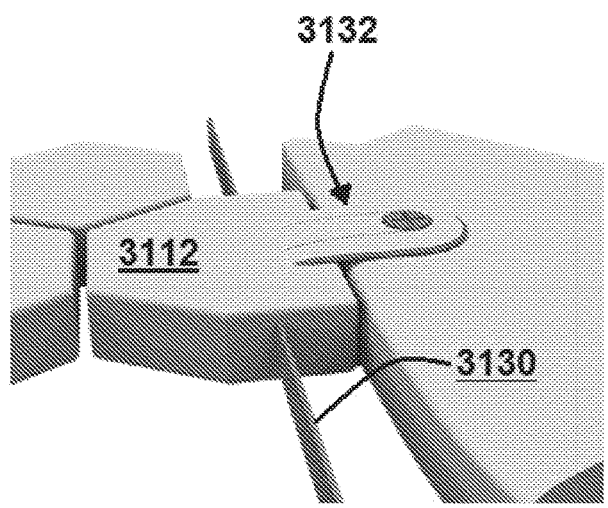
Figure 42:
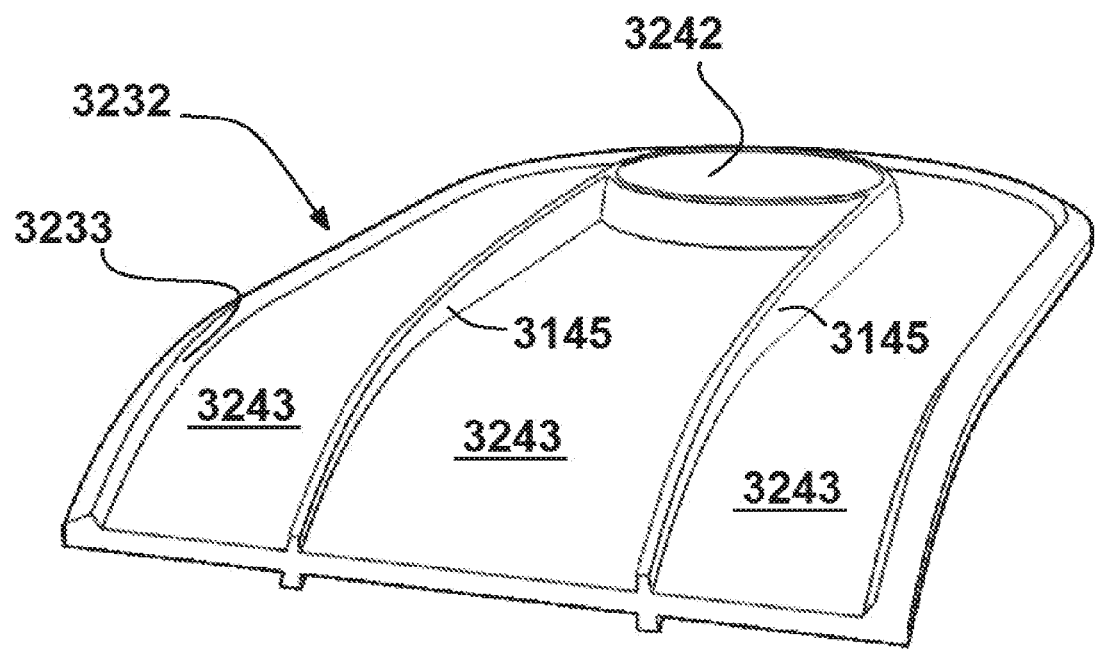

In the alternative arrangement shown in FIGS. 40 and 41 of an implant having a retention arm (3132) which is elevated with respect to the upper surface of the mosaic plate from which it extends, the retention arm has been purposefully made wider so as to provide an increased exposed surface area on top. The retention eyelet is also integral with the retention arm (3132), such that the eyelet is simply an aperture in the retention arm for receiving a bone screw or other fastener. The upper surface of the retention arm (3132) includes a porous metal coating (3143) other than a pair of ribs (3145) extending along the top of the retention arm as shown. The porous metal coating is covered by cement during the molding process, as seen in FIG. 41.

Figure 43:
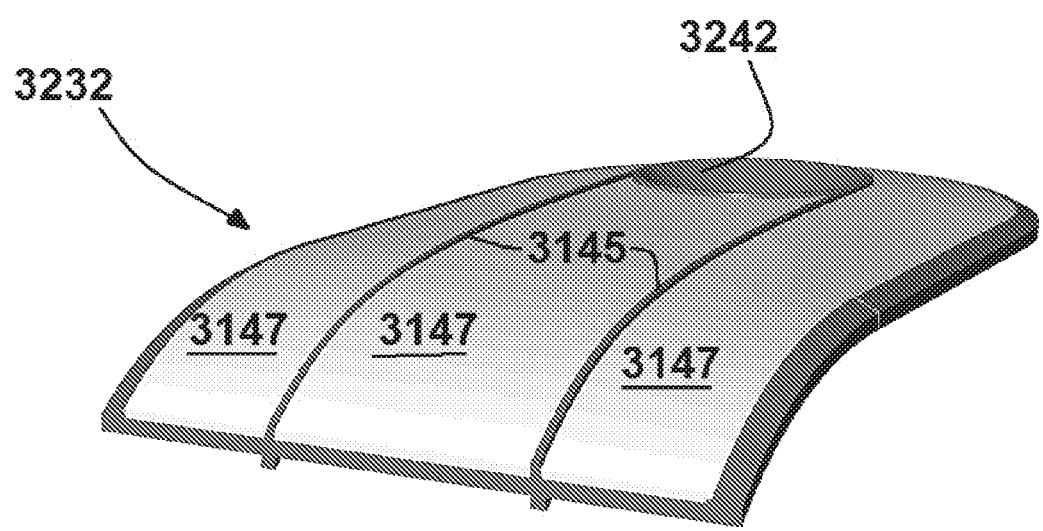

In place of using a porous metal coating to support a cement covering layer, exposed portions of the metal support frame can include one or more cavities for receiving cement or other biocompatible material therein, particularly the material used to form the mosaic plates. As seen in the alternative embodiment of a retention arm (3232) depicted in FIG. 42, instead of applying a porous metal coating, the upper surface of the retention arm (3232) includes one or more cavities for receiving hydraulically hardenable cement (or other suitable material). Thus, the upper surface of the retention arm (3232) has an upwardly extending wall (3233) around its periphery, as well as a pair of ribs (3145) which extend from the proximal edge of the retention arm (i.e., where the arm attaches to the rest of the support frame) to and around the retention eyelet (3242). The wall (3233) and ribs (3145) thus provide cavities (3243) for receiving the cement composition. FIG. 43 depicts the retention arm (3232) after the cavity (3243) has been filled with cement (3147).

Figure 46:
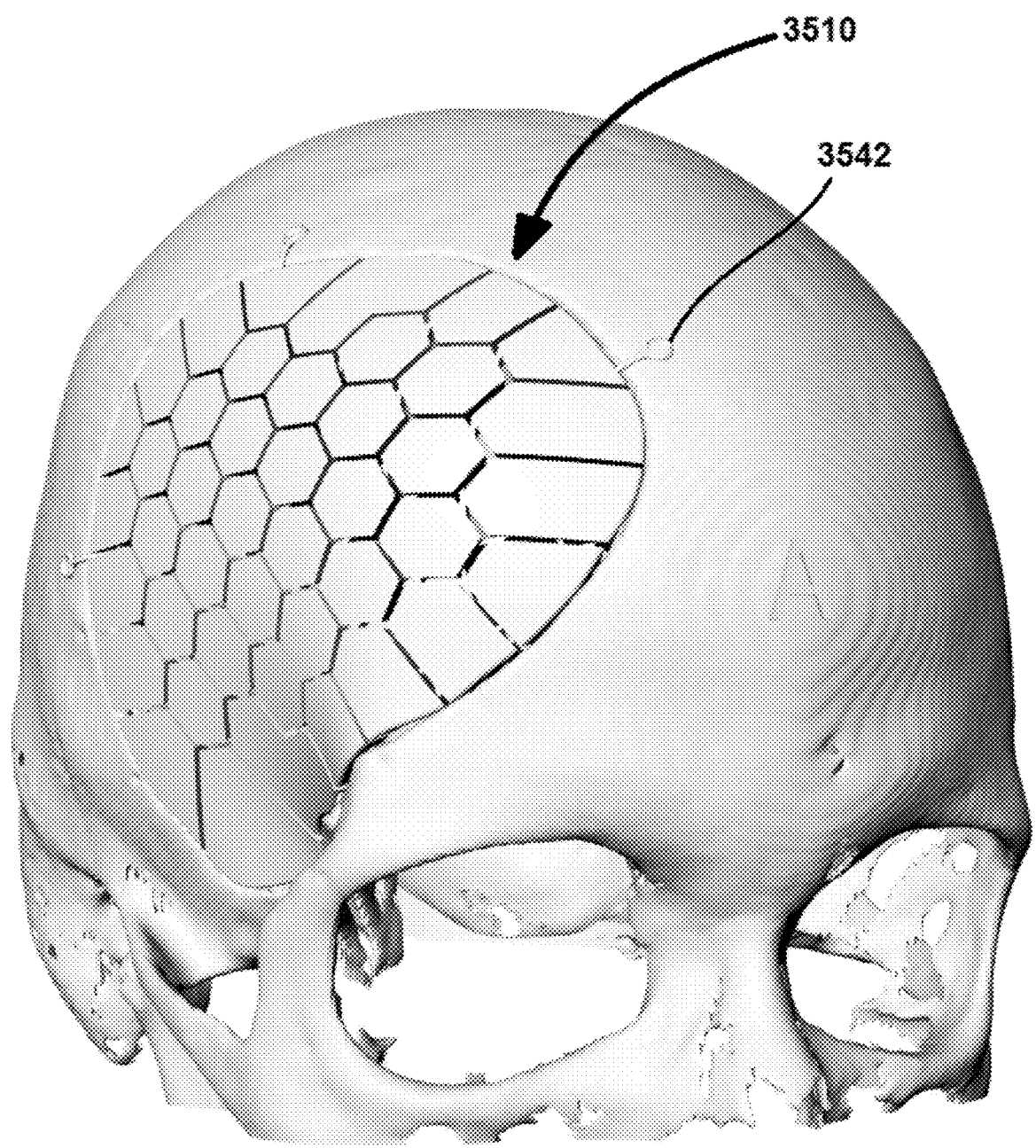
FIG. 46 depicts a schematic rendering of the implant of FIG. 44 implanted in a bone defect in a skull.

FIGS. 44-52 depict yet another alternative embodiment of a mosaic implant (3510), wherein FIG. 46 depicting the implant (3510) implanted in a bone defect in patient's skull. Implant (3510) is similar to implant (2910) described previously, and is specifically designed to match a particular cranial defect of a patient. Implant (3510) is fabricated as a rigid structure which is generally not deformable except for the retention arms (3532) which are configured to allow for some deformation at the time of implantation in order to position the retention eyelets (3542) flush against the surface of the bone surrounding a defect (e.g., as depicted in FIG. 46). Once again implant (3510) is not limited to use in cranial defects, and does not preclude the coupling of two or more implants (2010) in the manner previously described. Implant (2010) is also depicted as having an overall circular shape when viewed from the top (FIG. 25), however, this implant embodiment may be fabricated in various other shapes so as to precisely match a particular patient's bone defect.

Figure 44:
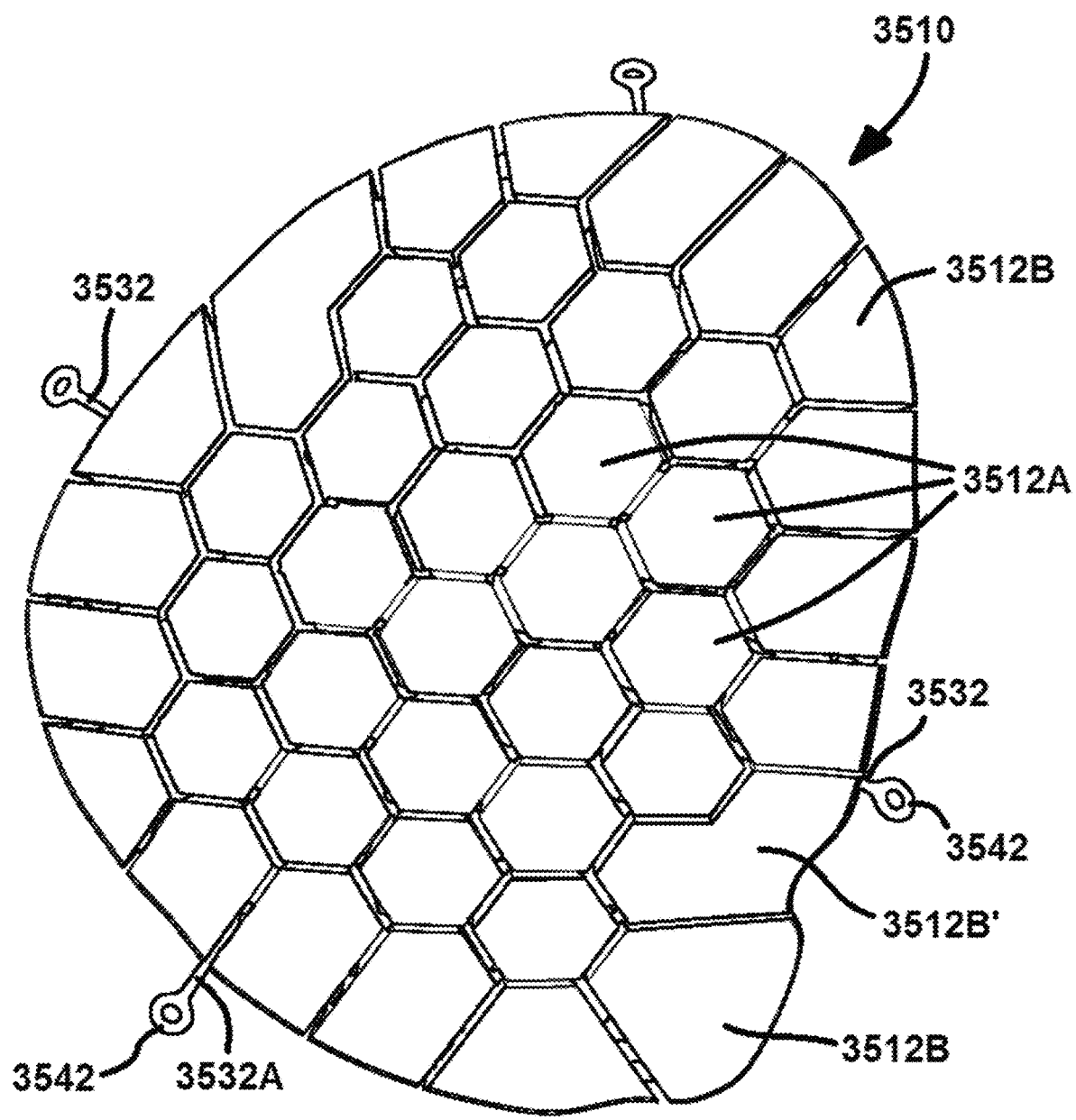
FIG. 44 depicts a top perspective view of another embodiment of a customized, rigid mosaic implant.
Figure 45:
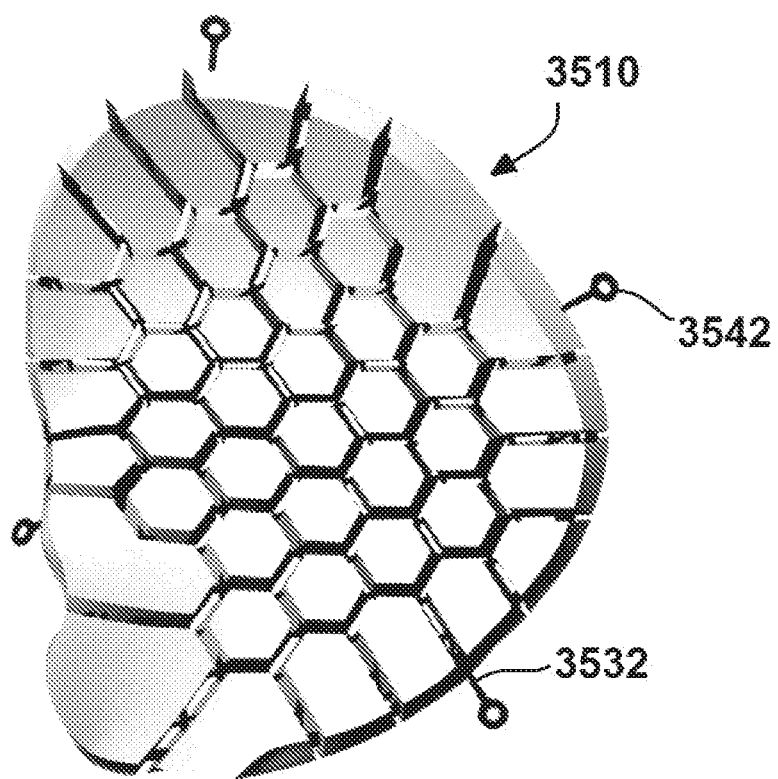
FIG. 45 depicts a bottom perspective view of the implant of FIG. 44.
Figure 47:
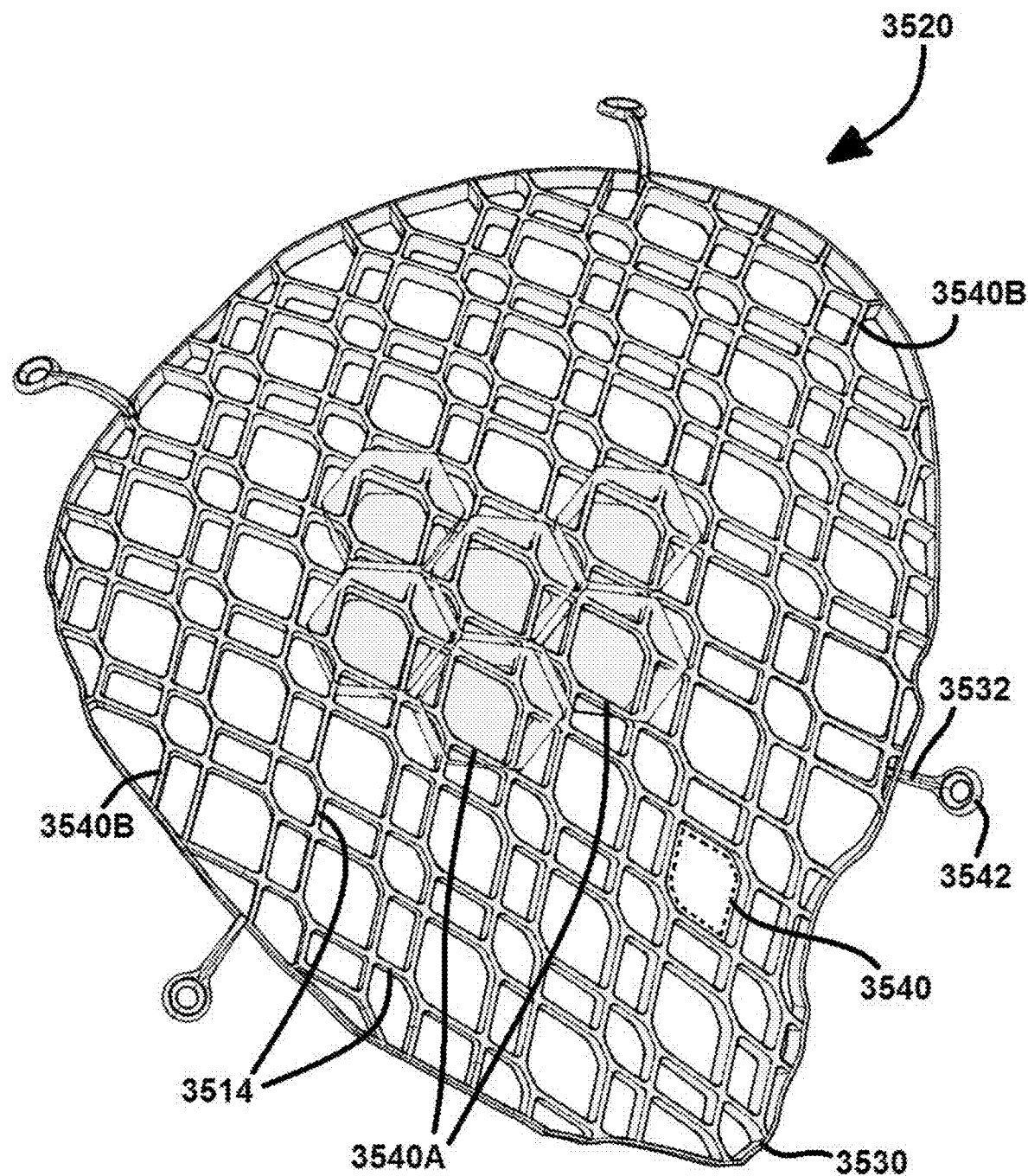
FIG. 47 depicts the support frame of the implant of FIG. 44, wherein several mosaic plates are shown semi-transparently.

As best seen in FIGS. 44 and 47, implant (3510) comprises a plurality of biocompatible mosaic plates (3512A, 3512B) which are interconnected with one another by a plurality of wire struts (3514) provided as part of a mesh support frame (3520). Each mosaic plate (3512A, 3512B) is connected to a plurality of the immediately adjacent mosaic plates by the wire struts (3514) which extend between and into adjacent mosaic plates (3512A, 3512B). Wire struts (3514) are in the form of struts having a thickness (i.e., height) greater than their width, as best seen in FIG. 47, thus providing greater rigidity to the support frame (3520). As further discussed below, each plate (3512A, 3512B) is connected to every adjacent plate by the wire struts (3514), however, the number of adjacent plates varies between three and five.

Implant (3510) includes a central array of identical hexagonal plates (3512A) arranged similarly to the hexagonal plates of the embodiments shown in FIGS. 1 and 28. In the particular embodiment shown, the central plates (3512A) are in the form of regular hexagons (hexagons having sides of equal length), with each central plate (3512A) spaced equally from each adjacent central plate (3512A) by the same distance. An outer ring of variously shaped (i.e., non-identical) plates (3512B) is arranged about the outer perimeter of the implant (3510), surrounding the central plates (3512A). Since the periphery of a bone defect (e.g., a cranial defect) is usually not a perfect circle, oval or other geometric shape, it is often necessary to provide an irregular outer perimeter shape for the implant. Thus, as in previous embodiments, the shape and size of the outer perimeter of implant (3510) can be customized, for example, by controlling the depth of each plate (3512B) of the outermost ring of plates, and/or controlling the shape and arrangement of each of those plates (3512B) in order to match a particular defect in a specific patient. Thus, the outer perimeter (i.e., the outer edge of the implant in FIG. 44) of the outer plates (3512B) is typically not a straight line, but rather is curved to match the contours of a particular patient's defect in need of treatment.

Figure 48:
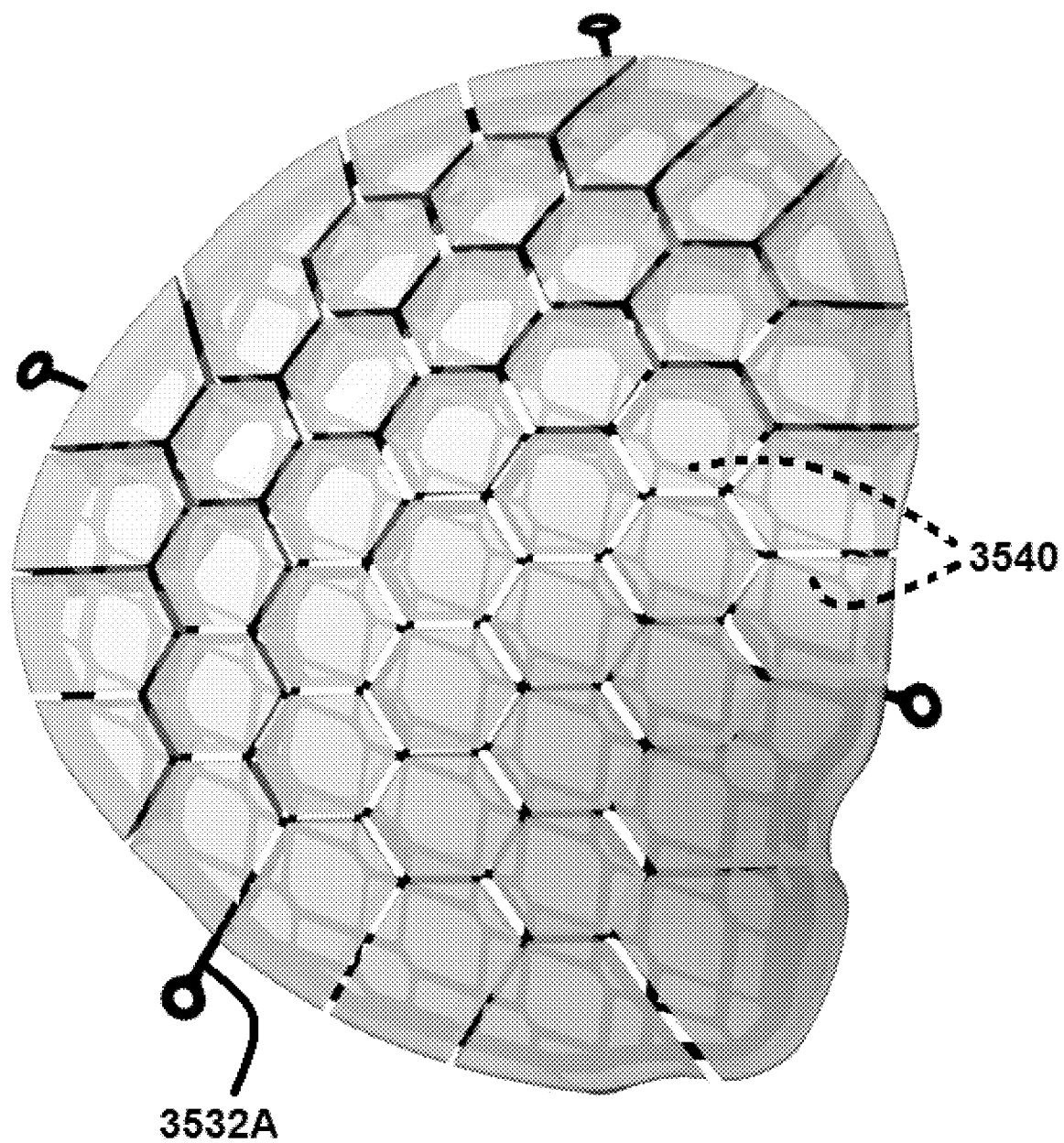
FIG. 48 is the same view as FIG. 44, wherein the mosaic plates are depicted semi-transparently.

While the internal support frame within implant (3510) may be configured similarly to that shown in FIGS. 1 and 2, a support frame structure is similar to that shown in FIGS. 35-38 is used in the implant (3510). Thus, the support frame includes internal hexagonal support rings (3540A) in each of the central plates (3512A), with struts (3514) extending between adjacent plates (see FIG. 47). Hexagonal support rings (3540B) are also provided in the majority of the outer plates (3512B), as best seen in FIG. 48 wherein the plates are depicted semi-transparently so that that the internal portions of the support frame (3520) are visible. Thus, like the implant of FIGS. 25 and 26, support rings (3540) have replaced the eyelets (240) of the mosaic implant shown in FIG. 1.

Support frame (3520) comprises a modified honeycomb-like arrangement of hexagonal support rings (3540) connected to one another by struts (3514). A rim (3530) also extends around at least a portion of the periphery of the support frame (3520). Since implant (3510) is customized to precisely match a particular bone defect in a patient, particularly when fabricated using additive manufacturing techniques, rim (3530) will be configured to match the size and shape of the bone defect such that the rim is spaced an appropriate distance from the edge of the defect following implantation. Thus, rim (3530) will often have an irregular shape, such as that shown in FIG. 47. Rim (3530) not only provides structural support to the implant, it also provides attachment points for retention arms (3532) (see FIG. 38). Rim (3530) also serves as the outermost wall of the support rings (3540) located about the outer periphery of the support frame, and the outermost mosaic plates are molded over portions of rim (35), as seen in FIG. 48.

Figure 49:
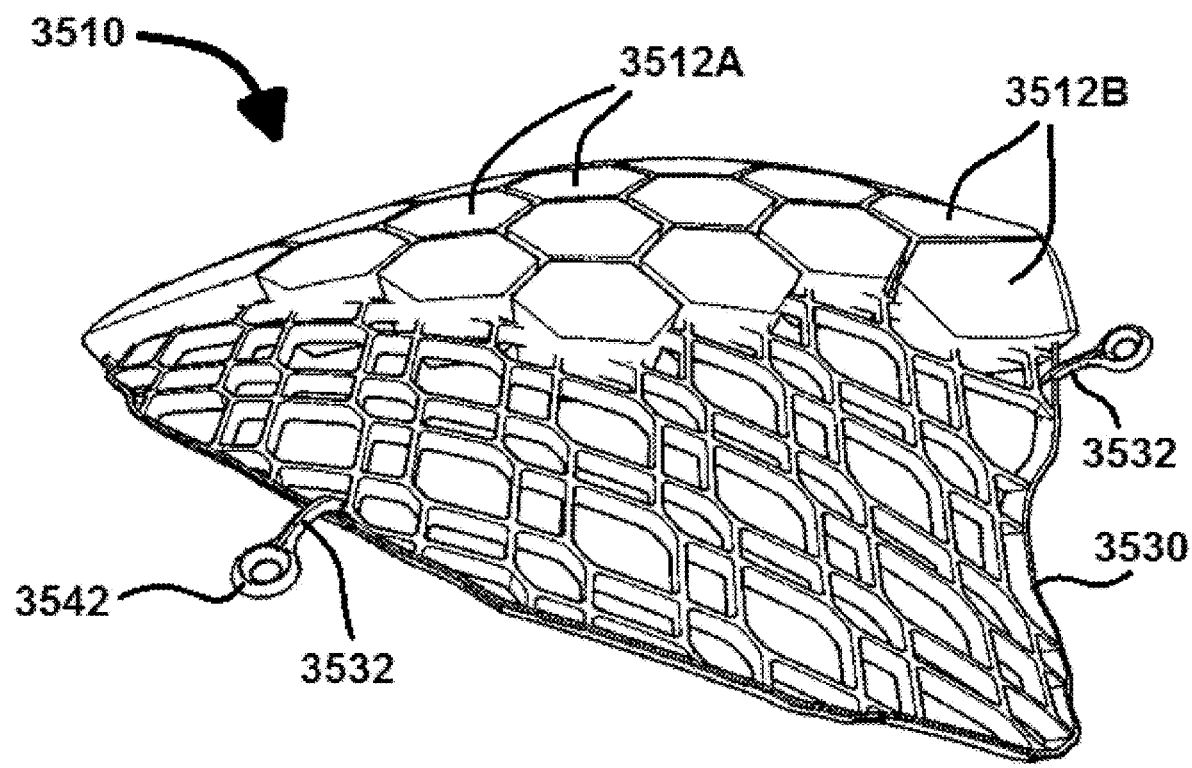
FIG. 49 depicts a side view of the implant of FIG. 44 wherein a portion of the mosaic plate have been removed.

Retention arms (3532) extend from the outer periphery of the rim (3530), with retention eyelets (3542) provided at the distal ends of the retention arms for securing the implant (3510) in a patient. Retentions arms (3532) are angled similarly to the retention arms (2032) in the embodiment of FIG. 26, and thus extend upwardly and outwardly from the rim (3530). However, the particularly configuration of each retention arm (3532) can be different in order to match the orientation of bone surrounding the site of implantation in a patient. In general, retention arms are configured so that the under surface of the associated eyelet (3542) will lie flush against the surface of a portion of the bone surrounding a defect, particular at a location through which a bone screw or other fastener can be driven into a sufficient thickness of bone for secure attachment. As best seen in FIGS. 47 and 49, the retention eyelets (3542) are also countersunk such that the head of a screw inserted therethrough will not extend above the upper surface of the retention eyelet (3542).

Each of the retention arms (3532) can be located so as to extend from the rim (3530) either between adjacent mosaic plates or out of a mosaic plate. In the depicted embodiment, one of the retention arms (3532A) is attached to the rim (3530) at a portion of the rim which spans the gap between two adjacent support rings, while the other retention arms (3532) are located on the rim (3530) so as to extend out of a mosaic plate, similar to the embodiment shown in FIG. 26.

Figure 50:
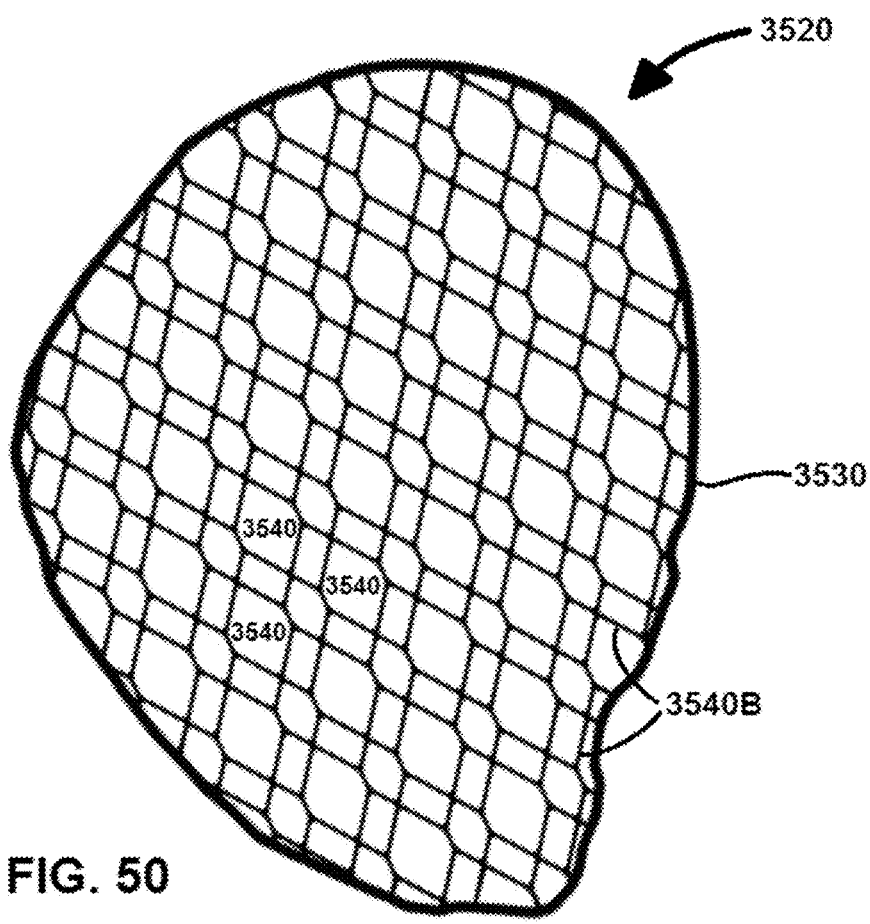
FIG. 50 depicts a top plan view of the mesh support frame used in the implant of FIG. 44, wherein the retention arms and retention eyelets are omitted.

FIG. 50 depicts the support frame (3520) with the retention arms and retention eyelets omitted for purposes of clarity. The modified honeycomb structure of support frame (3520) comprises an array of irregular hexagonal support rings (3540A), arranged in a series of staggered rows of spaced-apart support rings. Unlike the regular hexagonal support rings (2940A) (equilateral and equiangular) of the embodiment shown in FIG. 35, support rings (3540A) have an irregular hexagon shape (with rounded interior corners, as further explained below). However, although they are in the shape of irregular hexagons, support rings (3540A) are parallelogons. A parallelogon is a polygon shaped such that a plurality of such polygons can be fitted together along their sides (i.e., tiled) so as to fill a plane. Accordingly, opposite sides of the hexagonal support rings (3540A) are parallel and have the same length. In the particular embodiment shown, the four long sides of each hexagonal support ring (3540A) have the same length.

Unlike the support mesh configuration shown in FIG. 25 where the struts extend between the centers of the sidewalls of adjacent polygonal support rings, the wire struts (3514) of the support frame (3520) extend between the vertices of adjacent hexagonal support rings (3540A). Other than the support rings about the periphery of the support frame (3520), each hexagonal support ring (3540A) is connected to four adjacent support rings (3540A) by a pair of wire struts (3514) (a total of eight wire struts extending from each support ring). At the two vertices (3541) whereat the hexagonal support ring (3540A) has the smallest included angle (e.g., less than 90 degrees), two wire struts (3514) extend to a pair of adjacent support rings. At the other four vertices only a single wire strut extends to an adjacent support ring. The support rings (3540A) of any row, however, are not directly connected to one another by the struts (3514). Instead, each support ring (3540A) is connect to the pair of adjacent support rings in the two adjacent rows. As a result, the each support ring (2940A) is surrounded by an alternating series of four hexagonally shaped open regions, and four rectangular shaped open regions, as best seen in the enlarged view of FIG. 51.

Figure 51:
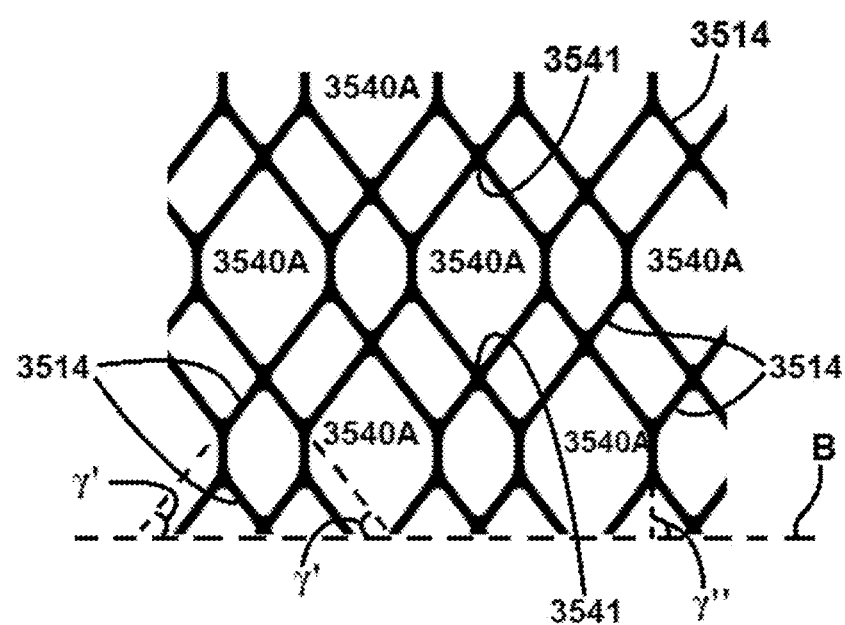
FIG. 51 depicts an enlarged top plan view of portion of the support frame of FIG. 50.

As best seen in the enlarged view of FIG. 51, the interior corners of each of the vertices in the wire mesh is rounded rather than having sharp angles, Rounding of the vertices whereat the wire segments forming the support rings and the wire struts meet adds additional strength and rigidity to the support frame (3520).

Mesh support frame (3520) is, in one embodiment, manufactured using an additive manufacturing process such as selective laser melting ("SLM"). In SLM, however, complex designs often require complicated support structures, particularly when the design calls for structural features that extend at an angle of less than 45 degrees with respect to the build plate. However, by arranging the support rings (3540) in the manner shown in FIGS. 50 and 51, with the wire struts extending between adjacent vertices of the irregular hexagonal support rings (3540), the wire mesh structure is self-supporting during SLM fabrication. This self-supporting aspect of the wire mesh is provided by the fact that the repeating mesh configuration depicted in FIG. 51 can be formed on an SLM build plate with all of the wire segments of the mesh (support rings and wire struts) angled with respect to the build plate more than 45 degrees. For example, from an imaginary planar base (B) (i.e., the plane of an SLM build plate), all of the wire segments forming wire struts (3514) or a side of a hexagonal support ring (3540A) are angled with respect to the base (B) at an angle ($\gamma'$) of about 50-55 degrees or at an angle ($\gamma''$) of about 90 degrees (i.e., they are all greater than 45 degrees). It will be understood, however, that the wire mesh structure of the support frame can have a different configuration than depicted in FIG. 51 but still be self-supporting. The self-supporting nature of the wire mesh structure of the support frame means that a support structure for the mesh as it is "printed" on an SLM build plate is not required during SLM (but will generally be required for the outer rim when the support frame is fabricated as a unitary structure via SLM or similar additive manufacturing process).

The repeating mesh structure shown in FIG. 51 extends throughout the entirety of the support frame (3520), bounded by outer rim (3530) in the shape of a particular defect. Once again, this arrangement provides for considerable customization of the implant, including the ability to conform the implant to a variety of curved surfaces. For example, FIG. 49 depicts implant (3510) curved so as to conform to a portion of a patient's skull (as also seen in FIG. 46). The repeating nature of the mesh structure also facilitates fabrication of an implant (3510) wherein the mosaic plates are evenly spaced from one another, along all sides, throughout the entirety of the implant. This not only encourages even growth of new bone between adjacent mosaic plates, it also adds to the strength and rigidity of the implant. In addition, like previous embodiments, since implant (3510) is custom fabricated for a particularly patient, it can be made in a rigid form, precisely matching a bone defect and the surrounding bone surfaces.

About the periphery of mesh support frame (3520), the outermost support rings (3540B) are truncated as necessary to provide the outer peripheral shape to match a patient's bone defect. In many instances this means that the outermost support rings (3540B) are not hexagonal, but rather are pentagonal, quadrilateral or triangular, depending on the amount of truncation (with an outer edge curved as necessary to match the shape of a particular bone defect). As mentioned previously, the rim (3530) thus provides the outer wall of the support rings (3540B), and also spans the gap between adjacent support rings (3540B), as best seen in FIG. 47. As with the embodiments shown in FIGS. 25-34, the support frame (3520) is also fabricated to have the desired curvature of the final implant (3510), and is manufactured by an additive manufacturing technique such as selective laser melting.

Figure 52:
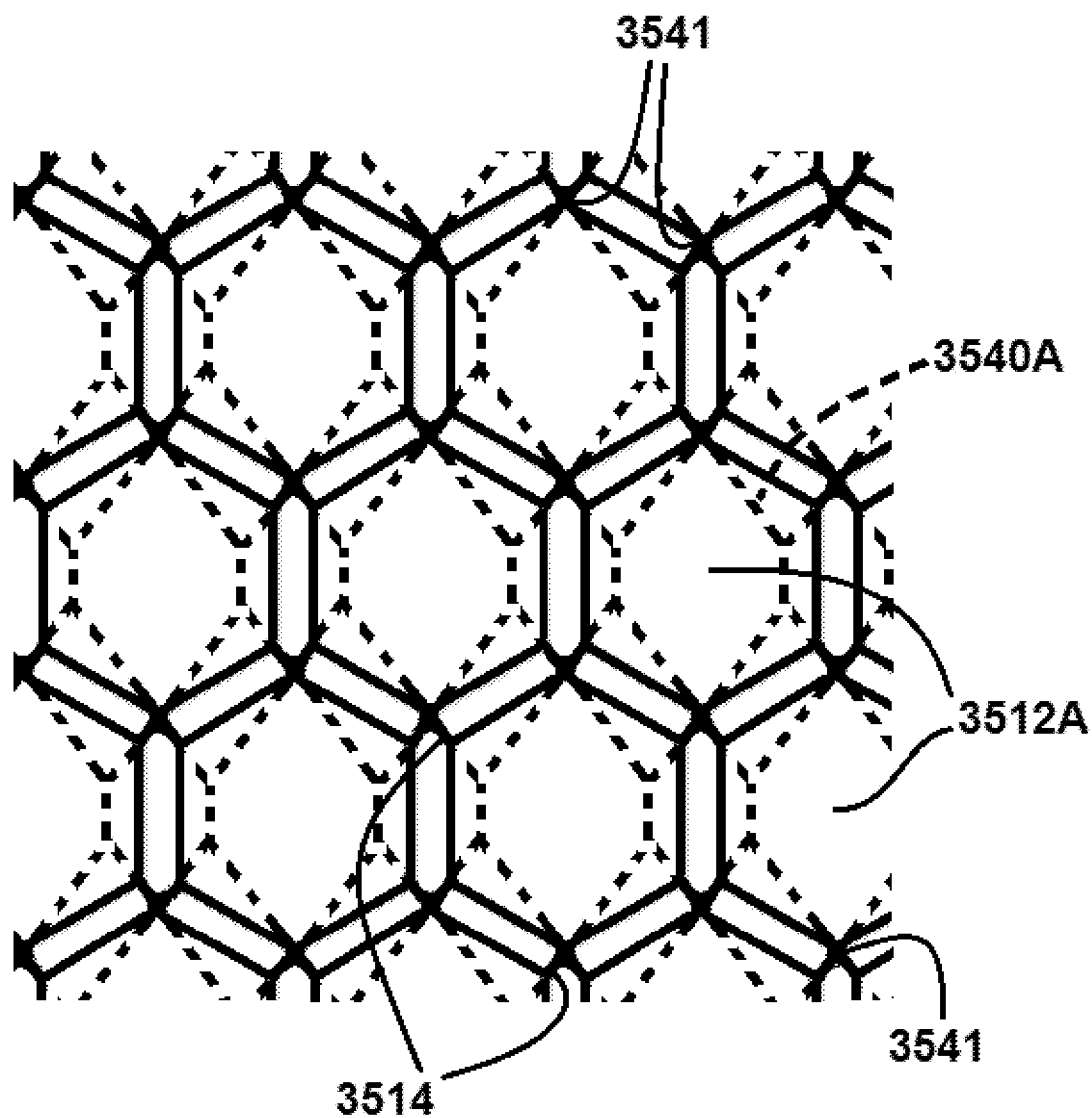
FIG. 52 depicts an enlarged top view of a portion of the implant of FIG. 44, wherein the mosaic plates are depicted semi-transparently.

As with the previously described embodiments, the mosaic plates (3512) are molded about the support rings (3540). In this instance, the central plates (3512A) are regular hexagons (when viewed from the top or bottom), and have tapered sidewalls as previously described with respect to other embodiments. Central plates (3512A) are molded about the support rings (3540A) in partial alignment therewith—i.e., two sides of the plates are generally (or nearly) parallel to the short sides of the irregular hexagon support rings (3540A). However, the remaining sides are not parallel to the sides of the support rings (3540A) due to the irregular hexagon shape of the support rings (3540A). Accordingly, the wire struts (3514) extend between adjacent central mosaic plates (3512A) only at the vertices of these plates. As best seen in FIG. 52, portions of the two vertices (3541) are located at corners of the plates (3512A), whereat a hexagonal support ring (3540A) has the smallest included angle. Thus, while the interior edge of each support ring (3540A) at the narrow angle vertices (3541) is located entirely within the plate (3512A), an outermost portion of the vertices (3541), specifically the intersection of the narrow angle vertices (3541) and a pair of struts (3514) extending to adjacent support rings, is located slightly outside of the plate (3512A). (In other words, a portion of the center of each "X" forming vertices (3541) is located slightly outside of the plate.) This arrangement provides additional rigidity to the implant (3510).

About the outer periphery of the fabricated implant (3510), the size and shape of the outermost mosaic plates are tailored as necessary to not only encase the outermost support rings (3540B), but also to ensure that the outermost plates provide the outer peripheral size and shape for the implant so as to precisely fit the patient's bone defect. The outermost mosaic plates are tailored by the appropriate design of the mold used in molding the plates onto the support frame. Like the embodiment shown in FIG. 28, the outermost mosaic plates of implant (3510) may be, for example, hexagonal, pentagonal or quadrilateral, depending on the particular shape of the desired implant (with one curved side, as necessary to match a particular bone defect). Like implant (2110) shown in FIG. 27, for example, the shape and size of the outer perimeter can be readily customized during fabrication by controlling the depth of each outer plate (3512B), while still maintaining the same distance between adjacent sides of the plates (3512A, 3512B).

In addition, like the embodiment shown in FIGS. 35-38, in some instances the necessary truncation of an outer plate (3512B) to match a particular defect will result in a plate which is not sufficiently supported by the rim (3530) and support ring (3540B) about which the plate is molded. In these instances, rather than truncating a plate (3512B) too much, the inwardly adjacent plate and/or an adjacent outer plate (3512B) is extended so as to provide an elongated and/or widened plate (e.g., plate (3512B') shown in FIG. 44.

As with previously described embodiments, the internal support rings (3540A, 3540B, due to their increased size (including their thickness) as well as their being shaped to match the shape of the mosaic plates, provide greater support and resistance to cracking of the plates (3512) as compared to the eyelets (240), not only during fabrication, adjustment and placement of the implant but also after implantation. At the same time, since support rings (3540A, 3540B) have an open interior region, they do not add nearly as much weight or cost as a solid support plate would.

The biocompatible mosaic plates (3512A, 3512B) of implant (3510) can be composed of any of a variety of the resorbable and/or stable (i.e., non-resorbable) biocompatible materials described previously herein. In one particular embodiment, mosaic plates (3512A, 3512B) comprise any of the previously described hydraulic cement compositions (e.g., predominantly monetite), and a molding process is used to mold the mosaic plates onto the mesh support frame (3520).

Figure 53:
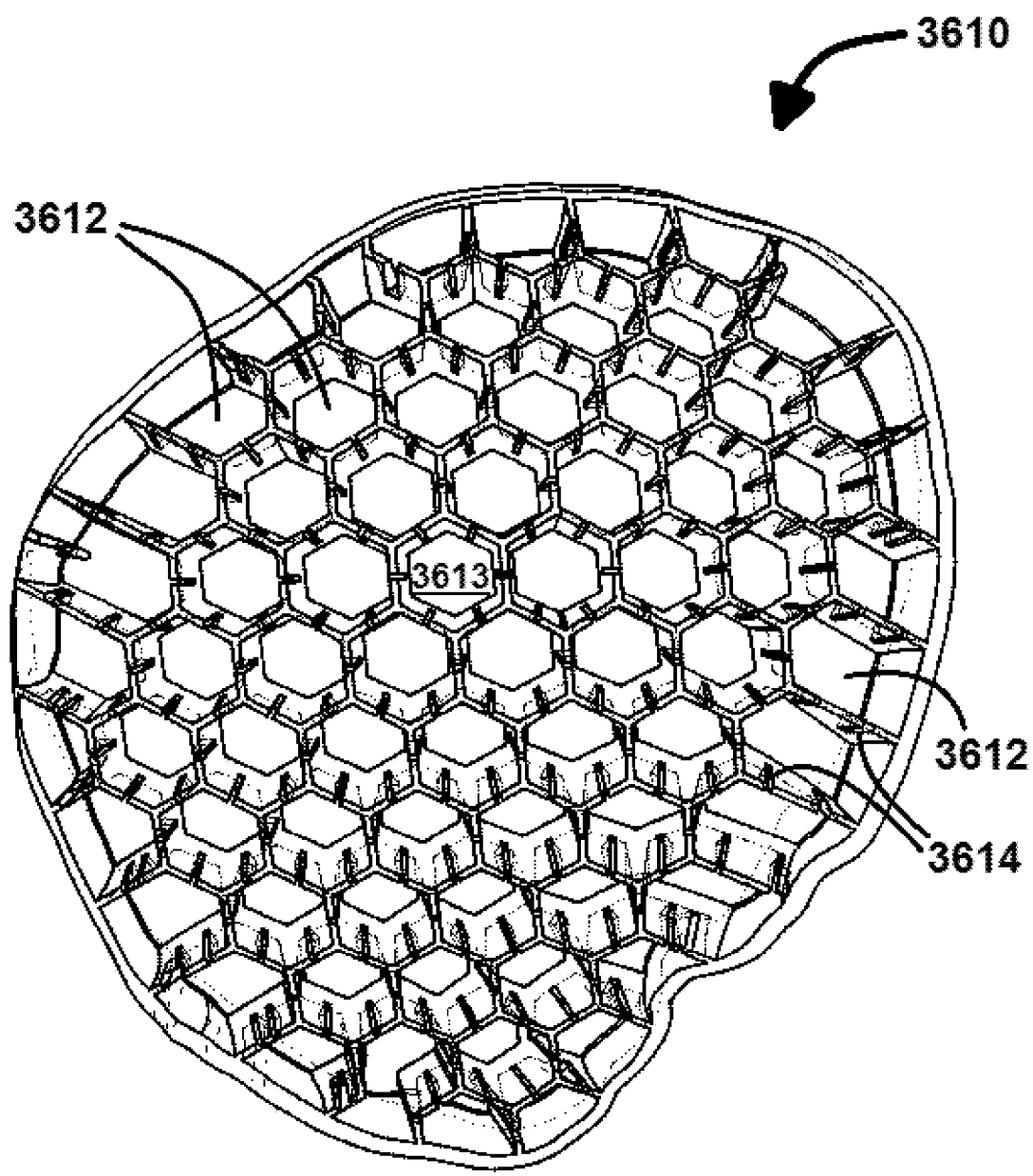
FIG. 53 depicts a top view of a mold used to form an implant similar to that shown in FIG. 44.
Figure 54:
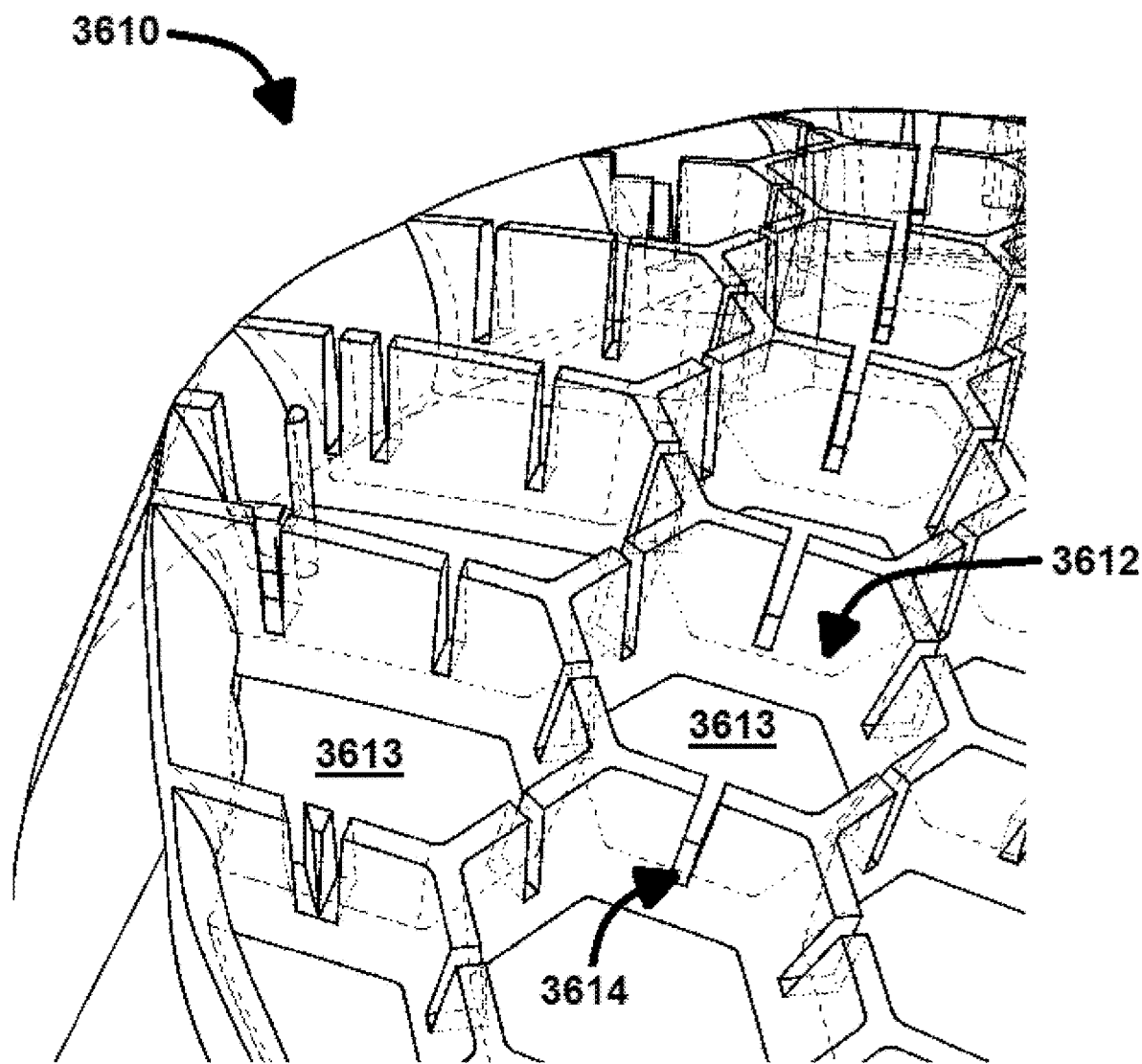
FIG. 54 depicts an enlarged view of a portion of the mold shown in FIG. 53.

Like previously described embodiments, implant (3510) can be formed by a molding process—plates (3512) are molded about the support rings (3540) as well as portions of the wires (3514) and rim (3530) of the support frame (3520). FIGS. 53 and 54 depict one such mold (3610) used to fabricate an implant similar to implant (3510). Mold (3610) includes a plurality of cavities (3612) shaped and arranged for forming mosaic plates, such as plate (3512) described previously. Thus, cavities (3612) have tapered sidewalls corresponding to the tapered sidewalls of the plates. The bottom (3613) of each cavity (3612) corresponds to the bottom surface of a plate.

Channels (3614) are provided in the sidewalls of selected cavities (3612). Channels (3614) correspond to the locations of wires (3514) of support frame (3520) and have a depth corresponding to, or slightly greater than the desired depth of the wires (3514) in the implant (3510). Thus, channels (3614) receive wires (3514) therein.

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required.

What is claimed is:

1. An implant for use in a bone defect, comprising:
   (a) a mesh support frame comprising a plurality of polygonal support rings connected to one another by a plurality of struts, said support frame having a periphery;
   (b) a plurality of biocompatible plates, wherein said polygonal support rings are positioned within said plates, with said struts extending between adjacent plates;
   (c) an outer wire rim extending about and connected to the periphery of said support frame, wherein said outer wire rim has an irregular, non-polygonal shape; and
   (d) a plurality of retention eyelets connected to and spaced outwardly away from said rim, said eyelets adapted for securing the implant in a patient.

2. The implant of claim 1, wherein said mesh support frame comprises a repeating pattern of said polygonal support rings in a spaced-apart relationship to one another, with said struts extending between the vertices of adjacent polygonal support rings.

3. The implant of claim 2, wherein said polygonal support rings comprise hexagonal parallelogons in the form of irregular hexagons.

4. The implant of claim 3, wherein said plurality of biocompatible plates are hexagonal plates, and said struts extend between the vertices of adjacent hexagonal plates.

5. The implant of claim 1, wherein said plurality of biocompatible plates are hexagonal plates, and said struts extend between the vertices of adjacent hexagonal plates.

6. The implant of claim 1, wherein said plates comprise an array of a plurality of identical hexagonal plates, with a single one of said polygonal support rings positioned within each of said hexagonal plates.

7. The implant of claim 6, further comprising a second plurality of non-identical biocompatible plates, wherein said non-identical plates are larger than said identical hexagonal plates.

8. An implant for use in a bone defect, comprising:
   (a) a rigid mesh support frame comprising a unitary structure of a plurality of interconnected wire segments forming a first plurality of polygonal support rings connected to one another by a plurality of struts, said support frame having a periphery;
   (b) a plurality of biocompatible plates, wherein said first plurality of polygonal support rings are positioned within said plates, with said struts extending between adjacent plates; and
   (c) an outer wire rim connected to a portion of said wire segments of said support frame such that the outer wire rim is connected to and extends about the periphery of said support frame; and
   (c) a plurality of fastening points comprising retention eyelets provided on retention arms that extend outwardly away from and are connected to said outer rim, wherein said retention arms are deformable;
   wherein all of the wire segments forming said struts and said polygonal support rings are angled with respect to an imaginary planar base at angle of greater than 45 degrees.

9. The implant of claim 8, wherein the implant is curved such that the implant conforms to a curved surface.

10. The implant of claim 8, wherein at least a portion of said support rings and said plates have a hexagonal shape.

11. The implant of claim 8, wherein said plates comprise a central array of a plurality of identical hexagonal plates equally spaced from one another, said central array having a periphery, and further comprising a second plurality of non-identical biocompatible plates arranged about the periphery of said central array.

12. The implant of claim 11, wherein said struts extend between the vertices of adjacent hexagonal plates of said central array.

13. The implant of claim 12, wherein said outer rim extends through said second plurality of non-identical biocompatible plates.

14. The implant of claim 11, wherein said mesh support frame further comprises a second plurality of support rings arranged about said first plurality of polygonal support rings, with said second plurality of support rings positioned within said second plurality of non-identical biocompatible plates; and
   further wherein said outer rim extends through said second plurality of non-identical biocompatible plates.

15. The implant of claim 8, wherein said mesh support frame comprises a repeating pattern of said polygonal support rings in a spaced-apart relationship to one another.

16. The implant of claim 15, wherein said struts extend between the vertices of adjacent polygonal support rings.

17. The implant of claim 15, wherein said polygonal support rings comprise hexagonal parallelogons.

18. The implant of claim 17, wherein said polygonal support rings are irregular hexagons.

19. The implant of claim 8, wherein said biocompatible plates comprise a hydraulic cement composition.

20. The implant of claim 8, wherein said biocompatible plates comprise a cement comprising at least 55 wt. % monetite.

21. A method for correcting a bone defect in a patient, comprising:
   (a) providing an implant of claim 8;
   (b) positioning the implant at the site of the bone defect in the patient; and
   (c) securing the implant in place.

* * * * *

UNITED STATES PATENT AND TRADEMARK OFFICE
CERTIFICATE OF CORRECTION

PATENT NO. : 10,881,519 B2
APPLICATION NO. : 15/503666
DATED : January 5, 2021
INVENTOR(S) : Thomas Engstrand et al.

It is certified that error appears in the above-identified patent and that said Letters Patent is hereby corrected as shown below:

In the Claims

Claim 8, Column 36, Line 27, delete "and".

Claim 8, Column 36, Line 32, change "(c)" to --(d)--.

Signed and Sealed this
Fourth Day of May, 2021

Drew Hirshfeld
*Performing the Functions and Duties of the
Under Secretary of Commerce for Intellectual Property and
Director of the United States Patent and Trademark Office*